US010597663B2

(12) United States Patent
Melnyk et al.

(10) Patent No.: US 10,597,663 B2
(45) Date of Patent: Mar. 24, 2020

(54) DELIVERY OF STRUCTURALLY DIVERSE POLYPEPTIDE CARGO INTO MAMMALIAN CELLS BY A BACTERIAL TOXIN

(71) Applicant: The Hospital for Sick Children, Toronto (CA)

(72) Inventors: Roman A. Melnyk, Oakville (CA); Anick Auger, Montreal (CA); Greg Beilhartz, Toronto (CA); Berge Minassian, Toronto (CA); Seiji Sugiman-Marangos, Toronto (CA)

(73) Assignee: THE HOSPITAL FOR SICK CHILDREN, Toronto (CA)

( * ) Notice: Subject to any disclaimer, the term of this patent is extended or adjusted under 35 U.S.C. 154(b) by 0 days.

(21) Appl. No.: 15/827,595

(22) Filed: Nov. 30, 2017

(65) Prior Publication Data
US 2018/0080033 A1 Mar. 22, 2018

Related U.S. Application Data

(63) Continuation-in-part of application No. PCT/CA2016/050612, filed on May 31, 2016.

(60) Provisional application No. 62/169,067, filed on Jun. 1, 2015.

(51) Int. Cl.

| | |
|---|---|
| *A61K 39/00* | (2006.01) |
| *A61K 39/02* | (2006.01) |
| *C07H 21/04* | (2006.01) |
| *C12N 15/62* | (2006.01) |
| *A61K 35/74* | (2015.01) |
| *C07K 14/34* | (2006.01) |
| *C07K 14/28* | (2006.01) |
| *C07K 14/33* | (2006.01) |
| *C07K 14/47* | (2006.01) |
| *C07K 14/475* | (2006.01) |
| *C12N 9/10* | (2006.01) |
| *C12N 9/22* | (2006.01) |
| *C12N 9/28* | (2006.01) |
| *C12N 9/52* | (2006.01) |
| *A61K 38/45* | (2006.01) |
| *A61K 38/48* | (2006.01) |
| *A61K 47/68* | (2017.01) |
| *A61K 47/42* | (2017.01) |
| *C07K 7/08* | (2006.01) |
| *C07K 14/00* | (2006.01) |
| *C07K 16/12* | (2006.01) |
| *C12N 11/06* | (2006.01) |
| *A61K 38/00* | (2006.01) |

(52) U.S. Cl.
CPC ............. *C12N 15/62* (2013.01); *A61K 35/74* (2013.01); *A61K 38/45* (2013.01); *A61K 38/48* (2013.01); *A61K 47/42* (2013.01); *A61K 47/6829* (2017.08); *C07K 7/08* (2013.01); *C07K 14/001* (2013.01); *C07K 14/28* (2013.01); *C07K 14/33* (2013.01); *C07K 14/34* (2013.01); *C07K 14/4703* (2013.01); *C07K 14/475* (2013.01); *C07K 16/1282* (2013.01); *C12N 9/1051* (2013.01); *C12N 9/1077* (2013.01); *C12N 9/22* (2013.01); *C12N 9/2417* (2013.01); *C12N 9/52* (2013.01); *C12N 11/06* (2013.01); *A61K 38/00* (2013.01); *C07K 2319/10* (2013.01); *C07K 2319/21* (2013.01); *C07K 2319/22* (2013.01); *C07K 2319/35* (2013.01); *C07K 2319/41* (2013.01); *C07K 2319/50* (2013.01); *C07K 2319/55* (2013.01); *C07K 2319/60* (2013.01); *C07K 2319/75* (2013.01); *C12N 2310/20* (2017.05)

(58) Field of Classification Search
CPC ............................... A61K 39/00; A61K 39/02
USPC .................. 424/184.1, 185.1, 234.1, 236.1; 536/23.1, 23.7
See application file for complete search history.

(56) References Cited

FOREIGN PATENT DOCUMENTS

| | | |
|---|---|---|
| WO | 2011133658 A1 | 10/2011 |
| WO | 2016191869 A1 | 12/2016 |

OTHER PUBLICATIONS

European Patent Application No. 16802289.5, Extended European Search Report dated Dec. 17, 2018.
International Patent Application No. PCT/CA2018/051521, International Search Report and Written Opinion dated Feb. 5, 2019.
Ainavarapu et al, "Ligand Binding Modulates the Mechanical Stability of Dihydrofolate Reductase," Biophysical Journal, Nov. 2005, vol. 89 (5), pp. 3337-3344.

(Continued)

*Primary Examiner* — Rodney P Swartz
(74) *Attorney, Agent, or Firm* — Borden Ladner Gervais LLP; Graeme R. Boocock

(57) ABSTRACT

There is a need for delivery platforms with robust capacity that offer the possibility to deliver diverse protein-based therapeutics into specific cells. Described herein is a platform for delivering cargo polypeptides into cells, which is based on a recombinant molecule comprising: a cargo polypeptide, a diphtheria toxin enzymatic fragment (DTA), and a diphtheria toxin translocation fragment (DTB). The platform has been employed to deliver diverse cargo into cells, including those having low or high molecular weights. A hyper-stable cargo polypeptide has been delivered, as well as proteins of therapeutic significance (e.g. MecP2, SMN, FMRP, PNP, alpha-amylase, and RRSP). The platform is also useful for delivering genome-modifying proteins, such as the CRISPR protein, Cas9. Associated nucleic acids, pharmaceutical compositions, methods, uses, and kits are also described, including those of therapeutic significance aimed at treating diseases or disorders caused by enzyme or protein deficiency.

21 Claims, 24 Drawing Sheets
Specification includes a Sequence Listing.

(56) References Cited

OTHER PUBLICATIONS

Alewine et al, "Advances in Anticancer Immunotoxin Therapy," The oncologist, Feb. 2015, vol. 20 (2, pp. 176-185.
Antic et al, "Site-specific processing of Ras and Rap1 Switch I by a MARTX toxin effector domain," Nature Communications, Jun. 2015, vol. 6, pp. 7396.
Auger et al., "Efficient Delivery of Structurally Diverse Protein Cargo into Mammalian Cells by a Bacterial Toxin," Molecular Pharmaceutics, Jun. 2015 , vol. 12 (8), pp. 2962-2971.
Aullo et al, "A Recombinant Diphtheria Toxin Related Human CD4 Fusion Protein Specifically Kills HIV Infected Cells Which Express GP120 but Selects Fusion Toxin Resistant Cells Which Carry HIV," The EMBO Journal, Feb. 1992, vol. 11 (2), pp. 575-583.
Bachran et al, "Anthrax toxin-mediated delivery of the Pseudomonas exotoxin A enzymatic domain to the cytosol of tumor cells via cleavable ubiquitin fusions," mBio, Apr. 2013, vol. 4 (3), pp. e00201-e00213.
Ballard et al, "Anthrax toxin-mediated delivery of a cytotoxic T-cell epitope in vivo," Proceedings of the National Academy of Sciences of the United States of America, Oct. 1996, vol. 93(22), pp. 12531-12534.
Benson et al, "Identification of residues lining the anthrax protective antigen channel," Biochemistry, Mar. 1998, vol. 37(11), pp. 3941-3948.
Choudhary et al, "Therapeutic potential of anticancer immunotoxins," Drug discovery today , Jun. 2011, vol. 16 (11-12), pp. 495-503.
Forbes et al, "COSMIC: mining complete cancer genomes in the Catalogue of Somatic Mutations in Cancer," Nucleic Acids Research, Jan. 2011, vol. 39, pp. D945-D950.
Francis et al, "A Survival Motor Neuron: Tetanus Toxin Fragment C Fusion Protein for the Targeted Delivery of SMN Protein to Neurons," Brain Research, Jan. 1995, vol. 995 (1), pp. 84-96.
Fu et al, "Selection of Diphtheria Toxin Active-Site Mutants in Yeast.Rediscovery of Glutamic Acid-148 as a Key Residue," Advances in Experimental Medicine and Biology, 1997, vol. 419, pp. 45-52.
Gaillard et al., "Diphtheria Toxin Receptor-Targeted Brain Drug Delivery," International Congress Series, Apr. 2005, vol. 1277, pp. 185-198.
International Patent Application No. PCT/CA2016/050612, International Search Report and Written Opinion dated Sep. 8, 2016.
International Patent Application No. PCT/CA2016/50612, International Preliminary Report on Patentability dated Dec. 14, 2017.
Jean et al, "Diphtheria Toxin Receptor-Binding Domain Substitution with Interleukin 6: Genetic Construction and Interleukin 6 Receptor-Specific Action of a Diphtheria Toxin-related Interleukin 6 Fusion Protein," Protein Engineering, Dec. 1991, vol. 4 (8), pp. 989-994.
Just et al, "Glucosylation of Rho proteins by Clostridium difficile toxin B," Nature, Jun. 1995, vol. 375 (6531), pp. 500-503.
King et al, "Removing T-cell epitopes with computational protein design," Proceedings of the National Academy of Sciences of the United States of America, Jun. 2014, vol. 111 (23), pp. 8577-8582.
Kiyokawa et al, "Protein Engineering of Diphtheria-Toxin-Related Interleukin-2 Fusion Toxins to Increase Cytotoxic Potency for High-affinity IL-2-Receptor-Bearing Target Cells," Protein Engineering, Apr. 1991, vol. 4 (4), pp. 463-468.
Klingenberg et al, "Ability of Methotrexate to Inhibit Translocation to the Cytosol of Dihydrofolate Reductase Fused to Diphtheria Toxin," The Biochemical Journal, Jan. 1996, vol. 313 (2), pp. 647-653.
Krantz et al, "A phenylalanine clamp catalyzes protein translocation through the anthrax toxin pore," Science, Jul. 2005, vol. 309(5735), pp. 777-781.
Leppla et al, "Anthrax toxin fusion proteins for intracellular delivery of macromolecules," Journal of applied microbiology, Aug. 1999, vol. 87 (2), pp. 284.
Liao et al, "Delivery of antibody mimics into mammalian cells via anthrax toxin protective antigen," Chembiochem : a European journal of chemical biology, Nov. 2014, vol. 15 (16), pp. 2458-2466.
Lito et al, "Tumor adaptation and resistance to RAF inhibitors," Nature Medicine, Nov. 2013, vol. 19 (11), pp. 1401-1409.
Madshus et al., "Membrane Translocation of Diphtheria Toxin Carrying Passenger Protein Domains," Infection and Immunity, Aug. 1992, vol. 60 (8), pp. 3296-3302.
Mazor et al, "Identification and elimination of an immunodominant T-cell epitope in recombinant immunotoxinsbased on Pseudomonas exotoxin A," Proceedings of the National Academy of Sciences of the United States of America, Dec. 2012, vol. 109(51), pp. E3597-E3603.
Murphy, "Mechanism of Diphtheria Toxin Catalytic Domain Delivery to the Eukaryotic Cell Cytosol and the Cellular Factors that Directly Participate in the Process," Toxins, Mar. 2011, vol. 3 (3), pp. 294-308.
Nagata et al, "Removal of B cell epitopes as a practical approach for reducing the immunogenicity of foreign protein-based therapeutics," Advanced drug delivery reviews, Sep. 2009, vol. 61 (11), pp. 977-985.
Prior et al, "A comprehensive survey of Ras mutations in cancer," Cancer, May 2012, vol. 72 (10), pp. 2457-2467.
Stenmark., et al., "Peptides Fused to the Amino-Terminal End of Diphtheria Toxin Are Translocated to the Cytosol," The Journal of Cell Biology, Jun. 1991, vol. 113 (5), pp. 1025-1032.
Wiedlocha et al, "Tight Folding of Acidic Fibroblast Growth Factor Prevents Its Translocation to the Cytosol with Diphtheria Toxin as Vector," The EMBO Journal, Dec. 1992, vol. 11 (13), pp. 4835-4842.
Williams et al, "Diphtheria Toxin Receptor Binding Domain Substitution with Interleukin-2: Genetic Construction and Properties of a Diphtheria Toxin-Related Interleukin-2 Fusion Protein," Protein Engineering, Jan. 1987, vol. 1 (6), pp. 493-498.
Zornetta et al, "Imaging the cell entry of the anthrax oedema and lethal toxins with fluorescent protein chimeras," Cellular microbiology, Oct. 2010, vol. 12 (10), pp. 1435-1445.

DELIVERY OF STRUCTURALLY DIVERSE POLYPEPTIDE CARGO INTO MAMMALIAN CELLS BY A BACTERIAL TOXIN

CROSS REFERENCE TO RELATED APPLICATIONS

This application is a continuation-in-part of international application PCT/CA2016/050612 filed May 31, 2016, which claims the benefit of priority of U.S. Provisional Patent Application No. 62/169,067, filed Jun. 1, 2015, which are herein incorporated by reference.

FIELD

The present disclosure relates generally to a polypeptide delivery platform. More particularly, the present disclosure relates to a bacterial toxin-based platform for polypeptide delivery.

BACKGROUND

In contrast with small-molecule therapeutics and probes, which often readily penetrate biological membranes, larger macromolecules, such as peptides and proteins, are generally excluded from the cell interior. Given the vast array of applications for protein-based tools and therapeutics inside cells, there is great interest in developing safe and efficient protein delivery platforms that direct biologics into cells. To date, numerous approaches have been investigated to facilitate protein entry into the cytoplasm of cells, including cell-penetrating peptides, lipid-based molecules, nanoparticles, encapsulated protein containers, zinc-finger proteins, and super-charged green fluorescent proteins. Though each is capable of delivering protein cargo into cells to varying degrees, general mechanism-based limitations exist for these platforms. Cell-selectivity and/or efficiency-of-delivery remain particularly elusive features for most platforms owing to their shared nonspecific mode of interaction with membranes.

Platforms enabling targeted delivery of proteins into cells are needed to fully realize the potential of protein-based therapeutics with intracellular sites-of-action. As such, there remains a pressing need for delivery platforms with robust capacity that offer the possibility to deliver diverse protein-based therapeutics into specific cells.

SUMMARY

It is an object of the present disclosure to obviate or mitigate at least one disadvantage of previous approaches.

In one aspect, the present disclosure provides a recombinant molecule comprising a cargo polypeptide, a diphtheria toxin enzymatic fragment (DTA), and a diphtheria toxin translocation fragment (DTB). In one embodiment, the recombinant molecule has a general structure: x-C-y-DTA-DTB, wherein: x is a polypeptide or absent, C is the cargo polypeptide, and y is a polypeptide, a linker, or absent.

In another aspect, there is provided a nucleic acid encoding the above-described recombinant molecule.

In another aspect, there is provided a recombinant cell comprising at least one above-described nucleic acid.

In another aspect, there is provided a vector comprising at least one above-described nucleic acid.

In another aspect, there is provided a cell transformed with the above-described vector.

In another aspect, there is provided a pharmaceutical composition comprising the above-described recombinant molecule, and a pharmaceutically acceptable carrier.

In another aspect, there is provided a method of delivering a cargo polypeptide to a cell, comprising contacting the cell with the above-described recombinant molecule.

In another aspect, there is provided a method of delivery a cargo polypeptide to a cell of a subject, comprising contacting the cell with the above-described recombinant molecule.

In another aspect, there is provided a method of delivering a cargo polypeptide across the blood brain barrier, comprising administering to a subject the above-described recombinant molecule.

In another aspect, there is provided a method of increasing enzyme or protein activity in a cell, comprising contacting the cell with the above-described recombinant molecule.

In another aspect, there is provided a method of alleviating enzyme or protein deficiency in a cell, comprising contacting the cell with the above-described recombinant molecule.

In another aspect, there is provided a method of treating a disease or disorder caused by enzyme or protein deficiency in a subject, comprising administering to the subject the above-described recombinant molecule.

In another aspect, there is provided a method of manipulating the genome of a cell, comprising contacting the cell with the above-described recombinant molecule, wherein the cargo polypeptide comprises a genome-modifying protein.

In another aspect, there is provided a use of the above-described recombinant molecule for delivery, or for preparation of a medicament for delivery, of the cargo polypeptide to a cell.

In another aspect, there is provided a use of the above-described recombinant molecule for delivery, or for preparation of a medicament for delivery, of the cargo polypeptide to a cell of a subject.

In another aspect, there is provided a use of the above-described recombinant molecule for delivery, or for preparation of a medicament for delivery, of the cargo polypeptide across the blood brain barrier.

In another aspect, there is provided a use of the above-described recombinant molecule for increasing, or for preparation of a medicament for increasing, enzyme or protein activity in a cell.

In another aspect, there is provided a use of the above-described recombinant molecule for alleviating, or for preparation of a medicament for alleviating, enzyme or protein deficiency in a cell.

In another aspect, there is provided a use of the above-described recombinant molecule for treating, or for preparation of a medicament for treating, a disease or disorder caused by enzyme or protein deficiency in a subject.

In another aspect, there is provided a use of the above-described recombinant molecule for manipulating the genome of a cell, wherein the cargo polypeptide comprises a genome-modifying protein.

In another aspect, there is provided a kit for delivering a cargo polypeptide to a cell comprising the above-described recombinant molecule, and instructions for contacting the cell with the recombinant molecule.

In another aspect, there is provided a kit for delivering a cargo polypeptide to a cell of a subject, comprising the above-described recombinant molecule, and instructions for contacting the cell with the recombinant molecule.

In another aspect, there is provided a kit for delivering a cargo polypeptide across the blood brain barrier, comprising the above-described recombinant molecule, and instructions for administering the recombinant molecule to a subject.

In another aspect, there is provided a kit for increasing enzyme or protein activity in a cell, comprising the above-described recombinant molecule, and instructions for contacting the cell with the recombinant molecule.

In another aspect, there is provided a kit for alleviating enzyme or protein deficiency in a cell, comprising the above-described recombinant molecule, and instructions for contacting the cell with the recombinant molecule.

In another aspect, there is provided a kit for treating a disease or disorder caused by enzyme or protein deficiency in a subject, comprising the above-described recombinant molecule, and instructions for administering the recombinant molecule to the subject.

In another aspect, there is provided a kit for manipulating the genome of cell, comprising the above-described recombinant molecule, and instructions for contacting the cell with the recombinant molecule, wherein the cargo polypeptide comprises a genome-modifying protein.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

FIG. 29 depicts the results of cell viability assays to assess the effects of removing most of the DTA domain.

Recombinant Molecules

Figure 1:
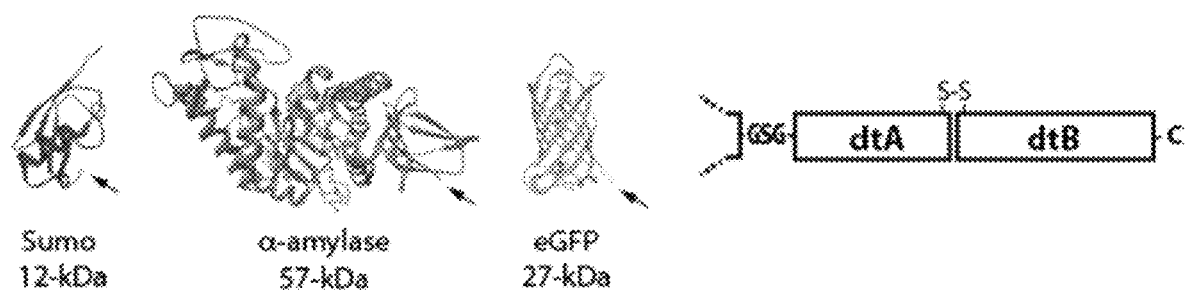
FIG. 1 depicts representative structures of the three different passenger proteins: sumo protein; α-amylase; and eGFP. Arrows indicate the C-terminus of each protein.

In one aspect, there is provided a recombinant molecule comprising a cargo polypeptide, a diphtheria toxin enzymatic fragment (DTA), and a diphtheria toxin translocation fragment (DTB).

'DTA', as used herein, refers to the diphtheria toxin enzymatic A fragment generally, while 'DTB' refers to the receptor-binding/translocation B fragment generally.

By 'fragment' is meant a sequence of amino acids that includes the relevant domain, or a subsequence thereof from which some or all of the relevant domain has been removed. Though terms "enzymatic fragment" or "receptor-binding/translocation" are used by convention, it will be understood that some such fragments are functional, while others may have reduced function or may not be functional. For example, in the case of DTA, a 'fragment' may encompass the entirety of SEQ ID NO: 1 (dtA) or SEQ ID NO: 2 (dta), but is also to be understood as encompassing subsequences thereof.

By 'domain' is meant a particular functional and/or structural unit of a protein, often responsible for a particular function or interaction that contributes to the overall role of a protein. Protein domains may be evolutionarily conserved.

Where 'dtA' is used, it refers to a catalytically active form of DTA, unless otherwise specified. Likewise, and 'dta' is used herein to refer to the catalytically inactive form, unless otherwise specified. 'dtB', as used herein, refers to functional DTB, unless otherwise specified.

By 'catalytically active' is meant that the DTA is enzymatically active, i.e. toxic to the relevant cells. By 'catalytically inactive' is meant that the DTA is enzymatically inactive, i.e. non-toxic to the relevant cells.

The recombinant molecule may be used with a cargo polypeptide of any size. The size can be less than 1 kDa, less than 2 kDa, less than 5 kDa, less than 10 kDa, or greater than 10 kDa. The recombinant molecule may be useful for delivering cargo polypeptides of relatively large size, for example, greater than 10 kDa, 20 kDa, 30 kDa, 40 kDa, 50 kDA, 60 kDA, 70 kDa, 80 kDa, 90 kDa, 100 kDa, 110 kDa, 120 kDa, 130 kDa, 140 kDa, 150 kDa, or 160 kDa. For example, the cargo polypeptide may have a molecular weight of greater than 10 kDa. The cargo polypeptide may have a molecular weight greater than 20 kDa. The cargo polypeptide may have a molecular weight greater than 30 k Da. The cargo polypeptide may have a molecular weight greater than 50 kDa. The cargo polypeptide may also have a molecular weight of greater than 100 kDa. The cargo polypeptide may also have a molecular weight of greater than 150 kDa. The cargo polypeptide may be positioned at or upstream of the amino terminus of the diphtheria toxin enzymatic fragment.

The cargo polypeptide may be a modified sequence, e.g. containing chemically modified, mutated, or non-natural amino acids. For instance, the cargo polypeptides may be modified to increase stability as compared to, e.g., the unmodified or natural counterpart sequence.

In one embodiment, the recombinant molecule has a general structure: x-C-y-DTA-DTB, wherein: x is a polypeptide or absent, C is the cargo polypeptide, and y is a polypeptide, a linker, or absent. DTA can, for instance, be linked to the DTB by way of a disulphide linkage. This may be formed via a cysteine residue corresponding to the cysteine at position 186 of SEQ ID NOs: 1 or 2; and a cysteine residue corresponding to the cysteine at position 2 of SEQ ID NO: 3.

In one embodiment, y is an autoprocessing domain. Autoprocessing domains are those that effect their own cleavage. In one embodiment, an autoprocessing domain that cleaves at or near its own N-terminus, e.g. to "self clear" is desirable. Using an autoprocessing domain of this sort, cargo polypeptide may be released into the cytosol. The autoprocessing domain may comprise a cysteine protease domain (CPD). This protein family is well known. The CPD may be derived from a bacterium, such as *Vibrio cholerae* or *Clostridium difficile*. These cysteine protease domains may comprises an amino acid sequence as set forth in SEQ ID No: 20 or 21, respectively. In one embodiment, the polypeptide of y additionally comprises one or more linker.

In one embodiment, y is a linker. The linker may be an amino acid linker. When placed between a cargo polypeptide and DTA or DTB, the linker may be of sufficient length so as not to inhibit (or reduce or minimize inhibit) DTA or DTB. The linker may comprise at least 1, 2, 3, or 4 amino acid residues. The linker may comprises, e.g. at least five amino acid residues. The amino acid linker may comprise $(G4S)_n$, wherein n is 1 or greater, for instance 1 to 3. In one embodiment, n is 3.

In one embodiment, x is absent.

DTB may comprise an amino acid sequence as set forth in SEQ ID No: 3.

DTA may be catalytically active (dtA) or catalytically inactive (dta). An example of a catalytically active DTA is one comprising an amino acid sequence as set forth in SEQ ID No: 1. An example of a catalytically inactive DTA is one bearing the mutations K51E and E148K, as numbered with respect to wild type sequence. For instance, an inactive DTA may comprise an amino acid sequence as set forth in SEQ ID No: 2.

The cargo polypeptide may comprise any polypeptide for which cellular delivery is desired.

The cargo polypeptide may comprise an enzyme, or an active fragment thereof having substantially the same activity. By 'substantially the same activity' is meant that a core function of the enzyme is substantially unaltered in the fragment.

The cargo polypeptide may comprise a stably folded, or hyper stable polypeptide. By 'hyper stable' is meant a polypeptide that is not susceptible to unfolding. mCherry is one example of a stably folded protein. mCherry is not susceptible to unfolding at high temperatures, i.e. of 80 degrees Celsius. The cargo polypeptide may accordingly be a polypeptide that resists unfolding up to 60, 70, 80, 90, or 100 degrees Celsius. mCherry is also stable down to pH 4. The cargo polypeptide may accordingly be a polypeptide that resists unfolding down to pH 5.0, 4.5, 4.0, 3.5, 3.0, 2.5, 2.0, 1.5, or 1.0.

The cargo polypeptide may comprise a therapeutic protein. By 'therapeutic polypeptide' is meant any protein, the cellular delivery of which could be used for a therapeutic purpose. It is well known, for example, that many human diseases or disorders are caused by or characterized by protein deficiency. Therapeutic proteins encompass proteins, the delivery of which could ameliorate or correct such a deficiency. A therapeutic protein may act to replace a protein that is deficient in the disease or disorder. A therapeutic protein may be the protein that is deficient in the disease or disorder. However, a therapeutic protein need not necessarily be identical to the protein that is deficient in the disease or disorder. For instance, a therapeutic protein may be an active fragment or modified form of a deficient protein. A therapeutic protein may also partially or fully functionally compensate for the protein deficiency underlying the disease or disorder. A therapeutic protein may also ameliorate or correct downstream or secondary effects of the cellular deficiency in a particular protein. As an example, while Lafora disease is caused e.g. by mutations in EPM2A or NHLRC1 (EPM2B), it is envisaged that delivery of an amylase, such as an alpha-amylase, as a therapeutic protein could help to reduce or clear Lafora bodies. The cargo polypeptide may comprise MecP2 (e.g. SEQ ID No: 16 or 17), SMN (e.g. SEQ ID No: 19), FMRP (e.g. SEQ ID No: 18), PNP (e.g. SEQ ID No: 24), or alpha-amylase (e.g. SEQ ID No: 15).

The modified form may comprise, e.g., a functional variant comprising one or more sequence changes that do not substantially impact function of the parent cargo or protein.

In one embodiment, the cargo protein comprises RRSP (Ras/Rap1-specific endopeptidase) from *Vibrio vulnificus*, a functional variant, a functional fragment, or a homologue thereof. In one embodiment, the cargo protein comprises RRSP (Ras/Rap1-specific endopeptidase) from *Vibrio vulnificus*. As referred to herein, the RRSP may be as encoded by SEQ ID NO: 26. The RRSP may comprise amino acids having the sequence of SEQ ID NO: 27. The RRSP may consist of amino acids having the sequence of SEQ ID NO: 27. The cargo protein may comprise a functional variant of RRSP having substantially the same function as RRSP comprising amino acids having the sequence of SEQ ID NO: 27. The cargo protein may comprise of a functional variant of RRSP having substantially the same function as RRSP consisting of amino acids having the sequence of SEQ ID NO: 27. Functional variants of RRSP, as referred to herein, may comprise sequence changes that do not substantially impact function. The variant may comprise 80%, 85%, 90%, 95%, 96%, 97%, 98%, or 99% sequence identity to SEQ ID NO: 27. The cargo protein may comprise a functional fragment of RRSP. The cargo protein may consist of a functional fragment of RRSP. Such fragments will be understood as N- or C-terminal truncations of RRSP that substantially maintain function. The cargo protein may comprise a homologue of RRSP having a homologous function in another species. Some such homologues are as disclosed in reference 29. However, homologues of RRSP, as referred to herein, could also be readily identified, e.g. by BLAST searching using SEQ ID NO: 27. Putative homologues could be tested for the ability to cleave Ras using methods described, e.g. in reference 29. Homologues, as referred to herein, may comprise proteins having amino acid sequences that are 80%, 85%, 90%, 95%, 96%, 97%, 98%, or 99% sequence identity to SEQ ID NO: 27.

An example of a recombinant molecule according to on embodiment is x-RRSP-y-DTA-DTB, wherein the constituents are as defined herein. A further Example is x-RRSP-y-dta-dtB, wherein dta comprises amino acids having SEQ ID NO: 28. A further Example is x-RRSP-y-dta-dtB, wherein dta consists of amino acids having SEQ ID NO: 28. In these constructs, x may be absent in some embodiments. In one embodiment, y is a polypeptide comprising an autoprocessing domain, e.g., as described herein. In one embodiment, y is a polypeptide comprising one or more linker, e.g., as described herein. In one embodiment, y is a polypeptide comprising both an autoprocessing domain and a linker. The linker may comprise a $(G4S)_2$ linker. The recombinant molecule may be the construct termed "RRSP-Δdta-dtB" and described in Example 15.

The cargo polypeptide comprises a genome-modifying protein. The genome-modifying protein comprises a zinc finger nuclease (ZFN), a transcription activator-like effector nuclease (TALEN), or a CRISPR (clustered regularly interspaced short palindromic repeat) protein. The CRISPR protein may be Cas9 (e.g. SEQ ID No: 22). The cargo polypeptide may comprise a complex of the genome-modifying protein and a nucleic acid, such as a guide nucleic acid. For instance, Cas9 may be complexed with a nucleic acid (such as a guide RNA), such as crRNA, trRNA, and/or sgRNA.

The amino acid sequences referred to herein encompass sequence differences compared to the references sequences (such as those set forth in Table 1, below). These may be variants, mutations, insertions, or deletions. In some applications, it may be important to ensure that the primary function of the protein is not substantially altered or abrogated, but this can be readily tested, e.g. using assays described herein. The amino acid sequences described herein may comprise a sequence of 75% or greater, 80% or greater, 85% or greater, 90% or greater, 95% or greater, or 99% or greater identity to the references sequences. The amino acid sequences may encompass conservative amino substitutions. Conservative amino acid substitutions which are known in the art are as follows with conservative substitutable candidate amino acids showing in parentheses: Ala (Gly, Ser); Arg (Gly, Gln); Asn (Gln; His); Asp (Glu); Cys (Ser); Gln (Asn, Lys); Glu (Asp); Gly (Ala, Pro); His (Asn; Gln); Ile (Leu; Val); Leu (Ile; Val); Lys (Arg; Gln); Met (Leu, Ile); Phe (Met, Leu, Tyr); Ser (Thr; Gly); Thr (Ser; Val); Trp (Tyr); Tyr (Trp; Phe); Val (Ile; Leu). Some so-called 'functional' variants, mutations, insertions, or deletions encompass sequences in which the function is substantially the same as that of the reference sequence, e.g. from which it is derived. This can be readily tested using assays similar to those described herein.

The amino acid sequences referred to herein, in particular the DT sequences may be modified for some applications. It may be desirable, for instance, to reduce the antigenicity of the fusion protein or the DT domains. They may be accomplished in a number of ways. For example, an amino acid sequence could be PEGylated. The amino acid sequence may also be mutated, e.g. to reduce antigenicity, for example by removing B- and/or T-cell epitopes. Humanization is one example mode of sequence modification.

In one embodiment, the cargo comprises an ubiquitin or a variant thereof. In one embodiment, the cargo comprises ubiquitin.

As mentioned previously, a 'variant' may encompass sequences that encompasses sequence differences with respect to a reference sequence, e.g. which may have 75% or greater, 80% or greater, 85% or greater, 90% or greater, 95% or greater, or 99% or greater identity to the references sequence. A 'variant' may also encompass amino acid substitutions, such as aforementioned conservative amino substitutions. Variants may also encompass sequence changes aimed at humanizing and/or reducing antigenicity.

In one embodiment, the cargo polypeptide comprises a therapeutic polypeptide. By 'therapeutic peptide' is meant any amino acid sequence that is delivered for a therapeutic purpose, e.g. to treat, prevent, or ameliorate a disease or pathological state.

In one embodiment, y comprises a ligation site. By 'ligation site' is meant the product of a ligation reaction. This could encompass, e.g., a particular sequence or a chemical structures that is the product of a ligation reaction. In one embodiment, the ligation site is a sortase ligation site.

In some embodiments, it may be advantageous to reduce the size of the recombinant molecule, i.e. to provide a smaller construct or lower antigenicity.

The DTA may be a subsequence of dtA or dta in some embodiments. In one embodiment, the DTA is a C-terminal fragment comprising a cysteine corresponding to the cysteine at position 186 of SEQ ID NO: 1. By 'corresponding to' is meant a position at the equivalent or cognate position when, e.g., two sequences are compared or aligned.

In one embodiment, the C-terminal fragment comprises a polypeptide having a sequence CAGNRVRRSVGSSL (SEQ ID NO: 28). In one embodiment, the C-terminal fragment consists of a polypeptide having a sequence CAGNRVRRS-VGSSL (SEQ ID NO: 28). However, in some embodiments, DTA may be a different C-terminal fragment longer than SEQ ID NO: 28 but shorter than SEQ ID NOs: 1 or 2.

Nucleic Acids, Vectors, and Cells

In one aspect, there is provided a nucleic acid encoding the above-described recombinant molecule. It will be appreciated that DTA and DTB, being separate polypeptides in the wild type diphtheria toxic linked by a disulphide bridge, may be separately encoded. Accordingly, in the nucleic acid, the DTA and DTB may be separately encoded. Separate nucleic acids encoding each of DTA and DTB may also be provided.

A skilled person would readily appreciate there are many ways to encode the above-described recombinant molecule (e.g. due to degeneracy of the genetic code), all of which are encompassed. Deletions, insertions, and substitutions may also be permitted if protein function remains substantially intact. For instance, nucleic acids may have 75% or greater, 80% or greater, 85% or greater, 90% or greater, 95% or greater, or 99% or greater identity to wild-type or references sequences may be encompassed. The above-noted nucleic acids could also be codon optimized depending on the organism or expression system in which it is intended to be expressed.

In one aspect, there is provided a recombinant cell comprising the above-described nucleic acid.

In one aspect, there is provided a vector comprising the above-described nucleic acid. Vectors suitable for propagated nucleic acid in bacterial and/or eukaryotic cells are well known in the art.

In one aspect, there is provided a cell transformed with the above-described vector. Transformation methods for obtaining such cells are well known.

Pharmaceutical Compositions and Dosage Forms

In one aspect, there is provided a pharmaceutical composition comprising the above-described recombinant molecule and a pharmaceutically acceptable carrier. In some applications, a recombinant molecule comprising non-toxic, catalytically inactive DTA (dta) may be preferred. For example, a DTA having K51E and E148K mutations may be useful in such applications. A skilled person could generate and test other mutations, e.g. using cellular assays such as those described herein, to determine which have desirable properties in this regard. The DTA may comprise a sequence as set forth in SEQ ID No: 2. The DTA may comprise variants or modification of this sequence, such as those discussed above.

For some therapeutic applications, it may be desirable to reduce the antigenicity of the fusion protein or the DT domains. They may be accomplished in a number of ways. For example, an amino acid sequence could be PEGylated. The amino acid sequence may also be mutated, e.g. to reduce antigenicity, for example by removing B- and/or T-cell epitopes. Humanization is one example mode of sequence modification.

Pharmaceutically acceptable carriers include solvents, diluents, liquid vehicles, dispersion or suspension aids, surface active agents, isotonic agents, thickening or emulsifying agents, preservatives, solid binders, or lubricants. Carriers may be selected to prolong dwell time for sustained release appropriate to the selected route of administration. Exemplary carriers include sugars such as glucose and sucrose, starches such as corn starch and potato starch, fibers such as cellulose and its derivatives, sodium carboxymethyl cellulose, ethyl cellulose, cellulose acetate, powdered tragacanth, malt, gelatin, talc, cocoa butter, suppository waxes, oils such as peanut oil, cottonseed oil, safflower oil, sesame oil, olive oil, corn oil, and soybean oil; glycols such as propylene glycol, esters such as ethyl oleate and ethyl laurate, agar, buffering agents such as magnesium hydroxide and aluminum hydroxide, alginic acid, pyrogen-free water, isotonic saline, Ringer's solution, ethyl alcohol, phosphate buffer solutions, non-toxic compatible lubricants such as sodium lauryl sulfate and magnesium stearate, coloring agents, releasing agents, coating agents, sweeteners, flavors, perfuming agents, preservatives, and antioxidants.

Compositions can be administered to subjects through any acceptable route, such as topically (as by powders, ointments, or drops), orally, rectally, mucosally, sublingually, parenterally, intracisternally, intravaginally, intraperitoneally, bucally, ocularly, or intranasally.

Liquid dosage forms for oral administration may include emulsions, microemulsions, solutions, suspensions, syrups and elixirs. Liquid dosage forms may contain inert diluents such as water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils such as cottonseed, groundnut, corn, germ, olive, castor, and sesame oils, glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required.

Injectable preparations, such as sterile injectable aqueous or oleaginous suspensions may be formulated according to the known art using suitable dispersing or wetting agents and suspending agents. The sterile injectable preparation may also be a sterile injectable solution, suspension or emulsion in a non-toxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized prior to addition of spores, for example, by filtration through a bacterial-retaining filter, or by incorporating sterilizing agents in the form of sterile solid compositions which can be dissolved or dispersed in sterile water or other sterile injectable medium prior to use.

It is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral, mucosal or sublingual administration include capsules, tablets, pills, powders, and granules. In such solid dosage forms, the active agent is mixed with at least one inert, pharmaceutically acceptable excipient or carrier such as sodium citrate or dicalcium phosphate, fillers or extenders such as starches, sucrose, glucose, mannitol, and silicic acid, binders such as, for example, carboxymethylcellulose, alginates, gelatin, polyvinylpyrrolidinone, sucrose, and acacia, humectants such as glycerol, disintegrating agents such as agar-agar, calcium carbonate, potato or tapioca starch, alginic acid, certain silicates, and sodium carbonate, solution retarding agents such as paraffin, absorption accelerators such as quaternary ammonium compounds, wetting agents such as, for example, cetyl alcohol and glycerol monostearate, absorbents such as kaolin and bentonite clay, and lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, such as tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active agent(s) only, or preferentially, in a certain part of the intestinal tract, optionally, in a delayed manner. Examples of embedding compositions which can be used include polymeric substances and waxes.

The therapeutically effective amount may be determined on an individual basis or on the basis of the established amount necessary. The dosage for an individual subject is chosen in view of the subject to be treated. Dosage and administration may be adjusted to provide sufficient levels of the active agent(s) or to maintain the desired effect. Factors which may be taken into account include the severity of the disease state, contact with infectious agent in the past, potential future contact; age, weight, gender of the subject, diet, time and frequency of administration, drug combinations, reaction sensitivities, and tolerance/response to therapy. Sustained release compositions might be administered less frequently than fast-acting compositions.

Methods

In one aspect, there is provided a method of delivering a cargo polypeptide to a cell, comprising contacting the cell with the above-described recombinant molecule.

In one aspect, there is provided a method of delivery a cargo polypeptide to a cell of a subject, comprising contacting the cell with the above-described recombinant molecule.

In one aspect, there is provided a method of delivering a cargo polypeptide across the blood brain barrier, comprising administering to a subject the above-described recombinant molecule.

In one aspect, there is provided a method of increasing enzyme or protein activity in a cell, comprising contacting the cell with the above-described recombinant molecule.

In one aspect, there is provided a method of alleviating enzyme or protein deficiency in a cell, comprising contacting the above-described recombinant molecule. In one embodiment, the cargo polypeptide comprises the enzyme or protein, or an active fragment thereof having substantially the same activity. In another embodiment, the cargo polypeptide compensates for the enzyme or protein deficiency.

By 'compensate', as used herein, is meant that the cargo polypeptide corrects or at least partially ameliorates the protein or enzyme deficiency, an aspect of the deficient protein or enzyme's function, or one or more of its downstream or secondary cellular effects or consequences.

In one aspect, there is provided a method of treating a disease or disorder caused by enzyme or protein deficiency in a subject, comprising administering to the subject the above-described recombinant molecule. In one embodiment, the cargo polypeptide comprises the enzyme or protein, or an active fragment thereof having substantially the same activity. In another embodiment, the cargo polypeptide compensates for the enzyme or protein deficiency. The disease or disorder may be Rett syndrome, and the cargo polypeptide may comprise MecP2 (e.g. SEQ ID No: 16 or 17). The disease or disorder may be Spinal Muscular Atrophy syndrome, and the cargo polypeptide may comprise SMN (e.g. SEQ ID No: 19). The disease or disorder may be Fragile X syndrome, and the cargo polypeptide may comprise FMRP (e.g. SEQ ID No: 18). The disease or disorder may be PNP-deficiency, and the cargo polypeptide may comprise PNP (e.g. SEQ ID No: 24). The disease or disorder may be Lafora Disease, and the cargo polypeptide may comprise alpha-amylase.

In one aspect, there is provided a method of treating a disease or disorder caused by protein over-expression, comprising administering to the subject the above-described recombinant molecule. Here, an aim may be e.g., to reduce expression of said protein, to inactivate said protein, or to increase degradation said protein.

In one embodiment the disease or disorder may be cancer. In one embodiment the cancer may be characterized by cells over-expressing one or more Ras protein (e.g., relative to comparable healthy cells). The one or more Ras protein may comprises one or more mutant Ras protein. In some embodiments, the one or more mutant Ras protein may comprise mutant forms of KRas, NRas, and/or HRas. In one embodiment, the cargo may comprise RRSP, a functional variant, a functional fragment, or a homologue thereof, as defined herein. The cargo may comprise RRSP. The cargo may consist of RRSP. A nucleic acid sequence encoding RRSP is depicted in SEQ ID NO: 26. A encoded amino acid sequence is depicted in SEQ ID NO: 27.

In one embodiment, there is provided a method of delivering RRSP, a functional variant, a functional fragment, or a homologue thereof to a cell, comprising contacting the cell with the above-described recombinant molecule, wherein the recombinant molecule comprises RRSP, a functional variant, a functional fragment or a homologue thereof. The recombinant molecule may comprise RRSP. The method may be carried out in vitro. The method may be carried out in vivo.

In one embodiment, there is provided a method of reducing levels of one or more mutant Ras protein in a cell, comprising contacting the cell with the above-described recombinant molecule, wherein the recombinant molecule comprises RRSP, a functional variant, a functional fragment, or a homologue thereof. The recombinant molecule may comprise RRSP. In some embodiments, the one or more mutant Ras protein may comprise mutant forms of KRas, NRas, and/or HRas. The method may be carried out in vitro. The method may be carried out in vivo.

In one embodiment, there is provided a method of inhibiting or reducing cell division of cells comprising increased levels of one or more mutant Ras protein, comprising contacting the cell with the above-described recombinant molecule, wherein the recombinant molecule comprises RRSP, a functional variant, a functional fragment, or a homologue thereof. The recombinant molecule may comprise RRSP. In some embodiments, the one or more mutant Ras protein may comprise mutant forms of KRas, NRas, and/or HRas. The method may be carried out in vitro. The method may be carried out in vivo.

In the methods described herein, the cargo polypeptide may have a molecular weight of less than 10 kDa, greater than 10 kDa, greater than 20 kDa, greater than 30 kDa, greater than 50 kDa, greater than 100 kDa, or greater than 150 kDa.

In one aspect, there is provided a method of manipulating the genome of a cell, comprising contacting the cell with the above-described recombinant molecule, wherein the cargo polypeptide comprises a genome-modifying protein. Genome-modifying proteins for genetic engineering are widely known. The genome-modifying protein may be, for example, a zinc finger nuclease (ZFN), a transcription activator-like effector nuclease (TALEN), or a CRISPR clustered regularly interspaced short palindromic repeat) protein. For example, the CRISPR protein may be Cas9 (e.g. SEQ ID No: 22). In some embodiments, these nucleic acids, such as guide RNAs, may be separately delivered to cells. In others, a pre-complex of protein and nucleic acid may be formed for delivery into a cell.

For applications of the above methods involving subjects or therapy, a recombinant molecule comprising non-toxic, catalytically inactive DTA (dta) may be preferred. For example, a DTA having K51E and E148K mutations may be useful in such applications. A skilled person could generate and test other mutations, e.g. using cellular assays such as those described herein, to determine which have desirable properties in this regard. The DTA may comprise a sequence as set forth in SEQ ID No: 2. The DTA may comprise variants or modification of this sequence, such as those discussed above.

For some therapeutic applications, it may be desirable to reduce the antigenicity of the fusion protein or the DT domains. They may be accomplished in a number of ways. For example, an amino acid sequence could be PEGylated. The amino acid sequence may also be mutated, e.g. to reduce antigenicity, for example by removing B- and/or T-cell epitopes. Humanization is one example mode of sequence modification.

Uses

In one aspect, there is provided a use of the above-described recombinant molecule for delivery, or for preparation of a medicament for delivery, of the cargo polypeptide to a cell.

In one aspect, there is provided a use of the above-described recombinant molecule, or for preparation of a medicament for delivery, of the cargo polypeptide to a cell of a subject In one aspect, there is provided a use of the above-described recombinant molecule for delivery, or for preparation of a medicament for delivery, of the cargo polypeptide across the blood brain barrier.

In one aspect, there is provided a use of the above-described recombinant molecule for increasing, or for preparation of a medicament for increasing, enzyme or protein activity in a cell.

In one aspect, there is provided a use of the above-described recombinant molecule for alleviating, or for preparation of a medicament for alleviating, enzyme or protein deficiency in a cell. In one embodiment, the cargo polypeptide comprises the enzyme or protein, or an active fragment thereof having substantially the same activity. In another embodiment, the cargo polypeptide compensates for the enzyme or protein deficiency.

In one aspect, there is provided a use of the above-described recombinant molecule, or for preparation of a medicament for treating, a disease or disorder caused by enzyme or protein deficiency in a subject. In one embodiment, the cargo polypeptide comprises the enzyme or protein, or an active fragment thereof having substantially the same activity. In another embodiment, the cargo polypeptide compensates for the enzyme or protein deficiency. The disease or disorder may be Rett syndrome, and the cargo polypeptide may comprise MecP2 (e.g. SEQ ID No: 16 or 17). The disease or disorder may be Spinal Muscular Atrophy syndrome, and the cargo polypeptide may comprise SMN (e.g. SEQ ID No: 19). The disease or disorder may be Fragile X syndrome, and the cargo polypeptide may comprise FMRP (e.g. SEQ ID No: 18). The disease or disorder may be PNP-deficiency, and the cargo polypeptide may comprise PNP (e.g. SEQ ID No: 24). The disease or disorder may be Lafora Disease, and the cargo polypeptide may comprise alpha-amylase (e.g. SEQ ID No: 15).

In one aspect, there is provided a use of the above-described recombinant molecule for preparation of a medicament for treatment of a disease or disorder caused by enzyme or protein over-expression. In one aspect, there is provided a use of the above-described recombinant molecule for treatment of a disease or disorder caused by enzyme or protein over-expression. In one aspect, there is provided the above-described recombinant molecule for use in treatment of a disease or disorder caused by enzyme or protein over-expression. The protein over-expressed may be a mutant form, e.g. which may not normally be present in corresponding healthy cells. The protein may be an oncogene.

In one embodiment the disease or disorder may be cancer. In one embodiment the cancer may be characterized by cells over-expressing one or more protein (e.g., relative to comparable healthy cells). The protein may be an oncogene. The oncogene may be a Ras protein. The one or more Ras protein may comprises one or more mutant Ras protein. In some embodiments, the one or more mutant Ras protein may comprise mutant KRas, NRas, and/or HRas. In one embodiment, the cargo may comprise RRSP, a functional variant, a functional fragment, or a homologue thereof. In one embodiment, the cargo protein may comprise RRSP.

In one embodiment, there is provided a use of the above-described recombinant molecule for preparation of a medicament for delivery of RRSP, a functional variant, a functional fragment, or a homologue thereof to a cell. The use may be for the delivery of RRSP. The use may be in vitro. The use may be in vivo. In one embodiment, there is provided a use of the above-described recombinant molecule for delivery of RRSP, a functional variant, a functional fragment, or a homologue thereof to a cell. The use may be for delivery of RRSP. The use may be in vitro. The use may be in vivo. In one embodiment, there is provided the above-described recombinant molecule for use in delivery of RRSP, a functional variant, a functional fragment, or a homologue thereof to a cell. The recombinant molecular may be for use in delivery of RRSP. The recombinant molecule may be for use be in vitro. The recombinant molecule may be for use may be in vivo. The delivery may provide the cargo (e.g. RRSP) at a therapeutically efficacious level.

In one embodiment, there is provided a use of the above-described recombinant molecule for preparation of a medicament for reduction of the levels of one or more mutant Ras protein in a cell, wherein the recombinant molecule comprises RRSP, a functional variant, a functional fragment, or a homologue thereof. The recombinant molecule may comprise RRSP. In one embodiment, there is provided a use of the above-described recombinant molecule for reduction of the levels of one or more mutant Ras protein in a cell, wherein the recombinant molecule comprises RRSP, a functional variant, a functional fragment, or a homologue thereof. The recombinant molecule may comprise RRSP. The use may be in vitro. The use may be in vivo. In one embodiment, there is provided the above-described recombinant molecule for use in reduction of the levels of one or more mutant Ras protein in a cell, wherein the recombinant molecule comprises RRSP, a functional variant, a functional fragment, or a homologue thereof. The recombinant molecule may comprise RRSP. The recombinant molecule may be for use in vitro. The recombinant molecule may be for use in vivo. In some embodiments, the one or more mutant Ras protein may comprise mutant KRas, NRas, and/or HRas.

In one embodiment, there is provided a use of the above-described recombinant molecule for preparation of a medicament for inhibition or reduction of cell division of cells comprising increased levels of one or more mutant Ras protein, wherein the recombinant molecule comprises RRSP, a functional variant, a functional fragment, or a homologue thereof. The recombinant molecular may comprise RRSP. In one embodiment, there is provided a use of the above-described recombinant molecule for inhibition or reduction of cell division of cells comprising increased levels of one or more mutant Ras protein, wherein the recombinant molecule comprises RRSP, a functional variant, a functional fragment, or a homologue thereof. The recombinant molecular may comprise RRSP. The use may be in vitro. The use may be in vivo. In one embodiment, there is provided the above-described recombinant molecule for use in inhibition or reduction of cell division of cells comprising increased levels of one or more mutant Ras protein, wherein the recombinant molecule comprises RRSP, a functional variant, a functional fragment, or a homologue thereof. The recombinant molecular may comprise RRSP. The recombinant molecule may be for use in vitro. The recombinant molecule may be for use in vivo. In some embodiments, the one or more mutant Ras protein may comprise mutant KRas, NRas, and/or HRas.

In the uses described herein, the cargo polypeptide may have a molecular weight of less than 10 kDa, greater than 10 kDa, greater than 20 kDa, greater than 30 kDa, greater than 50 kDa, greater than 100 kDa, or greater than 150 kDa.

In one aspect, there is provided a use of the above-described recombinant molecule for manipulating the genome of a cell, wherein the cargo polypeptide comprises a genome-modifying protein. Genome-modifying proteins for genetic engineering are widely known. The genome-modifying protein may be, for example, a zinc finger nuclease (ZFN), a transcription activator-like effector nuclease (TALEN), or a CRISPR clustered regularly interspaced short palindromic repeat) protein. For example, the CRISPR protein may be Cas9 (e.g. SEQ ID No: 22). In some embodiments, these nucleic acids, such as guide RNAs, may be separately delivered to cells. In others, a pre-complex of protein and nucleic acid may be formed for delivery into a cell.

For applications of the above uses involving subjects or therapy, a recombinant molecule comprising non-toxic, catalytically inactive DTA (dta) may be preferred. For example, a DTA having K51E and E148K mutations may be useful in such applications. A skilled person could generate and test other mutations, e.g. using cellular assays such as those described herein, to determine which have desirable properties in this regard. The DTA may comprise a sequence as set forth in SEQ ID No: 2. The DTA may comprise variants or modification of this sequence, such as those discussed above.

For some therapeutic applications, it may be desirable to reduce the antigenicity of the fusion protein or the DT domains. They may be accomplished in a number of ways. For example, an amino acid sequence could be PEGylated. The amino acid sequence may also be mutated, e.g. to reduce antigenicity, for example by removing B- and/or T-cell epitopes. Humanization is one example mode of sequence modification.

Kits

In one aspect, there is provided a kit for delivering a cargo polypeptide to a cell comprising the above-described recombinant molecule, and instructions for contacting the cell with the recombinant molecule.

In one aspect, there is provided a kit for delivering a cargo polypeptide to a cell of a subject, comprising the above-described recombinant molecule, and instructions for contacting the cell with the recombinant molecule.

In one aspect, there is provided a kit for delivering a cargo polypeptide across the blood brain barrier, comprising the above-described recombinant molecule, and instructions for administering the recombinant molecule to a subject.

In one aspect, there is provided a kit for increasing enzyme or protein activity in a cell, comprising the above-described recombinant molecule, and instructions for contacting the cell with the recombinant molecule.

In one aspect, there is provided a kit for alleviating enzyme or protein deficiency in a cell, comprising the above-described recombinant molecule, and instructions for contacting the cell with the recombinant molecule. In one embodiment, the cargo polypeptide comprises the enzyme or protein, or an active fragment thereof having substantially the same activity. In another embodiment, the cargo polypeptide compensates for the enzyme or protein deficiency.

In one aspect, there is provided a kit for treating a disease or disorder caused by enzyme or protein deficiency in a subject, comprising the above-described recombinant molecule, and instructions for administering the recombinant molecule to the subject. In one embodiment, the cargo polypeptide comprises the enzyme or protein, or an active fragment thereof having substantially the same activity. In another embodiment, the cargo polypeptide compensates for the enzyme or protein deficiency. The disease or disorder may be Rett syndrome, and the cargo polypeptide may comprise MecP2 (e.g. SEQ ID No: 16 or 17). The disease or disorder may be Spinal Muscular Atrophy syndrome, and the cargo polypeptide may comprise SMN (e.g. SEQ ID No: 19). The disease or disorder may be Fragile X syndrome, and the cargo polypeptide may comprise FMRP (e.g. SEQ ID No: 18). The disease or disorder may be PNP-deficiency, and the cargo polypeptide may comprise PNP (e.g. SEQ ID No: 24). The disease or disorder may be Lafora Disease, and the cargo polypeptide may comprise alpha-amylase (e.g. SEQ ID No: 15).

In one embodiment, the cargo protein comprises RRSP (Ras/Rap1-specific endopeptidase) from *Vibrio vulnificus*, a functional variant, or a homologue thereof. The RRSP may comprise SEQ ID NO: 27.

In the kits described herein, the cargo polypeptide may have a molecular weight of less than 10 kDa, greater than 10 kDa, greater than 20 kDa, greater than 30 kDa, greater than 50 kDa, greater than 100 kDa, or greater than 150 kDa.

In one aspect, there is provided a kit for manipulating the genome of cell, comprising the above-described recombinant molecule, and instructions for contacting the cell with the recombinant molecule, wherein the cargo polypeptide comprises a genome-modifying protein. Genome-modifying proteins for genetic engineering are widely known. The genome-modifying protein may be, for example, a zinc finger nuclease (ZFN), a transcription activator-like effector nuclease (TALEN), or a CRISPR clustered regularly interspaced short palindromic repeat) protein. For example, the CRISPR protein may be Cas9 (e.g. SEQ ID No: 22). In some embodiments, these nucleic acids, such as guide RNAs, may be separately delivered to cells. In others, a pre-complex of protein and nucleic acid may be formed for delivery into a cell.

For applications of the above kits involving subjects or therapy, a recombinant molecule comprising non-toxic, catalytically inactive DTA (dta) may be preferred. For example, a DTA having K51E and E148K mutations may be useful in such applications. A skilled person could generate and test other mutations, e.g. using cellular assays such as those described herein, to determine which have desirable properties in this regard. The DTA may comprise a sequence as set forth in SEQ ID No: 2. The DTA may comprise variants or modification of this sequence, such as those discussed above.

For some therapeutic applications, it may be desirable to reduce the antigenicity of the fusion protein or the DT domains. They may be accomplished in a number of ways. For example, an amino acid sequence could be PEGylated. The amino acid sequence may also be mutated, e.g. to reduce antigenicity, for example by removing B- and/or T-cell epitopes. Humanization is one example mode of sequence modification.

Example 1

Generation of Cargo-DT Chimera

DT plasmid carrying the E148S mutation was a gift Dr. R. John Collier (Harvard Medical School, Boston, Mass.). Point mutations were made in the DT E148S plasmid using QuikChange™ lightning multi-mutagenesis kit (Agilent Technologies) to prepare wt-DT (E148), catalytically inactive DT (K51E/E148K), and the pore-formation defective DT (L350K). Cargo proteins were fused to different DT variants using the In-Fusion™ HD Cloning Kits (Clontech).

As referred to herein, dtA refers to the wildtype DTA sequence, whereas dta refers to the DTA sequence containing the inactivating mutations K51E and E148K.

Various fluorescent fusion proteins were created as DT fusion proteins. Both enhanced green fluorescent protein (eGFP) and monomeric cherry (mCherry) proteins were used in various constructs. Both eGFP-dtA-dtB and mCherry-dtA-dtB were created. EGFP and dtA were linked via a GSG linker, while mCherry and dtA were linked via a (G4S)2 linker. Further, both eGFP and mCherry were created as dtA-eGFP-dta-dtB and dtA-mCherry-dta-dtB fusion proteins, where dta contains the inactivating mutations K51E and E148K. In both cases, the dtA and cargo are linked via a GSG linker, and cargo and dta are also linked via a GSG linker. Both eGFP and mCherry contain the mutation V1G to enhance cleavage by the SUMO protease during purification in all constructs except dtA-mCherry-dta-dtB, where first residue is the native valine.

The alpha-amylase enzyme from *Bacillus megaterium* was linked to dtA via a GSG linker. A mutation was made in the alpha-amylase sequence (V1G) to enhance cleavage by the SUMO protease for purification purposes. Another construct, dtA-Amylase-dta-dtB was also made. In this case, dtA is linked to amylase via a GSG linker, and amylase is linked to dta via a GSG linker.

Table 1 lists sequences of domains, linkers, and cargo.

TABLE 1

Diphtheria Toxin Sequences (Full-length DT = dtA-dtB; dtB = dtT + dtR)

| | SEQ ID | |
|---|---|---|
| dtA Domain | 1 | GADDVVDSSKSFVMENFSSYHGTKPGYVDSIQKGIQKPKSGTQGNYDDDWKGFYS TDNKYDAAGYSVDNENPLSGKAGGVVKVTYPGLTKVLALKVDNAETIKKELGLSL TEPLMEQVGTEEFIKRFGDGASRVVLSLPFAEGSSSVEYINNWEQAKALSVELEI NFETRGKRGQDAMYEYMAQACAGNRVRRSVGSSL |
| dta Domain (K51E, E148K) | 2 | GADDVVDSSKSFVMENFSSYHGTKPGYVDSIQKGIQKPKSGTQGNYDDDWEGFYS TDNKYDAAGYSVDNENPLSGKAGGVVKVTYPGLTKVLALKVDNAETIKKELGLSL |

TABLE 1-continued

| | | |
|---|---|---|
| | | TEPLMEQVGTEEFIKRFGDGASRVVLSLPFAEGSSSVKYINNWEQAKALSVELEI NFETRGKRGQDAMYEYMAQACAGNRVRRSVGSSL |
| dtB Domain | 3 | SCINLDWDVIRDKTKTKIESLKEHGPIKNKMSESPNKTVSEEKAKQYLEEFHQTA LEHPELSELKTVTGTNPVFAGANYAAWAVNVAQVIDSETADNLEKTTAALSILPG IGSVMGIADGAVHHNTEEIVAQSIALSSLMVAQAIPLVGELVDIGFAAYNFVESI INLFQVVHNSYNRPAYSPGHKTQPFLHDGYAVSWNTVEDSIIRTGFQGESGHDIK ITAENTPLPIAGVLLPTIPGKLDVNKSKTHISVNGRKIRMRCRAIDGDVTFCRPK SPVYVGNGVHANLHVAFHRSSSEKIHSNEISSDSIGVLGYQKTVDHTKVNSKLSL FFEIKSRQA |
| dtT (dtB Translocation Domain) | 4 | SCINLDWDVIRDKTKTKIESLKEHGPIKNKMSESPNKTVSEEKAKQYLEEFHQTA LEHPELSELKTVTGTNPVFAGANYAAWAVNVAQVIDSETADNLEKTTAALSILPG IGSVMGIADGAVHHNTEEIVAQSIALSSLMVAQAIPLVGELVDIGFAAYNFVESI INLFQVVHNSYNRP |
| Translocation-deficient dtT (L350K) | 5 | SCINLDWDVIRDKTKTKIESLKEHGPIKNKMSESPNKTVSEEKAKQYLEEFHQTA LEHPELSELKTVTGTNPVFAGANYAAWAVNVAQVIDSETADNLEKTTAALSILPG IGSVMGIADGAVHHNTEEIVAQSIALSSLMVAQAIPLVGEKVDIGFAAYNFVESI INLFQVVHNSYNRP |
| dtR (dtB Receptor-binding Domain) | 6 | AYSPGHKTQPFLHDGYAVSWNTVEDSIIRTGFQGESGHDIKITAENTPLPIAGVL LPTIPGKLDVNKSKTHISVNGRKIRMRCRAIDGDVTFCRPKSPVYVGNGVHANLH VAFHRSSSEKIHSNEISSDSIGVLGYQKTVDHTKVNSKLSLFFEIKSRQA |
| Δdta | 28 | CAGNRVRRSVGSSL |

| Tag and Linker Sequences | | |
|---|---|---|
| | SEQ ID | |
| Polyhistidine-SUMO | 7 | MGSSHHHHHHGSGLVPRGSASMSDSEVNQEAKPEVKPETHINLKVSDGSSE IFFKIKKTTPLRRLMEAFAKRQGKEMDSLRFLYDGIRIQADQTPEDLDMEDNDII EAHREQIGG |
| MYC | 8 | EQKLISEEDL |
| SV40 NLS | 9 | SPPKKKRKV |
| (G4S) linker | 10 | GGGGS |
| (G4S)$_2$ linker | 11 | GGGGSGGGGS |
| (G4S)$_3$ linker | 12 | GGGGSGGGGSGGGGS |
| GSG Linker | n/a | GSG |
| Strep Tag ™ II | 29 | LVPRGSAWSHPQFEK |

| Cargo Sequences | | |
|---|---|---|
| | SEQ ID | |
| Enhanced Green Fluorescent Protein (eGFP) | 13 | GSKGEELFTGVVPILVELDGDVNGHKFSVSGEGEGDATYGKLTLKFICTTGKLPV PWPTLVTTLTYGVQCFSRYPDHMKQHDFFKSAMPEGYVQERTIFFKDDGNYKTRA EVKFEGDTLVNRIELKGIDFKEDGNILGHKLEYNYNSHNVYIMADKQKNGIKVNF KIRHNIEDGSVQLADHYQQNTPIGDGPVLLPDNHYLSTQSALSKDPNEKRDHMVL LEFVTAAGITLGMDELYK |
| Monomeric Cherry (mCherry) | 14 | GSKGEEDNMAIIKEFMRFKVHMEGSVNGHEFEIEGEGEGRPYEGTQTAKLKVTKG GPLPFAWDILSPQFMYGSKAYVKHPADIPDYLKLSFPEGFKWERVMNFEDGGVVT VTQDSSLQDGEFIYKVKLRGTNFPSDGPVMQKKTMGWEASSERMYPEDGALKGEI KQRLKLKDGGHYDAEVKTTYKAKKPVQLPGAYNVNIKLDITSHNEDYTIVEQYER AEGRHSTGGMDELYK |
| α-amylase (B. megaterium) | 15 | GHKGKSPTADKNGVFYEVYVNSFYDANKDGHGDLKGLTQKLDYLNDGNSHTKNDL QVNGIWMMPVNPSPSYHKYDVTDYYNIDPQYGNLQDFRKLMKEADKRDVKVIMDL VVNHTSSEHPWFQAALKDKNSKYRDYYIWADKNTDLNEKGSWGQQVWHKAPNGEY FYGTFWEGMPDLNYDNPEVRKEMINVGKFWLNQGVDGFRLDAALHIFKGQTPEGA KKNILWWNEFRDAMKKENPNVYLTGEVWDQPEVVAPYYQSLDSLFNFDLAGKIVS SVKAGNDQGIATAAAATDELFKSYNPNKIDGIFLTNHDQNRVMSELSGDVNKAKS AASILLTLPGNPYIYYGEEIGMTGEKPDELIREPFRWYEGNGLGQTSWETPIYNK GGNGVSIEAQTKQKDSLLNHYREMIRVRQQHEELVKGTLQSISLDQKEVVAYSRT YKGKSISVYHNISNQPIKVSVAAKGKLIFSSEKGVKKVKNQLVIPANTTILIK |
| MeCP2 (e1 isoform) | 16 | AAAAAAAAPSGGGGGGEEERLEEKSEDQDLQGLKDKPLKFKKVKKDKKEEKEGKHE PVQPSAHHSAEPAEAGKAETSEGSGSAPAVPEASASPKQRRSIIRDGRPMYDDPT LPEGWTRKLKQRKSGRSAGKYDVYLINPQGKAFRSKVELIAYFEKVGDTSLDPND FDFTVTGRGSPSRREQKPPKKPKSPKAPGTGRGRGRPKGSGTTRPKAATSEGVQV KRVLEKSPGKLLVKMPFQTSPGGKAEGGGATTSTQVMVIKRPGRKRKAEADPQAI |

TABLE 1-continued

| | | |
|---|---|---|
| | | PKKRGRKPGSVVAAAAAEAKKKAVKESSIRSVQETVLPIKKRKTRETVSIEVKEV<br>VKPLLVSTLGEKSGKGLKTCKSPGRKSKESSPKGRSSSASSPPKKEHHHHHHSE<br>SPKAPVPLLPPLPPPPPEPESSEDPTSPPEPQDLSSSVCKEEKMPRGGSLESDGC<br>PKEPAKTQPAVATAATAAEKYKHRGEGERKDIVSSSMPRPNREEPVDSRTPVTER<br>VS |
| MeCP2 (e2 isoform) | 17 | VAGMLGLREEKSEDQDLQGLKDKPLKFKKVKKDKKEEKEGKHEPVQPSAHHSAEP<br>AEAGKAETSEGSGSAPAVPEASASPKQRRSIIRDRGPMYDDPTLPEGWTRKLKQR<br>KSGRSAGKYDVYLINPQGKAFRSKVELIAYFEKVGDTSLDPNDFDFTVTGRGSPS<br>RREQKPPKKPKSPKAPGTGRGRGRPKGSGTTRPKAATSEGVQVKRVLEKSPGKLL<br>VKMPFQTSPGGKAEGGGATTSTQVMVIKRPGRKRKAEADPQAIPKKRGRKPGSVV<br>AAAAAEAKKKAVKESSIRSVQETVLPIKKRKTRETVSIEVKEVVKPLLVSTLGEK<br>SGKGLKTCKSPGRKSKESSPKGRSSSASSPPKKEHHHHHHSESPKAPVPLLPPL<br>PPPPPEPESSEDPTSPPEPQDLSSSVCKEEKMPRGGSLESDGCPKEPAKTQPAVA<br>TAATAAEKYKHRGEGERKDIVSSSMPRPNREEPVDSRTPVTERVS |
| FMRP | 18 | EELVVEVRGSNGAFYKAFVKDVHEDSITVAFENNWQPDRQIPFHDVRFPPPVGYN<br>KDINESDEVEVYSRANEKEPCCWWLAKVRMIKGEFYVIEYAACDATYNEIVTIER<br>LRSVNPNKPATKDTFHKIKLDVPEDLRQMCAKEAAHKDFKKAVGAFSVTYDPENY<br>QLVILSINEVTSKRAHMLIDMHFRSLRTKLSLIMRNEEASKQLESSRQLASRFHE<br>QFIVREDLMGLAIGTHGANIQQARKVPGVTAIDLDEDTCTFHIYGEDQDAVKKAR<br>SFLEFAEDVIQVPRNLVGKVIGKNGKLIQEIVDKSGVVRVRIEAENEKNVPQEEE<br>IMPPNSLPSNNSRVGPNAPEEKKHLDIKENSTHFSQPNSTKVQRGMVPFVFVGTK<br>DSIANATVLLDYHLNYLKEVDQLRLERLQIDEQLRQIGASSRPPPNRTDKEKSYV<br>TDDGQGMGRGSRPYRNRGHGRRGPGYTSAPTEEERESFLRRGDGRRRGGGGRGQG<br>GRGRGGGFKGNDDHSRTDNRPRNPREAKGRTTDGSLQIRVDCNNERSVHTKTLQN<br>TSSEGSRLRTGKDRNQKKEKPDSVDGQQPLVNGVP |
| SMN | 19 | MAMSSGGSGGGVPEQEDSVLFRRGTGQSDDSDIWDDTALIKAYDKAVASFKHALK<br>NGDICETSGKPKTTPKRKPAKKNKSQKKNTAASLQQWKVGDKCSAIWSEDGCIYP<br>ATIASIDFKRETCVVVYTGYGNREEQNLSDLLSPICEVANNIEQNAQENENESQV<br>STDESENSRSPGNKSDNIKPKSAPWNSFLPPPPPMPGPRLGPGKPGLKFNGPPPP<br>PPPPPPHLLSCWLPPFFSGPPIIPPPPPICPDSLDDADALGSMLISWYMSGYHTG<br>YYMGFRQNQKEGRCSHSIN |
| CPD (C. difficile) | 20 | EGSLGEDDNLDFSQNIVVDKEYLLEKISSLARSSERGYIHYIVQLQGDKISYEAA<br>CNLFAKTPYDSVLFQKNIEDSEIAYYYNPGDGEIQEIDKYKIPSIISDRPKIKLT<br>FIGHGKDEFNTDIFAGFDVDSLSTEIEAAIDLAKEDISPKSIEINLLGCNMFSYS<br>INVEETYPGKLLLKVKDKISELMPSISQDSIIVSANQYEVRINSEGRRELLDHSG<br>EWINKEESIIKDISSKEYISFNPKENKITVKSKNLPELSTL |
| CPD (V. cholera) | 21 | KEALADGKILHNQVNSWGPITVTPTTDGGETRFDGQIIVQMENDPVVAKAAANL<br>AGKHAESSVVVQLDSDGNYRVVYGDPSKLDGKLRWQLVGHGRDHSETNNTRLSGY<br>SADELAVKLAKFQQSFNQAENINNKPDHISIVGCSLVSDDKQKGFGHQFINAMDA<br>NGLRVDVSVRSSELAVDEAGRKHTKDANGDWVQKAENNKVSLSWDAQ |
| Cas9 (S. pyogenes) | 22 | MDKKYSIGLDIGTNSVGWAVITDDYKVPSKKFKVLGNTDRHSIKKNLIGALLFGS<br>GETAEATRLKRTARRRYTRRKNRICYLQEIFSNEMAKVDDSFFHRLEESFLVEED<br>KKHERHPIFGNIVDEVAYHEKYPTIYHLRKKLADSTDKADLRLIYLALAHMIKFR<br>GHFLIEGDLNPDNSDVDKLFIQLVQIYNQLFEENPINASRVDAKAILSARLSKSR<br>RLENLIAQLPGEKRNGLFGNLIALSLGLTPNFKSNFDLAEDAKLQLSKDTYDDDL<br>DNLLAQIGDQYADLFLAAKNLSDAILLSDILRVNSEITKAPLSASMIKRYDEHHQ<br>DLTLLKALVRQQLPEKYKEIFFDQSKNGYAGYIDGGASQEEFYKFIKPILEKMDG<br>TEELLVKLNREDLLRKQRTFDNGSIPHQIHLGELHAILRRQEDFYPFLKDNREKI<br>EKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVD<br>LLFKTNRKVTVKQLKEDYFKKIECFDSVEISGVEDRFNASLGAYHDLLKIIKDKD<br>FLDNEENEDILEDIVLTLTLFEDRGMIEERLKTYAHLFDDKVMKQLKRRRYTGWG<br>RLSRKLINGIRDKQSGKTILDFLKSDGFANRNFMQLIHDDSLTFKEDIQKAQVSG<br>QGHSLHEQIANLAGSPAIKKGILQTVKIVDELVKVMGHKPENIVIEMARENQTTQ<br>KGQKNSRERMKRIEEGIKELGSQILKEHPVENTQLQNEKLYLYYLQNGRDMYVDQ<br>ELDINRLSDYDVDHIVPQSFIKDDSIDNKVLTRSDKNRGKSDNVPSEEVVKKMKN<br>YWRQLLNAKLITQRKFDNLTKAERGGLSELDKAGFIKRQLVETRQITKHVAQILD<br>SRMNTKYDENDKLIREVKVITLKSKLVSDFRKDFQFYKVREINNYHHAHDAYLNA<br>VVGTALIKKYPKLESEFVYGDYKVYDVRKMIAKSEQEIGKATAKYFFYSNIMNFF<br>KTEITLANGEIRKRPLIETNGETGEIVWDKGRDFATVRKVLSMPQVNIVKKTEVQ<br>TGGFSKESILPKRNSDKLIARKKDWDPKKYGGFDSPTVAYSVLVVAKVEKGKSKK<br>LKSVKELLGITIMERSSFEKNPIDFLEAKGYKEVKKDLIIKLPKYSLFELENGRK<br>RMLASAGELQKGNELALPSKYVNFLYLASHYEKLKGSPEDNEQKQLFVEQHKHYL<br>DEIIEQISEFSKRVILADANLDKVLSAYNKHRDKPIREQAENIIHLFTLTNLGAP<br>AAFKYFDTTIDRKRYTSTKEVLDATLIHQSITGLYETRIDLSQLGGDSPVR |
| Cas9 (S. pyogenes) with N-terminal His, SV40 and C-terminal SV40 sequences | 23 | HHHHHHGSGATMASPPKKKRKVGSMDKKYSIGLDIGTNSVGWAVITDDYKVPSKK<br>FKVLGNTDRHSIKKNLIGALLFGSGETAEATRLKRTARRRYTRRKNRICYLQEIF<br>SNEMAKVDDSFFHRLEESFLVEEDKKHERHPIFGNIVDEVAYHEKYPTIYHLRKK<br>LADSTDKADLRLIYLALAHMIKFRGHFLIEGDLNPDNSDVDKLFIQLVQIYNQLF<br>EENPINASRVDAKAILSARLSKSRRLENLIAQLPGEKRNGLFGNLIALSLGLTPN<br>FKSNFDLAEDAKLQLSKDTYDDDLDNLLAQIGDQYADLFLAAKNLSDAILLSDIL<br>RVNSEITKAPLSASMIKRYDEHHQDLTLLKALVRQQLPEKYKEIFFDQSKNGYAG<br>YIDGGASQEEFYKFIKPILEKMDGTEELLVKLNREDLLRKQRTFDNGSIPHQIHL |

TABLE 1-continued

| | | |
|---|---|---|
| | | GELHAILRRQEDFYPFLKDNREKIEKILTFRIPYYVGPLARGNSRFAWMTRKSEE<br>TITPWNFEEVVDKGASAQSFIERMTNFDKNLPNEKVLPKHSLLYEYFTVYNELTK<br>VKYVTEGMRKPAFLSGEQKKAIVDLLFKTNRKVTVKQLKEDYFKKIECFDSVEIS<br>GVEDRFNASLGAYHDLLKIIKDKDFLDNEENEDILEDIVLTLTLFEDRGMIEERL<br>KTYAHLFDDKVMKQLKRRRYTGWGRLSRKLINGIRDKQSGKTILDFLKSDGFANR<br>NFMQLIHDDSLTFKEDIQKAQVSGQGHSLHEQIANLAGSPAIKKGILQTVKIVDE<br>LVKVMGHKPENIVIEMARENQTTQKGQKNSRERMKRIEEGIKELGSQILKEHPVE<br>NTQLQNEKLYLYYLQNGRDMYVDQELDINRLSDYDVDHIVPQSFIKDDSIDNKVL<br>TRSDKNRGKSDNVPSEEVVKKMKNYWRQLLNAKLITQRKFDNLTKAERGGLSELD<br>KAGFIKRQLVETRQITKHVAQILDSRMNTKYDENDKLIREVKVITLKSKLVSDFR<br>KDFQFYKVREINNYHHAHDAYLNAVVGTALIKKYPKLESEFVYGDYKVYDVRKMI<br>AKSEQEIGKATAKYFFYSNIMNFFKTEITLANGEIRKRPLIETNGETGEIVWDKG<br>RDFATVRKVLSMPQVNIVKKTEVQTGGFSKESILPKRNSDKLIARKKDWDPKKYG<br>GFDSPTVAYSVLVVAKVEKGKSKKLKSVKELLGITIMERSSFEKNPIDFLEAKGY<br>KEVKKDLIIKLPKYSLFELENGRKRMLASAGELQKGNELALPSKYVNFLYLASHY<br>EKLKGSPEDNEQKQLFVEQHKHYLDEIIEQISEFSKRVILADANLDKVLSAYNKH<br>RDKPIREQAENIIHLFTLTNLGAPAAFKYFDTTIDRKRYTSTKEVLDATLIHQSI<br>TGLYETRIDLSQLGGDSPVRSPKKKRKV |
| PNP | 24 | MENGYTYEDYKNTAEWLLSHTKHRPQVAIICGSGLGGLTDKLTQAQIFDYSEIPN<br>FPPRSTVPGHAGRLVFGFLNGRACVMMQGRFHMYEGYPLWKVTFPVRVFHLLGVDT<br>LVVTNAAGGLNPKFEVGDIMLIRDHINLPGFSGQNPLRGPNDERFGDRFPAMSDA<br>YDRTMRQRALSTWKQMGEQRELQEGTYVMVAGPSFETVAECRVLQKLGADAVGMS<br>TVPEVIVARHCGLRVFGFSLITNKVIMDYESLEKANHEEVLAAGKQAAQKLEQFV<br>SILMASIPLPDKAS |
| SUMO | 25 | MSDSEVNQEAKPEVKPEVKPETHINLKVSDGSSEIFFKIKKTTPLRRLMEAFAKR<br>QGKEMDSLRFLYDGIRIQADQTPEDLDMEDNDIIEAHREQIGG |
| GTD | 30 | MSLVNRKQLEKMANVRFRTQEDEYVAILDALEEYHNMSENTVVEKYLKLKDINSL<br>TDIYIDTYKKSGRNKALKKFKEYLVTEVLELKNNNLTPVEKNLHFVWIGGQINDT<br>AINYINQWKDVNSDYNVNVFYDSNAFLINTLKKTVVESAINDTLESFRENLNDPR<br>FDYNKFFRKRMEIIYDKQKNFINYYKAQREENPELTIDDIVKTYLSNEYSKEIDE<br>LNTYIEESLNKITQNSGNDVRNFEEFKNGESFNLYEQELVERWNLAAASDILRIS<br>ALKEIGGMYLDVDMLPGIQPDLFESIEKPSSVTVDFWEMTKLEAIMKYKEYIPEY<br>TSEHFDMLDEEVQSSFESVLASKSDKSEIFSSLGDMEASPLEVKIAFNSKGIINQ<br>GLISVKDSYCSNLIVKQIENRYKILNNSLNPAISEDNDFNTTTNTFIDSIMAEAN<br>ADNGRFMMELGKYLRVGFFPDVKTTINLSGPEAYAAAYQDLLMFKEGSMNIHLIE<br>ADLRNFEISKTNISQSTEQEMASLWSFDDARAKAQFEEYKRNYFEGSL |
| RRSP (DNA) | 26 | GGTGATAAAACCAAGGTCGTGGTCGATTTAGCGCAAATCTTTACGGTGCAAGAGC<br>TGAAAAGAAAGAGCAAAAGTTTTTGCTAAACCGATTGGCGCATCCTACCAAGGTAT<br>TCTCGATCAACTCGACCTTGTGCATCAGGCTAAAGGCCGCGATCAAATCGCAGCG<br>AGCTTTGAGCTTAATAAGAAGATTAATGACTACATCGCTGAACATCCAACTTCGG<br>GGCGTAATCAAGCGCTAACGCAGTTGAAAGAGCAGGTCACCAGTGCGTTGTTTAT<br>CGGTAAGATGCAAGTTGCCCAAGCGGGTATTGATGCAATCGCACAAACAAGACCG<br>GAGCTTGCCGCTCGTATCTTTATGGTCGCGATTGAAGAAGCCAACGGTAAACACG<br>TAGGTTTGACGGACATGATGGTTCGTTGGGCAATGAAGACCCATACTTGGCACC<br>GAAGCATGGTTACAAAGGCGAAACGCCAAGTGACCTTGGTTTTGATGCGAAGTAC<br>CACGTAGATCTAGGTGAGCATTACGCTGATTTCAAACAGTGGTTAGAAACGTCCC<br>AGTCGAACGGGTTGTTGAGTAAAGCGACGTTGGATGAATCCACTAAAACGGTTCA<br>TCTTGGCTATAGCTATCAAGAACTTCAGGATTTGACGGGTGCTGAATCGGTGCAA<br>ATGGCGTTCTACTTCCTGAAAGAAGCGGCGAAGAAAGCGGATCCGATTTCTGGTG<br>ATTCAGCTGAAATGATACTGCTGAAGAAATTTGCAGATCAAAGCTACTTATCTCA<br>ACTTGATTCCGACCGAATGGATCAAATTGAAGGTATCTACCGCAGTAGCCATGAG<br>ACGGATATTGACGCTTGGGATCGTCGTTACTCTGGTACAGGCTATGATGAGCTGA<br>CGAATAAGCTTGCTAGTGCAACGGGCGTTGACGAGCAGCTTGCGGTTCTTCTGGA<br>TGATCGTAAAGGCCTCTTGATTGGTGAAGTGCATGGCAGCGACGTCAACGGCCTA<br>CGCTTTGTTAATGAACAGATGGATGCACTGAAAAAACAGGGAGTCACAGTCATTG<br>GCCTTGAGCATTTACGCTCAGACCTTGCGCAACCGCTGATTGATCGCTACCTAGC<br>TACGGGTGTGATGTCGAGTGAACTAAGCGCAATGCTGAAAACAAAGCATCTCGAT<br>GTCACTCTTTTTGAAAACGCACGTGCTAACGGTATGCGCATCGTCGCGCTGGATG<br>CAAACAGCTCTGCGCGTCCAAATGTTCAGGGAACAGAACATGGTCTGATGTACCG<br>TGCTGGTGCTGCGAACAACATTGCGGTGGAAGTATTACAAAATCTGCCTGATGGC<br>GAAAAGTTCGTTGCTATCTACGGTAAAGCGCATTTGCAGTCTCACAAAGGGATTG<br>AAGGGTTCGTTCCTGGTATCACGCACCGTCTCGATCTTCCTGCGCTTAAAGTCAG<br>TGACTCGAACCAGTTCACAGTTGAACAAGACGATGTAAGTCTACGTGTTGTCTAC<br>GATGATGTTGCTAACAAACCGAAGATCACGTTCAAGGGCAGTTTG |
| RRSP (amino acid) | 27 | GDKTKVVVDLAQIFTVQELKERAKVFAKPIGASYQGILDQLDLVHQAKGRDQIAA<br>SFELNKKINDYIAEHPTSGRNQALTQLKEQVTSALFIGKMQVAQAGIDAIAQTRP<br>ELAARIFMVAIEEANGKHVGLTDMMVRWANEDPYLAPKHGYKGETPSDLGFDAKY<br>HVDLGEHYADFKQWLETSQSNGLLSKATLDESTKTVHLGYSYQELQDLTGAESVQ<br>MAFYFLKEAAKKADPISGDSAEMILLKKFADQSYLSQLDSDRMDQIEGIYRSSHE<br>TDIDAWDRRYSGTGYDELTNKLASATGVDEQLAVLLDDRKGLLIGEVHGSDVNGL<br>RFVNEQMDALKKQGVTVIGLEHLRSDLAQPLIDRYLATGVMSSELSAMLKTKHLD<br>VTLFENARANGMRIVALDANSSARPNVQGTEHGLMYRAGAANNIAVEVLQNLPDG<br>EKFVAIYGKAHLQSHKGIEGFVPGITHRLDLPALKVSDSNQFTVEQDDVSLRVVY<br>DDVANKPKITFKGSL |

Table 2 contains a non-exhaustive list of constructs generated and tested in ensuing Examples.

TABLE 2

| Cargo family | Delivered cargo | Cargo MW (kDa) |
|---|---|---|
| DT-based | (wildtype) = dtA | 21 |
| | (K51E/E148K) = dta | 22 |
| | (L350K) = dtb | 21 |
| | dtA alone | 21 |
| Sumo-based | Sumo-dtA | 35 |
| eGFP-based | eGFP-dtA | 49 |
| | eGFP-(G4S)1-dtA | 49 |
| | eGFP-(G4S)2-dtA | 49 |
| | eGFP-(G4S)3-dtA | 49 |
| | dtA-eGFP-dta | 71 |
| | dta-eGFP-dtA | 71 |
| | Sumo-eGFP-dtA | 62 |
| | Sumo-dtA-eGFP-dta | 84 |
| | dtA-eGFP-dtA-dtb | 71 |
| mCherry-based | mCherry-dtA | 48 |
| | dtA-mCherry-dta | 70 |
| | Sumo-dtA-mCherry-dta | 83 |
| Ubiquitin-based | Sumo-Ub-dtA | 43 |
| | Sumo-Ub-eGFP-dtA | 70 |
| | Sumo-Ub-dtA-eGFP-dta | 92 |
| α-amylase-based | α-amylase-dtA | 78 |
| | dtA-α-amylase-dta | 100 |
| | Sumo-dtA-α-amylase-dta | 113 |
| | α-amylase-dta | 78 |
| | α-amylase | 57 |
| TAT-based | TAT-dta | 21 |
| | dta-TAT | 21 |

Example 2

Expression and Purification of Recombinant Diphtheria Toxin (DT)

Recombinant DT and cargo-DT chimeras were expressed as N-terminal His-tagged proteins in *E. coli* BL21(DE3) cells, induced with 1 mM isopropyl-β-d-1-thiogalactopyranoside (IPTG) for 4 hours at 37° C. (DT) or 21° C. (cargo-DT), using the Champion™ pet-SUMO expression system (Invitrogen). Cells were harvested by centrifugation, re-suspended in lysis buffer (20 mM Tris-HCl pH 8.0, 0.5 M NaCl, 20 mM imidazole, benzonase, lysozyme and Protease inhibitor cocktail) and lysed by an EmulsiFlex C3 microfluidizer (Avestin) at 15,000 psi. The lysates were centrifuged at 18,000×g for 20 minutes. His-Sumo-tagged proteins were purified by Ni-affinity chromatography using a His-Trap FF column (GE-Healthcare). After purification, the His-Sumo tag was removed by adding 1 U of Sumo protease (Life Sensor) to 90 μg of purified protein in 20 mM Tris-HCl pH 8.0 containing 150 mM NaCl and 2 mM DTT. The cleavage reaction mixture was incubated at 30° C. for 1 hour followed by purification using His-Pure™ Ni-NTA resin (Thermo Scientific) to remove the His-Sumo protease and His-Sumo tag from the purified DT and cargo-DT samples.

Example 3

Cellular DTA Intoxication Assay

Protein synthesis inhibition was used to measure the ability of DT and cargo-DT chimera to deliver DTA to the cytosol. VERO cells (6,000 cells per well in a 96 well plate) were exposed to 3-fold serial dilutions of DT or cargo-DT. The cells were incubated with the toxin overnight (17 hours) at 37° C. The next day, toxin-containing medium was removed, and the cells were incubated for 2 hours at 37° C. in leucine-deficient medium supplemented with 1 μCi of [$^3$H]leucine/ml (PerkinElmer). The cells were washed twice with cold phosphate-buffered saline (PBS) before precipitation of cellular protein with 10% trichloroacetic acid (TCA). Protein synthesis was measured by the amount of [$^3$H]leucine incorporated into total cellular protein, as determined by scintillation counting with a TopCount NXT™ (Perkin Elmer). Percent protein synthesis was plotted versus the log concentration of DT or cargo-DT. Protein synthesis kinetic experiments were performed as described above except that the toxin concentration was fixed at 1 nM and the toxin was exposed to cells for 1, 2, 3, 4, 5 or 17 hrs. Protein synthesis competition experiments were performed as described above but a fixed concentration (1 nM) of a non-toxic variant of DT (a-B or DT_K51E/E148K) was also added to cells to compete with the toxic DT variant (A-EGFP-a-B) which was added to cells using a 3-fold serial dilution pattern (starting concentration 1 nM).

Example 4

Real-Time Protein Unfolding Using Differential Scanning Fluorimetry

Purified eGFP (40 ng) and mCherry (7 μg) (20 mM Tris-HCl, 150 mM NaCl, pH8.0) were diluted in citrate-phosphate buffer at pH's that ranged from 3.6 to 7.6 in a 96-well PCR plate. The proteins at various pH's were placed in a Real-Time PCR Detection System (BioRad CFX96™) to measure protein unfolding. Intrinsic fluorescence of eGFP (494-519 nm) and mCherry (595-613 nm) were captured over a wide range of temperature (15 to 95° C.). The melting temperatures of eGFP and mCherry were calculated by the software provided with the detection system (Bio-Rad CFX Manager™ 3.1).

Example 5

Amylase Delivery of Intracellular Glycogen 24 h prior to treatment HEK293 cells were seeded on 6-well plates (BD amine coated) at 0.5×$10^6$ (for 24 h incubation) or 0.25×$10^6$ (for 48 h incubation) cells per well and cultivated at 37° C. and 5% $CO_2$ in DMEM (10% FBS, 1% Penicillin/Streptomycin). For treatment the medium was changed, the new medium containing additionally 0.1 or 1.0 uM of DT, DT-amylase, or amylase protein. After incubation as indicated for harvesting cells were put on ice, washed once with ice-cold PBS, and in a cold room (4° C.) transferred to 1.5 mL vials subsequent to scraping and re-suspending them in 1 mL ice-cold PBS. The cells, being henceforth kept on ice or at 4° C., were pelleted, the supernatant being removed. After washing the cells again with 1 mL PBS the cell sample was split for separate glycogen and protein determination.

For glycogen determination cells were incubated for 45 min in 0.5 M KOH at 98° C. with intermittent mixing to lyse cells and extract glycogen. Following neutralization with 2 M acetic acid glycogen was digested in an aliquot overnight at 55° C. with 0.5 U amyloglucosidase (Sigma) and subsequently determined as free glucose according to Lowry, O.H. and J.V. Passonneau (1972) *A Flexible System of Enzymatic Analysis. New York, New York: Academic Press*, with an enzymatic assay that detects NADPH by incubating the sample with hexokinase (Roche), glucose 6-phosphate dehydrogenase (Roche), ATP (Sigma), and NADP (Roche). Glucose in undigested extracts was consistently below the limit of detection.

For glycogen determination cells were incubated for 45 min in 0.5 M KOH at 98° C. with intermittent mixing to lyse cells and extract glycogen. Following neutralization with 2 M acetic acid glycogen was digested in an aliquot overnight at 55° C. with 0.5 U amyloglucosidase (Sigma) and subsequently determined as free glucose according to Lowry and Passonneau (1972) with an enzymatic assay that detects NADPH by incubating the sample with hexokinase (Roche), glucose 6-phosphate dehydrogenase (Roche), ATP (Sigma), and NADP (Roche). Glucose in undigested extracts was consistently below the limit of detection.

Glycogen was based on protein levels to account for cell loss or growth variances due to treatment. Protein-based glycogen levels were normalized to controls treated with identical amounts of either DT or amylase protein (as indicated). Significance was tested using a T-test (two-tailed, homoscedastic since variances between sample populations were not significantly different). Significance levels: $0.05 > p \geq 0.01$ (*), $0.01 > p \geq 0.001$ (), $p < 0.001$ (*).

Example 6

Amino-Terminal Protein Fusions Dramatically Decrease the Apparent Cytotoxicity of DT To evaluate the ability of the diphtheria toxin translocation apparatus to co-deliver proteins into mammalian cells, a series of model passenger proteins were cloned, in accordance with Example 1, as amino terminal fusions to DT with an intervening Gly-Ser-Gly linker.

FIG. 1 depicts these constructs. Initially, three distinct passenger proteins were chosen, spanning a range of sizes, structures and physical properties with which to evaluate intracellular delivery: the 13-kDa globular Small Ubiquitin-like Modifier (SUMO; PDB: 3pge) protein; the 27-kDa enhanced green fluorescent protein (eGFP; PDB: 1gfl); and the 57-kDa α-amylase enzyme from *B. megaterium* (in FIG. 1, the structure of alpha-amylase of *H. orenni*—PDB: 1wza—Is shown an example structure from the alpha-amylase family). The proteins were fused to DT via a GSG linker. These constructs were expressed and purified in accordance with Example 2. To quantify delivery of the chimeric constructs to the cytosol, the intracellular action of the co-delivered A-chain of DT (dtA), which catalyzes the ADP-ribosylation of EF-2 and inhibits protein synthesis i.e., incorporation of $^3$H-Leu in the cellular proteome), was measured over a 2 h period in VERO cells that had been treated overnight with the chimeric toxins, in general accordance with Example 3.

Figure 2:
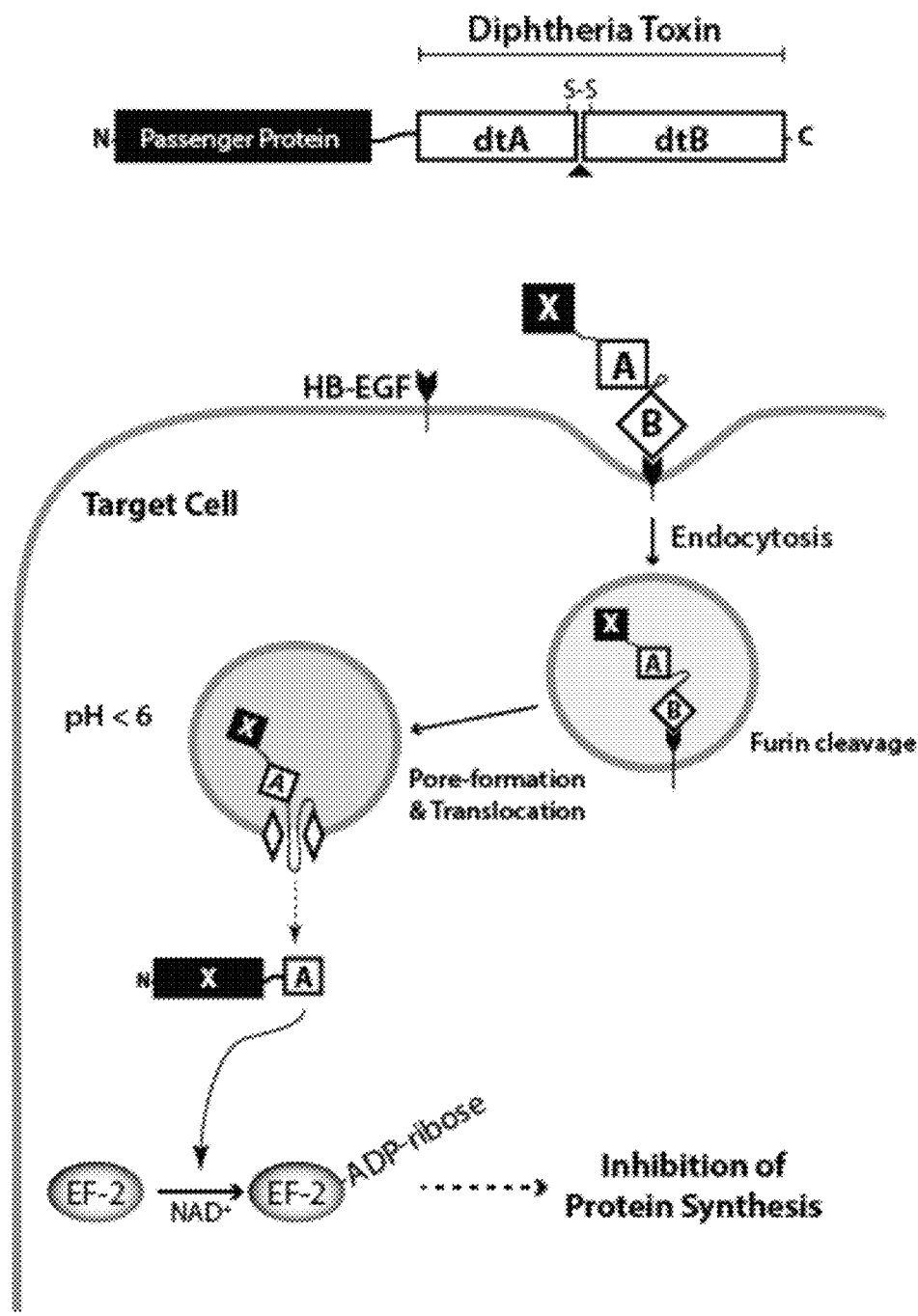
FIG. 2 depicts a schematic of first generation chimeric fusions of different passenger proteins to the amino terminus of native diphtheria toxin (DT) via a flexible GSG linker. 'A' represents a catalytically active diphtheria toxin enzymatic fragment (elsewhere termed 'dtA'). 'B' represents a functional the diphtheria toxin translocation fragment (elsewhere termed 'dtB').

FIG. 2 depicts a schematic of first generation chimeric fusions of different passenger proteins to the amino terminus of native diphtheria toxin (DT) via a flexible GSG linker. The enzymatic A domain (dtA) and translocation/receptor-binding B domain (dtB) have an intervening furin-like recognition site (black triangle) and are further joined by an intra-molecular disulfide bond. DT is internalized into endocytic vesicles by a receptor-mediated process. Within endosomes, a membrane-bound furin-like protease cleaves between dtA and dtB. Upon vesicular acidification, dtB undergoes a major conformational change, resulting in the formation of a membrane-spanning pore. dtA (and any associated passenger proteins) would then translocate into the cytosol starting with dtA, followed by any amino-terminal passenger proteins. Once in the cytosol, the dtA fragment catalyzes ADP-ribosylation of EF-2, resulting in the inhibition of protein synthesis. This straightforward measure of delivery is well established and provides a universal readout of delivery across different studies and different passenger proteins.

Figure 3:
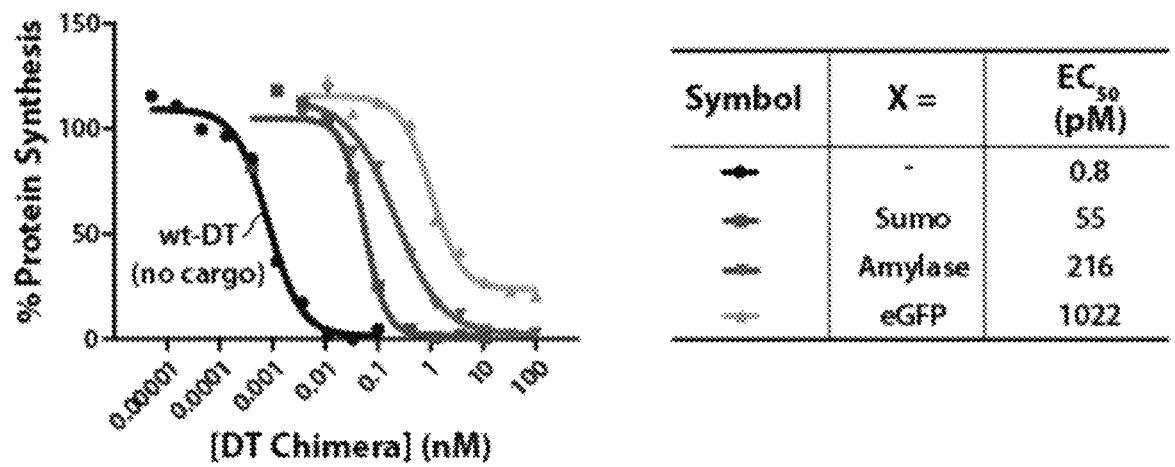
FIG. 3 depicts dose titration curves of chimeric constructs on cells with wt-DT, Sumo-DT, Amylase-DT, and eGFP-DT.

FIG. 3 depicts dose titration curves of chimeric constructs on cells with wt-DT, Sumo-DT, Amylase-DT, and eGFP-DT ($EC_{50}$ values are at the right), and shows that, in the absence of passenger proteins, (i.e. wildtype DT), protein synthesis was dose-dependently inhibited with an $EC_{50}=1.3 \pm 0.7$ pM. FIG. 3 further shows that, when Sumo, eGFP and α-amylase fusions were tested for intracellular delivery, protein synthesis was dose-dependently inhibited in all cases indicating that passenger proteins were delivered into the cytosol. Comparing the doses at which protein synthesis was inhibited by 50% ($EC_{50}$) for each chimera however, revealed significant shifts in their relative abilities to inhibit protein synthesis: 65-fold for Sumo; 260-fold for α-amylase; and 1200-fold for eGFP. These shifts, which are consistent with what has been observed previously with smaller cargo[4,6,7,9], suggest that passenger proteins disrupt the natural process of cellular intoxication somehow. Two fundamentally linked questions remain: at what exact step do passenger proteins disrupt intoxication; and, do these observed shifts directly correspond to reduced efficiency of intracellular delivery by DT.

It was hypothesized that the observed decreases in apparent potency might be due to the cargo differentially affecting the intracellular enzymatic activity of dtA after the chimeras had already entered the cytosol, rather than due to affecting upstream phenomena such as receptor binding or translocation per se. Support for this hypothesis came from a set of experiments that had been designed to investigate the effect of increasing the linker size between Cargo and dtA on expression and stability.

Figure 4:
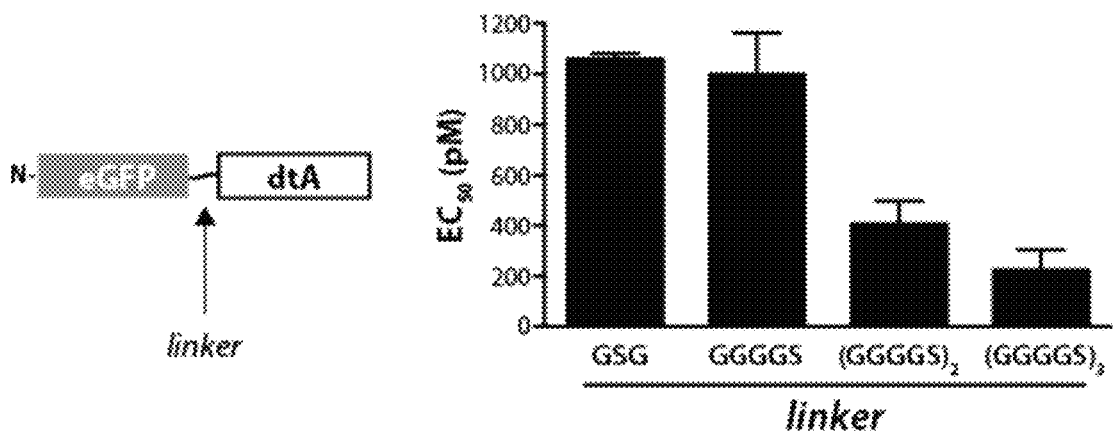
FIG. 4 depicts data evaluating the effect of linker size between eGFP and dtA on cells. 'dtA' represents a catalytically active diphtheria toxin enzymatic fragment.

FIG. 4 shows the effect of linker size between eGFP and dtA on cells, with error bars, SD (n=2). The consequent effects on the potency of inhibition of protein synthesis for each construct are shown on the right. With eGFP as the passenger protein, increasing the linker size GSG to GGGGS $G_4S$) to $(G_4S_2)_2$ to $(G_4S)_3$, resulted in increases in potency on cells, consistent with the idea that the passenger protein was affecting a step other than translocation.

Example 7

Passenger Proteins are 'Invisible' to the Translocation Machinery of DT

To explore the hypothesis that the passenger cargo was indirectly impacting dtA by proximity effects in a more direct way, a new construct was generated per Example 1 in which the active dtA reporter was placed upstream of eGFP (with a free amino terminus as it is in the WT toxin). The existing dtA attached to dtB was rendered catalytically inactive by the double mutation, $K_{51}E/E_{148}K^{10}$, signified as dta, to yield the final construct: dtA-eGFP-dta-dtB; or for simplification: A-eGFP-a-B. Cellular assays were carried out per Example 3 to study positional effects of passenger proteins on dtA activity in cells.

Figure 5:
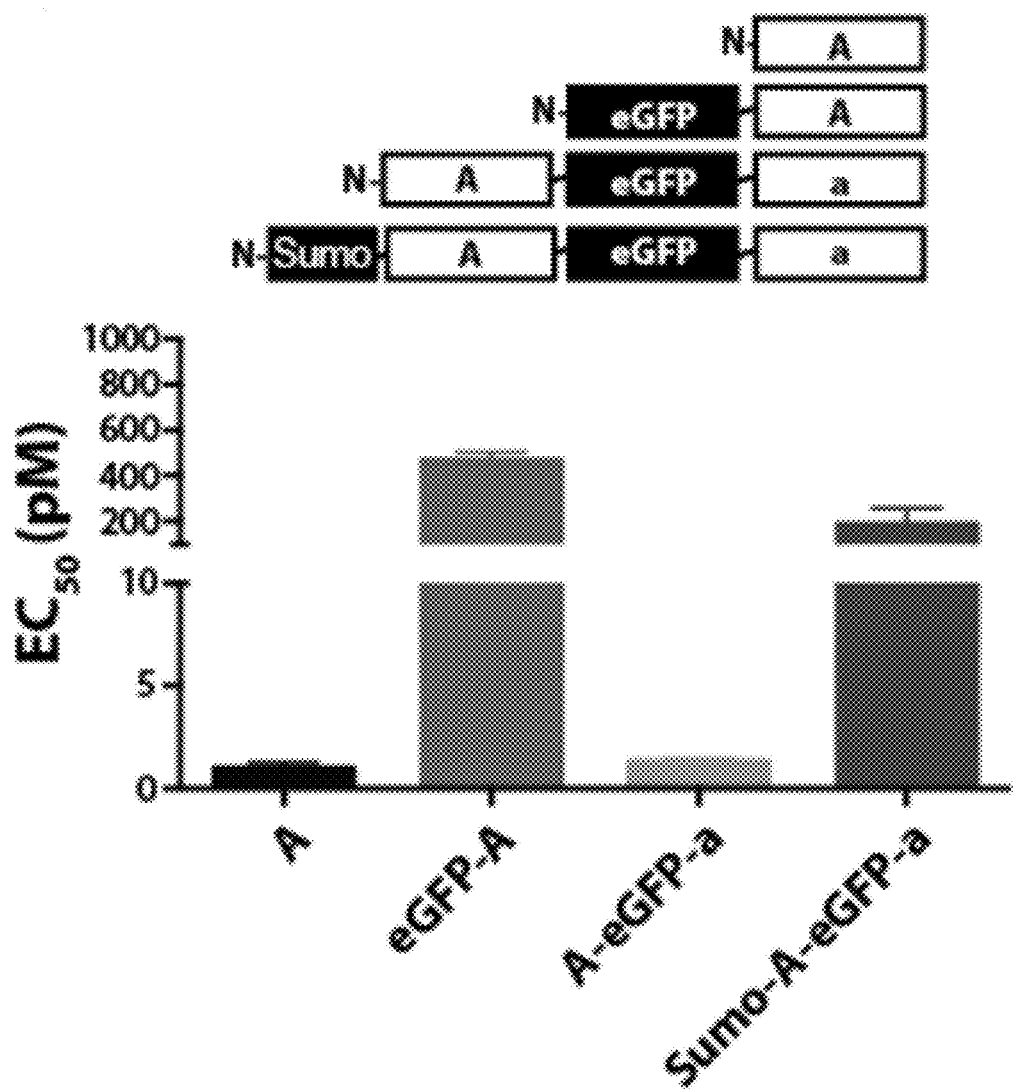
FIG. 5 depicts the results of cell toxicity assays to measure the positional effects of dtA on inhibition of protein synthesis. 'A' (uppercase) indicates a catalytically active diphtheria toxin enzymatic fragment (dtA), while 'a' (lowercase) indicates a catalytically inactive diphtheria toxin enzymatic fragment (dta).

FIG. 5 depicts the construct and shows, remarkably, that A-eGFP-a-B inhibited protein synthesis such that it was indistinguishable from wildtype-like toxin. This shows that the shifts in potency are due to proximity effects on dtA activity. Further, FIG. 5 shows that addition of Sumo onto the amino terminus of this construct shifted the apparent activity back to levels observed with amino-terminal cargo constructs. Bars represent average $EC_{50} \pm SD$ (n=3).

Figure 6:
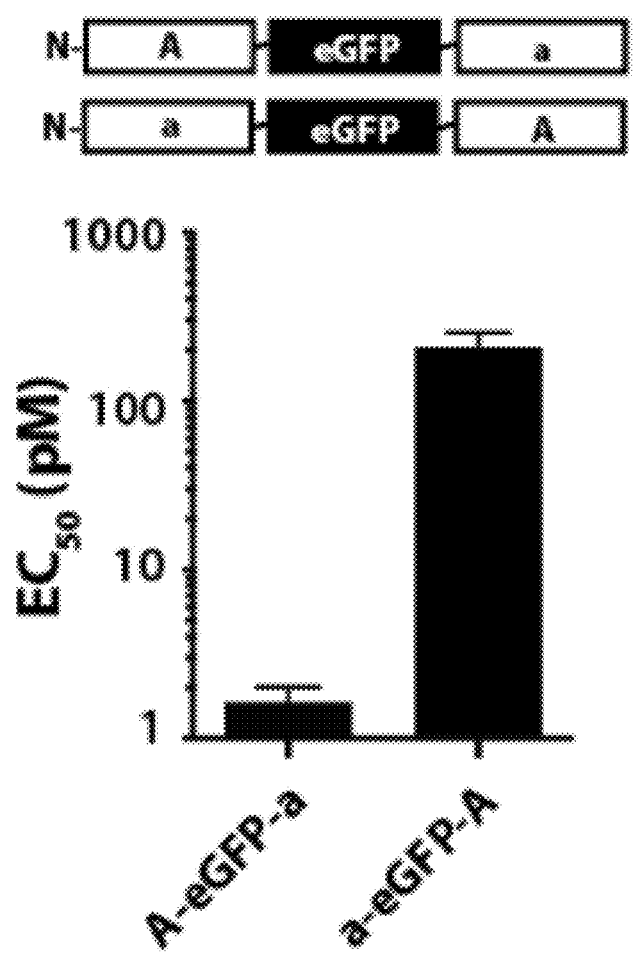
FIG. 6 depicts data in addition to FIG. 5 to rule out the possibility that the amino terminal dtA fragment was affecting translocation. 'A' (uppercase) indicates a catalytically active diphtheria toxin enzymatic fragment (dtA), while 'a' (lowercase) indicates a catalytically inactive diphtheria toxin enzymatic fragment (dta).

FIG. 6 corroborates certain findings depicted in FIG. 5. To rule out the possibility that the amino terminal dtA fragment was affecting translocation, it is shown that a-eGFP-A is shifted similar to eGFP-A. Bars represent average $EC_{50} \pm SD$ (n=3).

To show that this phenomenon was not specific to eGFP, a similar set of constructs were generated, using α-amylase as the passenger domain.

Figure 7:
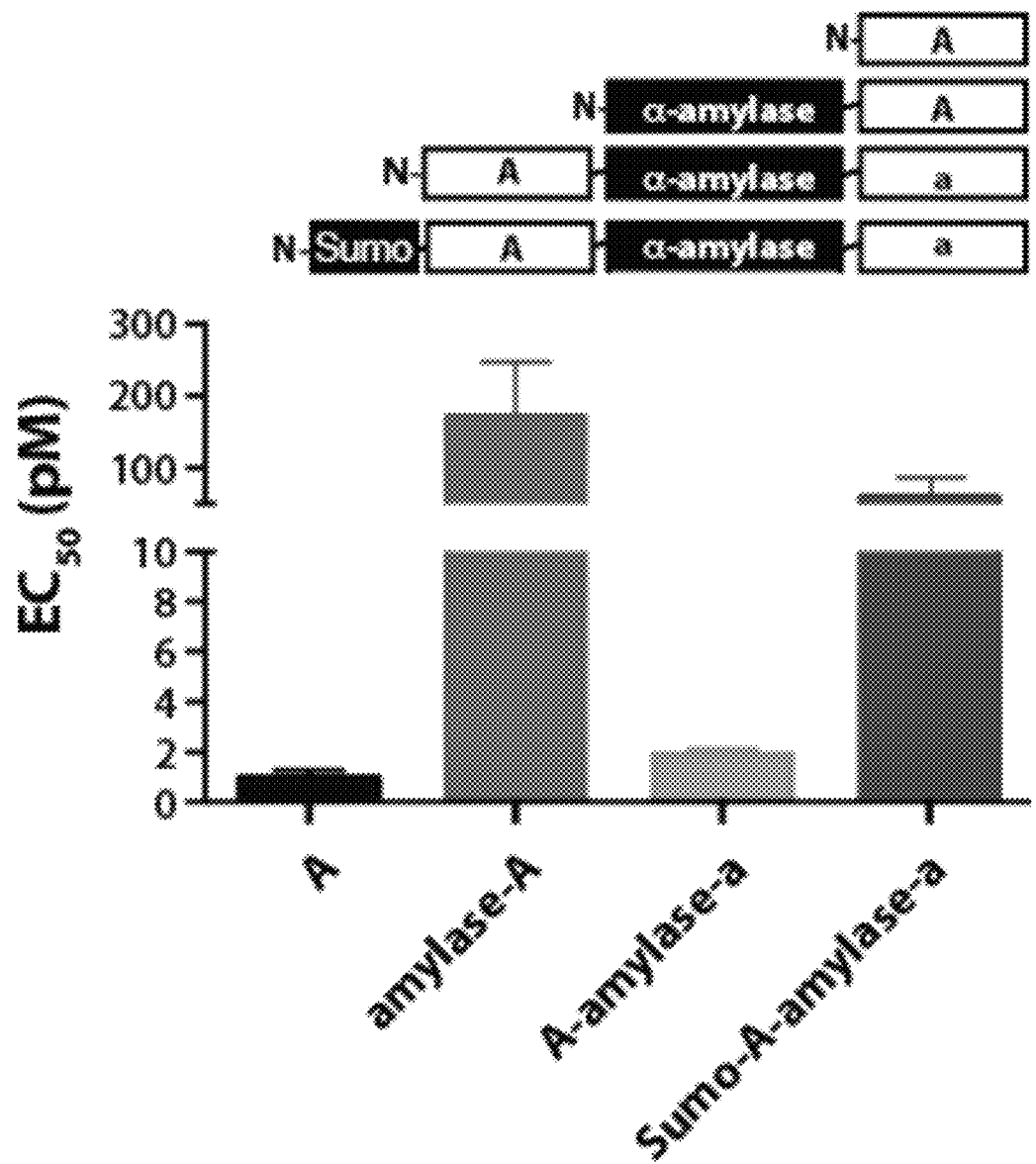
FIG. 7 depicts data in addition to FIG. 5 showing the same positional dependence for dtA when amylase is the passenger protein. 'A' (uppercase) indicates a catalytically active diphtheria toxin enzymatic fragment (dtA), while 'a' (lowercase) indicates a catalytically inactive diphtheria toxin enzymatic fragment (dta).
Figure 8:
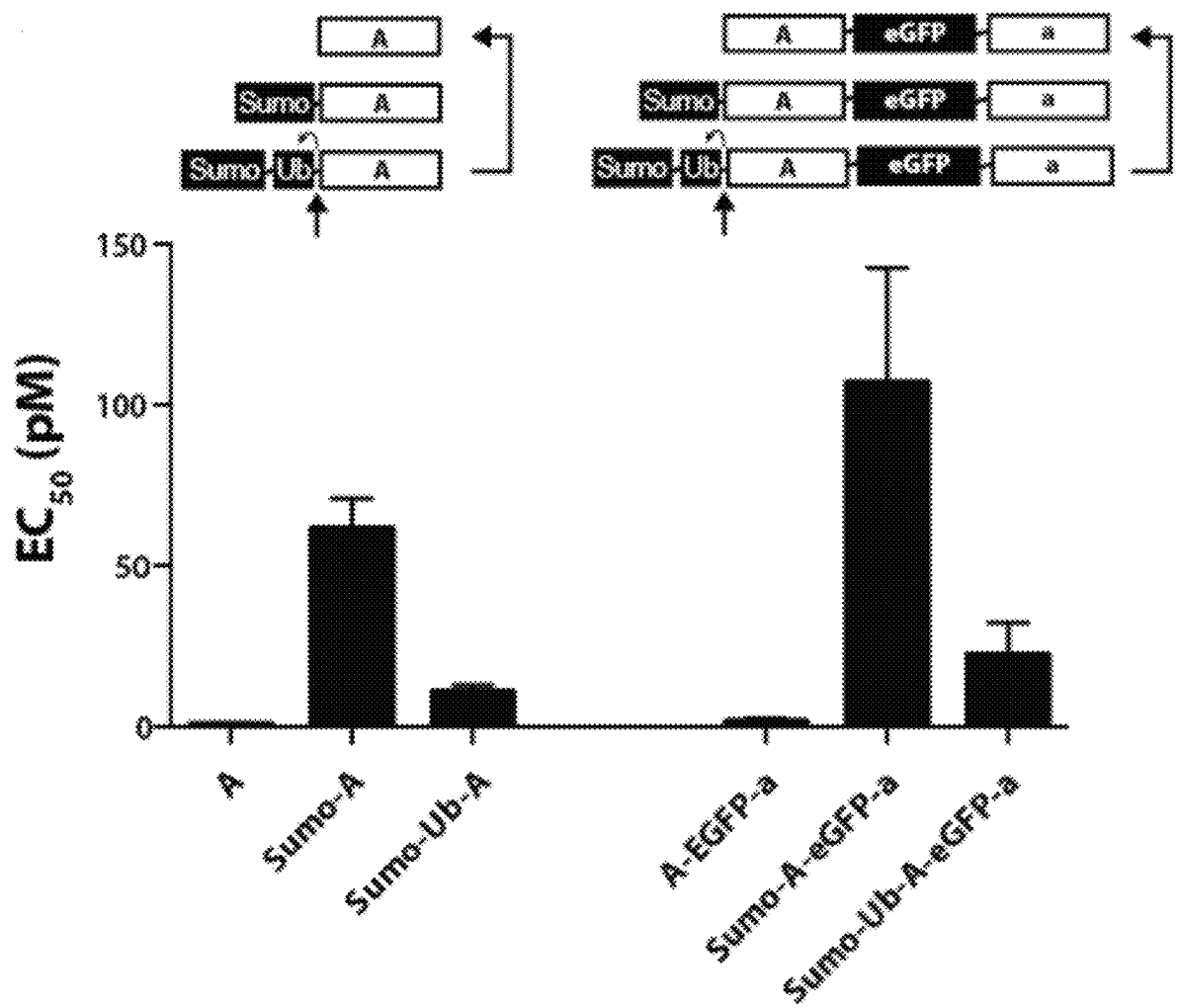
FIG. 8 depicts the results of cell toxicity assays indicating that passenger proteins reach the cytosol. 'A' (uppercase) indicates a catalytically active diphtheria toxin enzymatic fragment (dtA).
Figure 9:
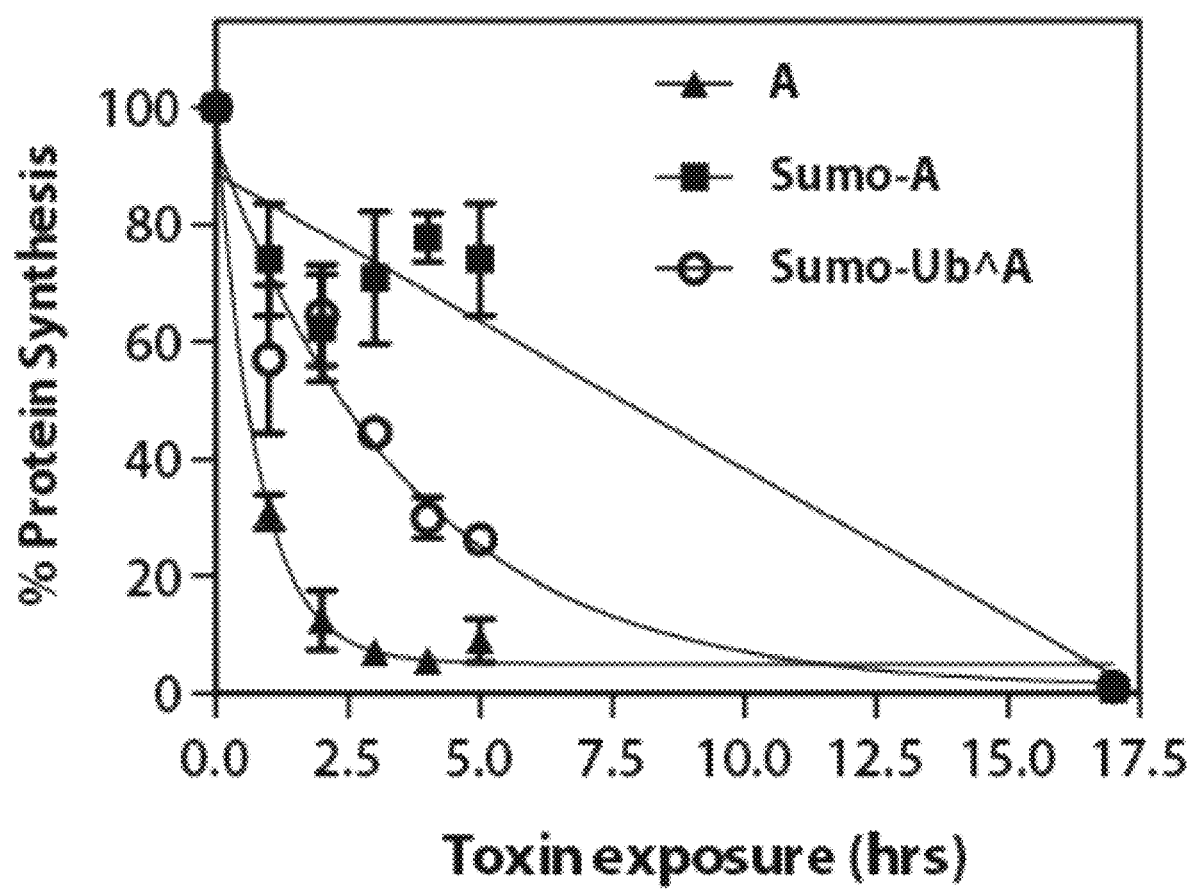
FIG. 9 depicts a time course of inhibition of protein synthesis of three constructs using 1 nM of each toxin. 'A' (uppercase) indicates a catalytically active diphtheria toxin enzymatic fragment (dtA).
Figure 10:
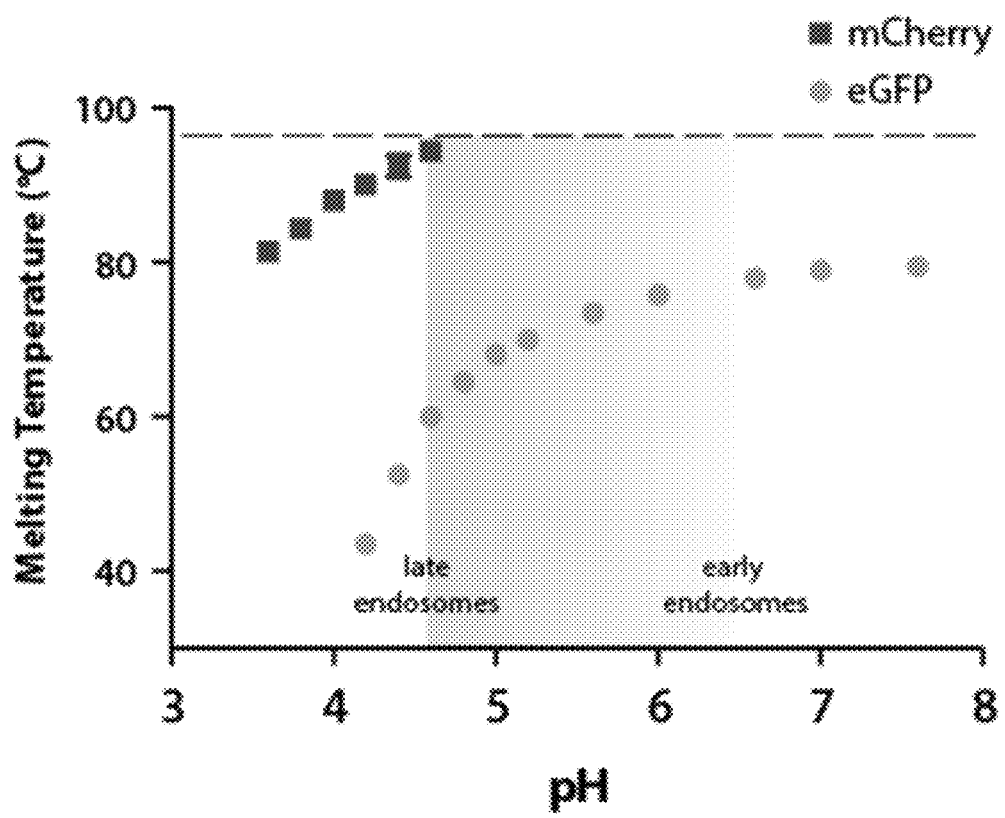
FIG. 10 depicts the results of differential scanning fluorimetry at various pH values for eGFP and mCherry.
Figure 11:
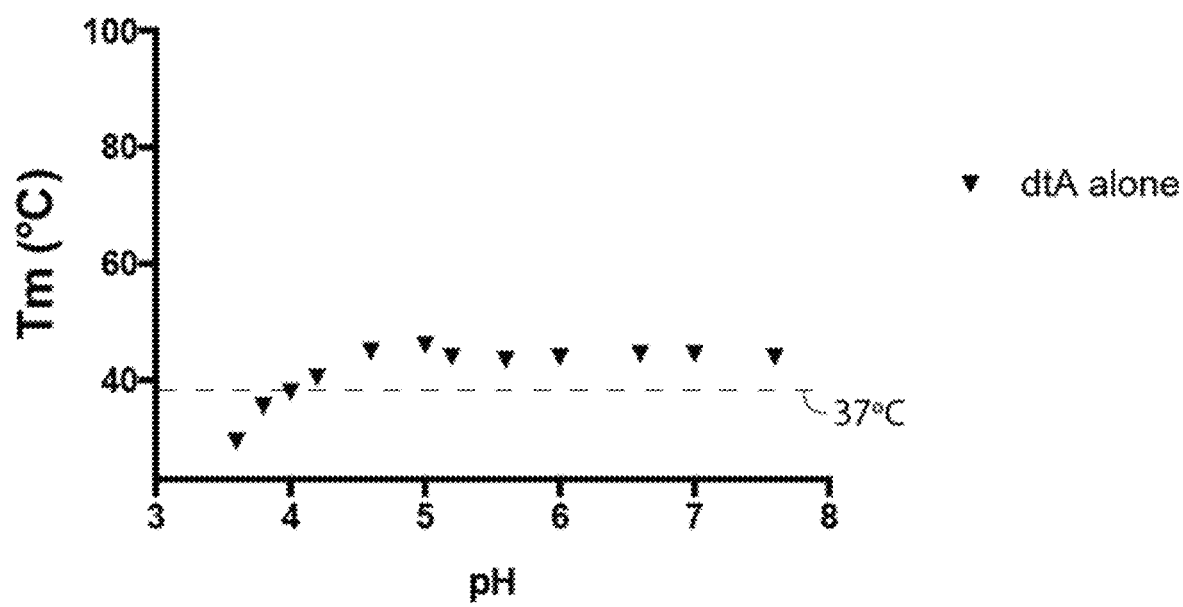
FIG. 11 depicts pH-induced unfolding of dtA alone using differential scanning fluorimetry, with the transition midpoint of unfolding (Tm) shown across several pH values.
Figure 12:
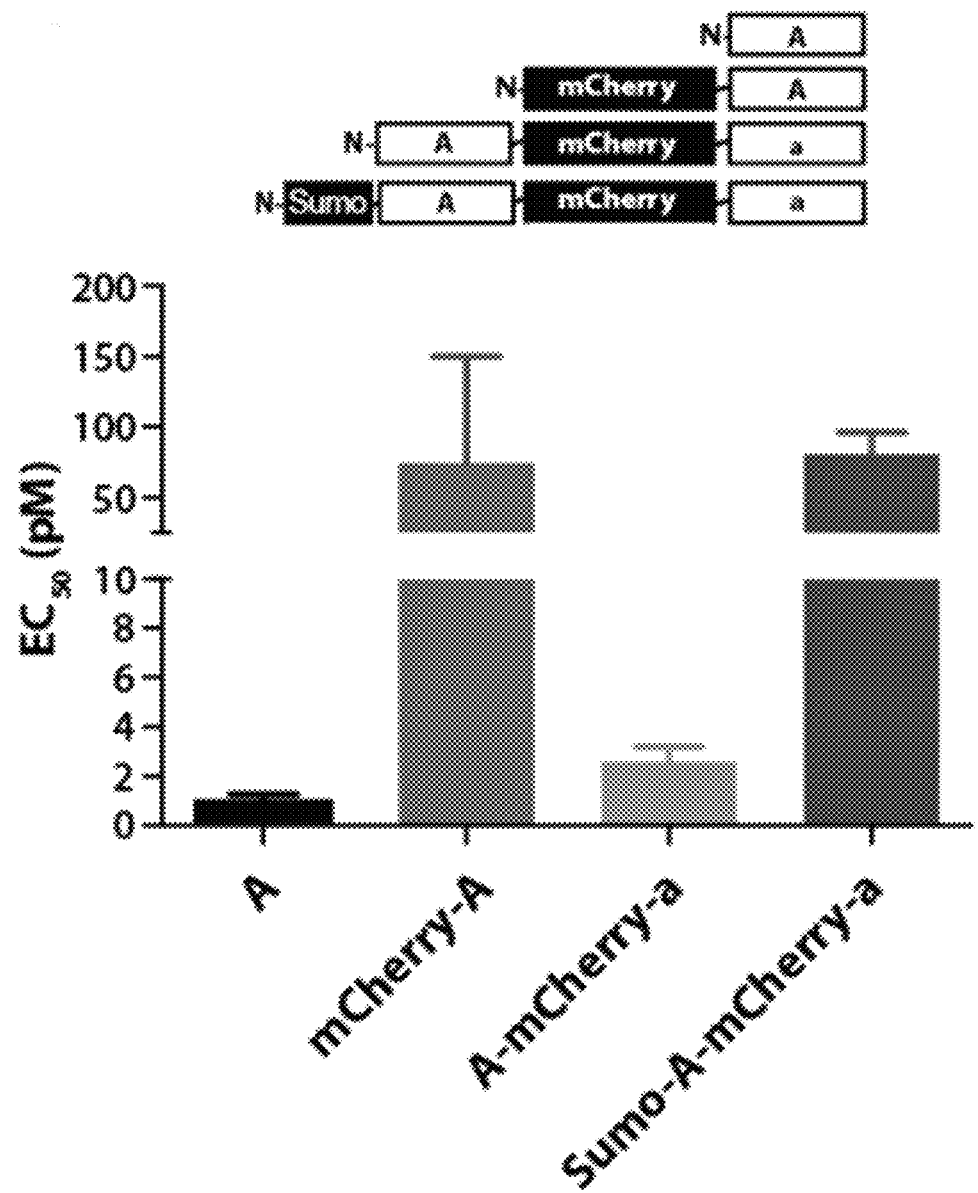
FIG. 12 depicts the results of cell toxicity assays indicating that mCherry is efficiently delivered into cells by DT. 'A' (uppercase) indicates a catalytically active diphtheria toxin enzymatic fragment (dtA), while 'a' (lowercase) indicates a catalytically inactive diphtheria toxin enzymatic fragment (dta).
Figure 13:
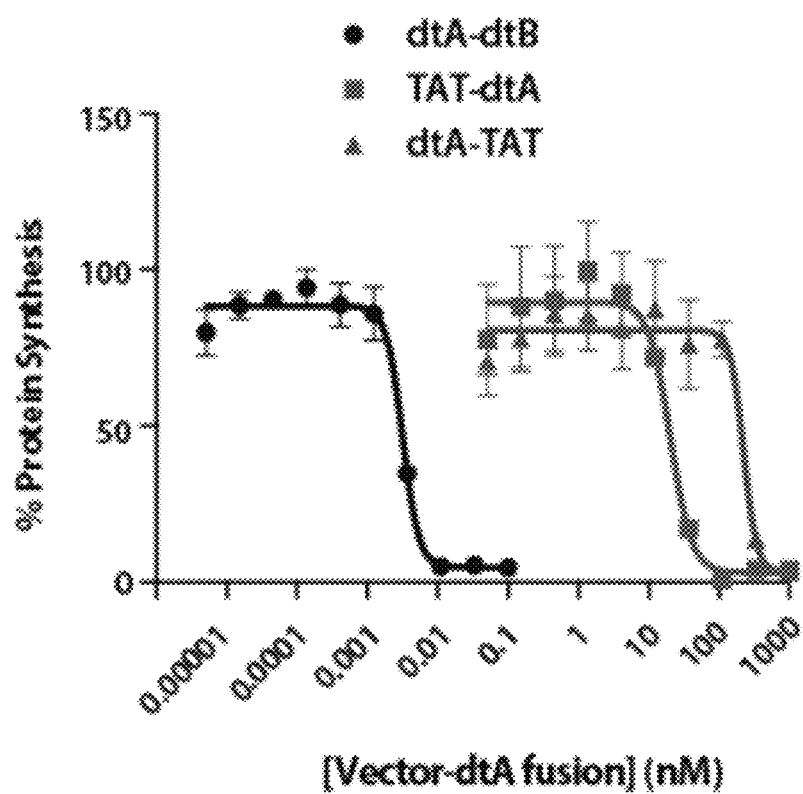
FIG. 13 depicts the results of cell toxicity assays comparing delivery of dtA by dtB and TAT peptides.
Figure 14:
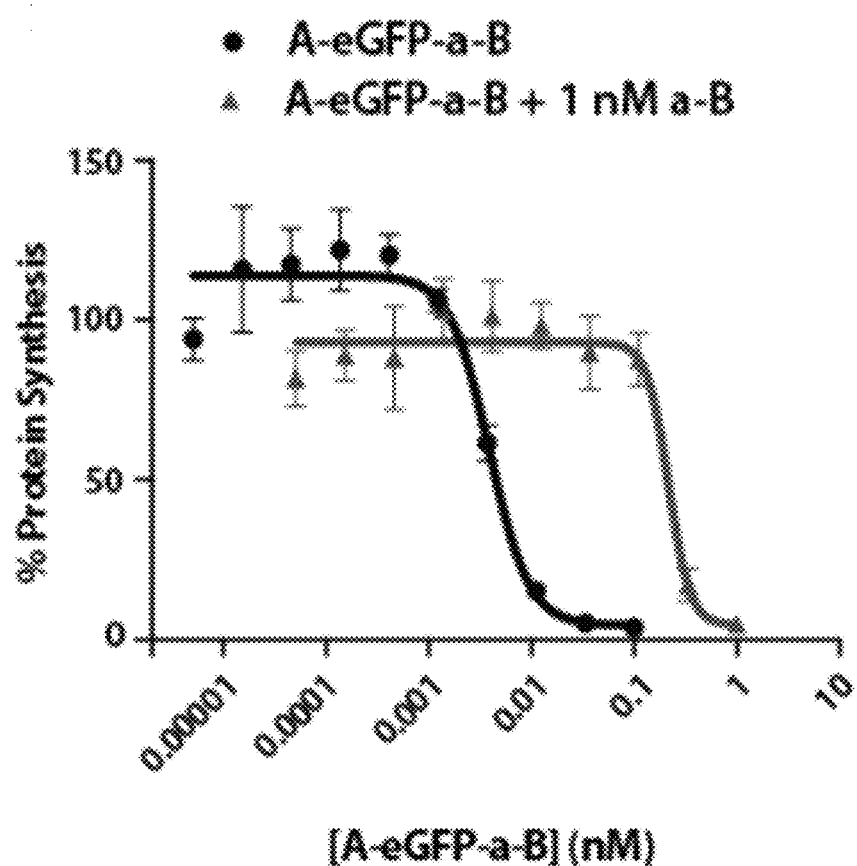
FIG. 14 depicts the results of cell toxicity assays demonstrating that enzymatically inactive DT competes with A-eGFP-a-B, wherein 'A' (uppercase) indicates a catalytically active diphtheria toxin enzymatic fragment (dtA), eGFP indicates enhanced green fluorescent protein, 'a' (lowercase) indicates a catalytically inactive diphtheria toxin enzymatic fragment (dta), and B indicates a functional diphtheria toxin translocation fragment (elsewhere dtB).

FIG. 7 shows that the same positional dependence of dtA on activity was observed when using amylase as the passenger protein. Bars represent average $EC_{50} \pm SD$ (n=3).

The 'wildtype-like' potencies observed for A-cargo-a-B constructs have several important implications for DT delivery. In addition to strongly supporting the hypothesis that amino-terminal passenger proteins affect dtA activity after they reach the cytosol, rather than impeding receptor binding or translocation, these data indicate that passenger proteins are virtually invisible to the translocation machinery of DT. Also, because translocation initiates with the C-terminal end of the A-domain that is adjacent to the B-moiety and proceeds such that the amino terminus is last to enter the cytosol[11], these findings show unequivocally that passenger proteins fully enter the cytosol. Finally, these constructs eliminate any possibility that the inhibition of protein synthesis observed for chimeric toxins is from breakdown products in which cargo was removed prior to or during intoxication, since amino terminal truncations would result in the loss of dtA and would be nontoxic.

Building on these findings, the predictable shifts observed with amino terminal fusions to dtA were exploited, and the unique properties of ubiquitin and deubiquitinating enzymes found only in the cytosol, to demonstrate intracellular delivery through an independent measure. Since cytosolic deubiquitinating enzymes cleave at the C-terminus of ubiquitin (Ub), Ub was inserted between passenger proteins and dtA in two different contexts so that the amino terminus of dtA will be liberated only if the entire payload was translocated into the cytosol.

FIG. 8 depicts these constructions, and shows that both Ub-containing constructs were more potent on cells than their des-Ub counterparts, albeit not back to wildtype levels, which may reflect the kinetics of removal of Ub by deubiquitinating enzymes (DUBs). Ub was placed between Sumo and dtA (left panel of FIG. 8) and was found to be more potent on cells than Sumo-A, consistent with deubiquitinating enzymes removing amino terminal cargo and relieving the proximity effect on dtA activity. Using more extensive cargo, the ubiquitin entry assay confirms that large protein cargo enter the cytosol (right panel of FIG. 8).

FIG. 9 depicts a time course of inhibition of protein synthesis of all three constructs using 1 nM of each toxin. Symbols±SD (n=3) are shown.

In addition to demonstrating that passenger proteins are in the cytosolic compartment, these data show that DT can simultaneously deliver multiple different proteins, akin to beads on a string—that combined, are over 100-kDa in size—into the cytosol en masse.

Example 8

The DT Translocation Machinery can Deliver a Folded Protein into Cells

The unexpected plasticity of the DT translocation machinery observed with large and diverse protein cargo prompted the question of whether DT could transport stably folded proteins into cells. To this end, the fluorescent protein variant derived from *Discosoma* sp. "DsRed" called monomeric Cherry (mCherry) was used. Though similar in size and structure to eGFP, mCherry been shown to possess dramatically increased conformational stability relative to eGFP in vitro and in vivo. Constructs were generated per Example 1.

FIG. 10 shows that, using differential scanning fluorimetry, mCherry was indeed dramatically more stable to thermal- and pH-induced unfolding than eGFP. Shaded region shows pH levels within early to late endosomes where translocation takes place. Above pH 4.6, mCherry does not unfold up to 95° C. Symbols represent average $T_m$±SD (n=3).

FIG. 11 shows that mCherry was also more stable than dtA.

In fact, an unfolding transition for mCherry could only begin to be measured below pH 4.6, strongly suggesting that unfolding of mCherry is not likely to occur within endosomal compartments, where membrane translocation occurs. Zornetta et al.[22] recently investigated anthrax toxin translocation in cells and found that whereas eGFP fusions to lethal factor (LF) were efficiently transported through the narrow and fixed protective antigen (PA) pore, similar fusions with mCherry were unable to translocate into cells, supporting the notion that eGFP, but not mCherry unfolds in early endosomes prior to translocation.

To test whether the DT translocation apparatus could deliver stably folded mCherry into cells, mCherry-DT chimeras were generated using the same platform designs as above, in Example 1.

FIG. 12 depicts the results of cell toxicity assays indicating that mCherry is efficiently delivered into cells by DT. Surprisingly, unlike the anthrax toxin translocation system, diphtheria toxin was able to deliver mCherry into cells with wildtype like efficiency. mCherry, like eGFP and amylase are invisible to the DT translocation machinery. Though the possibility cannot be excluded that mCherry is somehow mechanically unfolded immediately prior to, or during translocation, these data indicate, at the very least that DT can accommodate and transport hyper-stable proteins. Furthermore these findings show that DT is distinct from and has a broader substrate profile than the anthrax toxin pore suggesting that not all toxin translocation systems are alike.

Example 9

Comparison and Characterization of the DT Delivery Platform

With the observed differentiation from anthrax toxin, further benchmarking of DT against a non-toxin derived protein delivery platform was sought. To this end, the ability of the cell-penetrating TAT peptide from HIV-1[1] to deliver dtA into the cytosol was evaluated. Given the effects observed here on dtA activity in the presence of amino-terminal extensions, both TAT-dtA and dtA-TAT were generated and compared their ability to inhibit protein synthesis with the translocation machinery of DT (i.e., dtB).

FIG. 13 shows results comparing the delivery of dtA by dtB and TAT peptides, and shows that both Tat-dtA and dtA-Tat were able to penetrate cells and inhibit protein synthesis. Symbols±SD (n=3) are shown. However, as reported previously for TAT-dtA, the concentrations required for both TAT constructs were at least four orders-of-magnitude higher than those required for DT. Beyond this clear efficiency advantage for DT, an important conceptual advantage of the DT system over existing protein delivery platforms such as TAT, is the target-cell specificity conferred by a receptor-binding domain.

To confirm that cargo translocation by DT was receptor-dependent, a competition experiment between A-eGFP-a-B and catalytically inactive DT was performed.

FIG. 14 shows that, in the presence of 1 nM nontoxic DT, the potency of A-eGFP-a-B was shifted from 3.8 pM to 215 pM, confirming that cargo delivery was receptor-dependent, and that the cargo itself did not mediate its own uptake. Symbols±SD (n=3) are shown.

Figure 15:
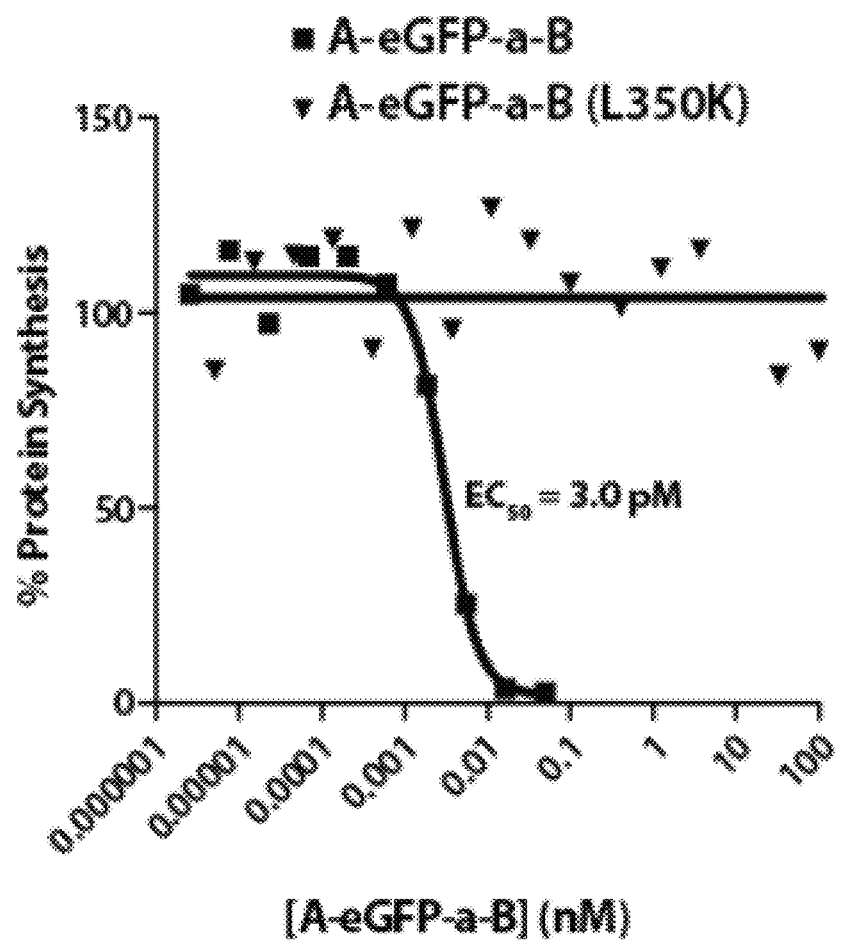
FIG. 15 depicts the results of cell toxicity assays examining the effect of a pore-formation formation/translocation-defective mutation (L350K).
Figure 16:
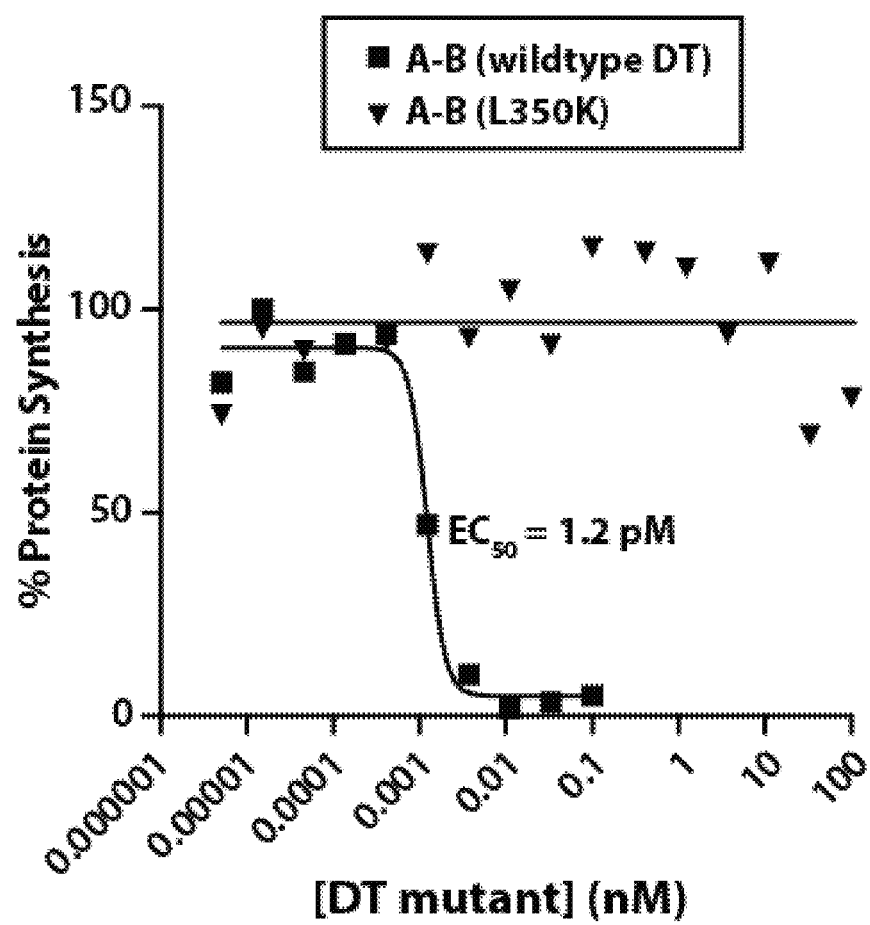
FIG. 16 depicts further data indicating that the pore-formation/translocation mutant L350K is unable to enter cells and inhibit protein synthesis.
Figure 17:
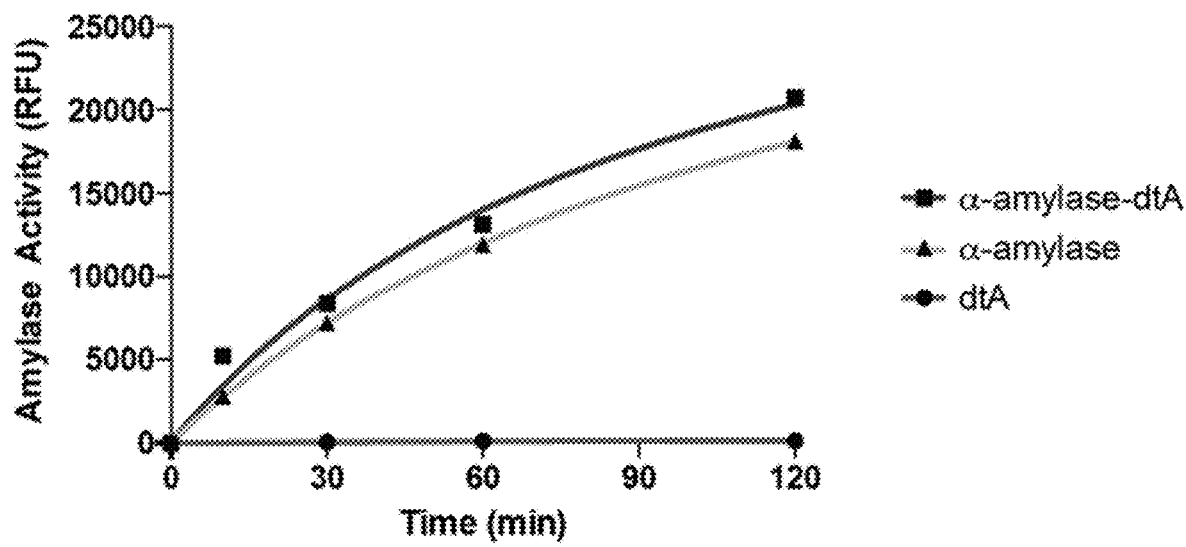
FIG. 17 depicts data obtained with the EnzChek™ Ultra Amylase Assay indicating that amylase fused to DT is folded and functional.
Figure 18:
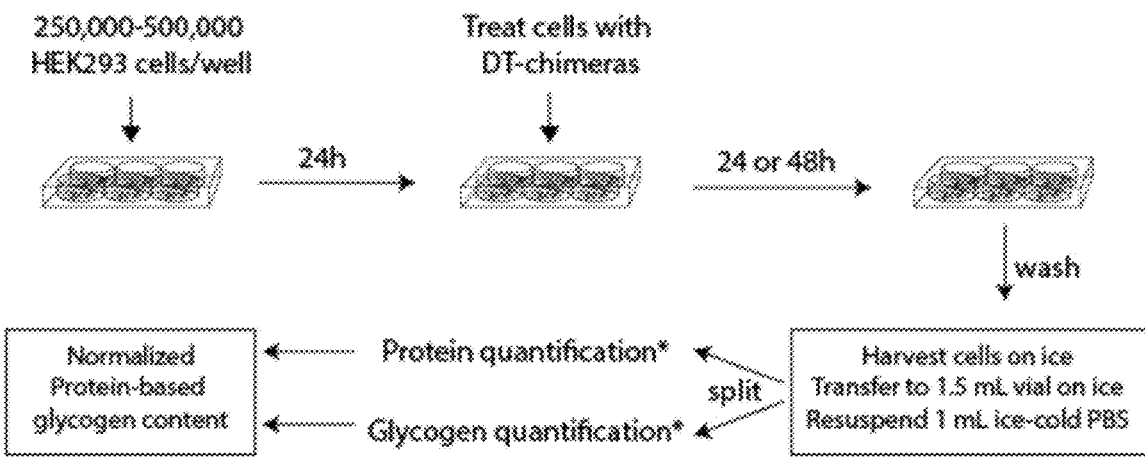
FIG. 18 depicts the experimental design for α-amylase-DT treatment of HEK 293 cells.
Figure 19:
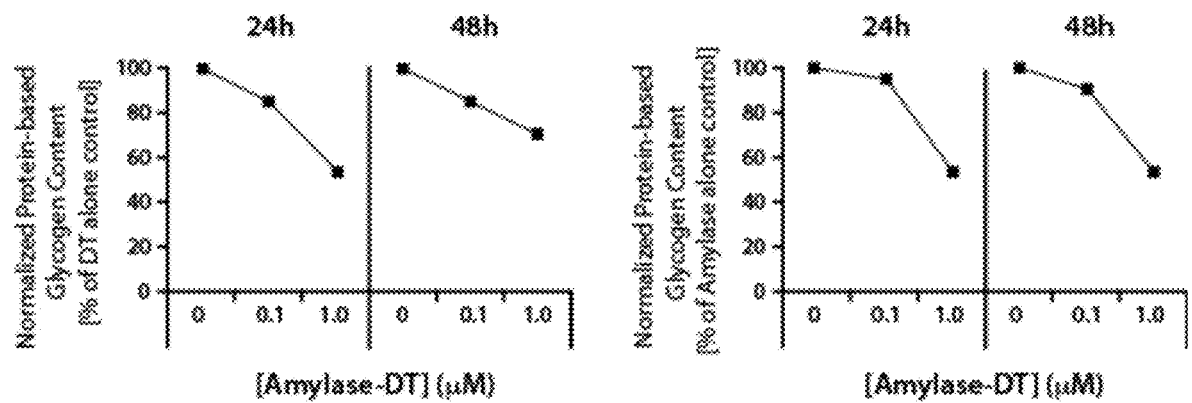
FIG. 19 depicts measurements of protein-based glycogen content in HEK cells after 24 h or 48 h treatment normalized on content in cells treated with either DT alone or amylase alone, respectively (n=1).
Figure 20:
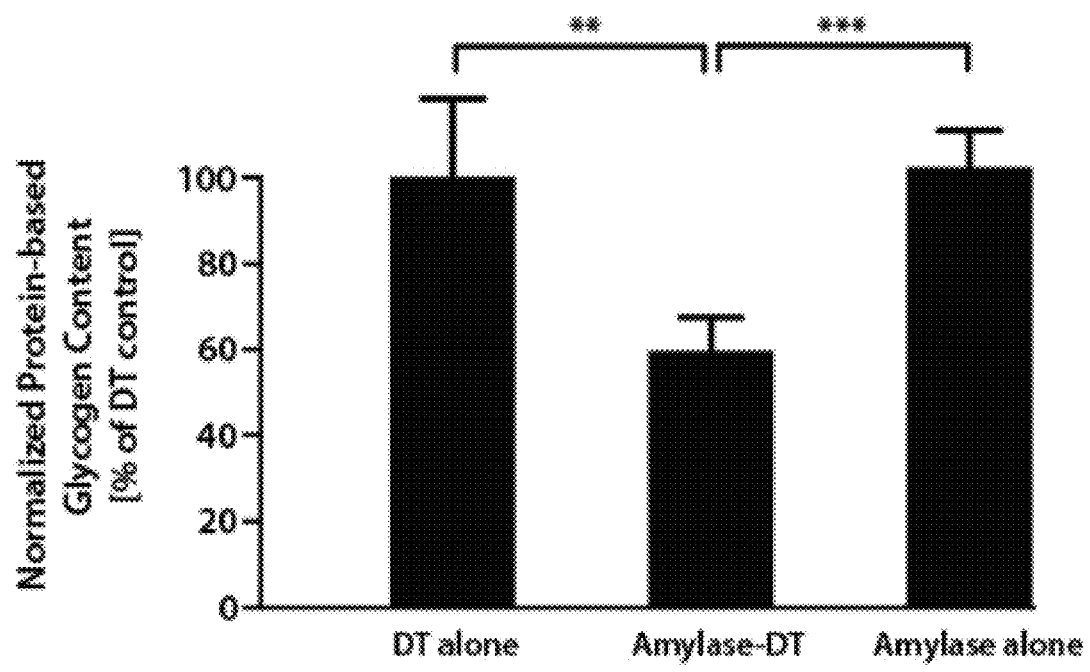
FIG. 20 depicts protein-based glycogen content in HEK cells after 24 h treatment with 1.0 uM DT, amylase-DT, or amylase alone.
Figure 21:
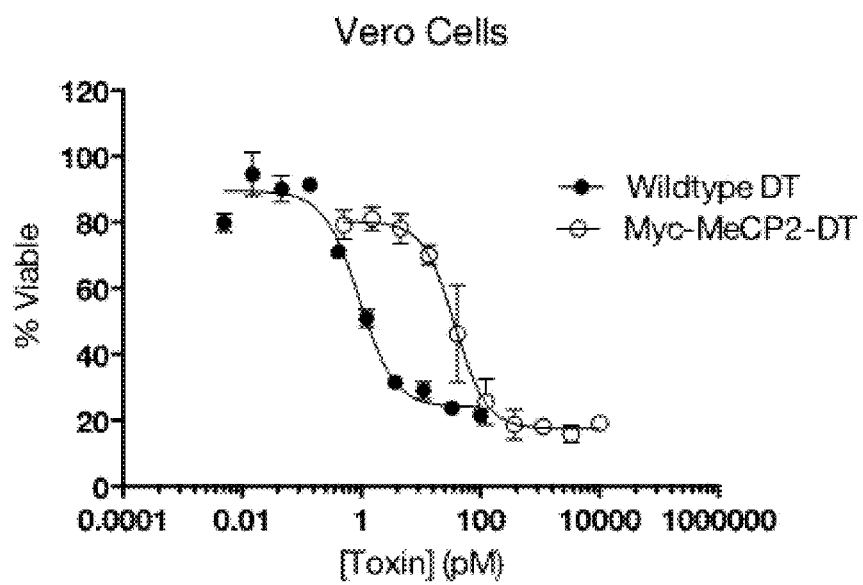
FIG. 21 depicts results of protein toxicity studies cells indicating proof of delivery of MeCP2e1 into the cytosol of Vero cells.
Figure 22:
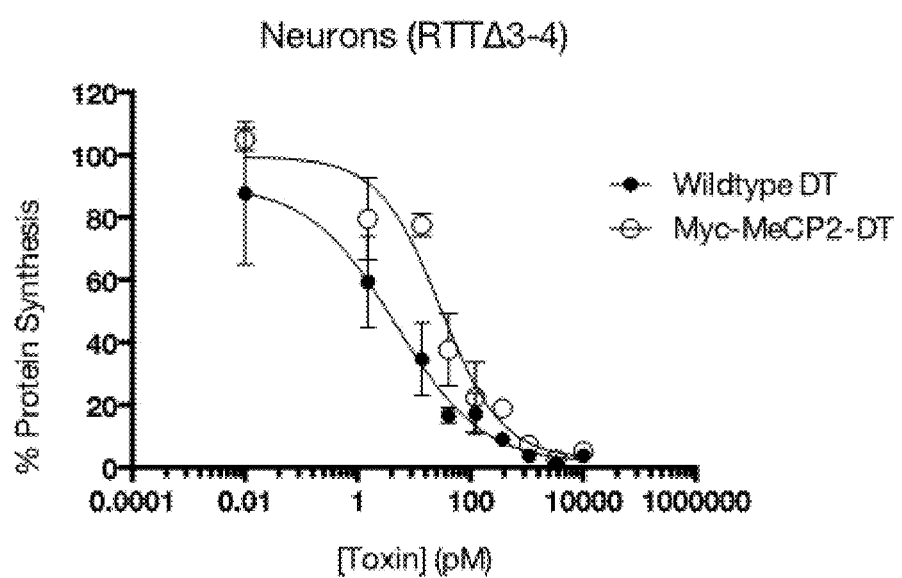
FIG. 22 depicts results of cell toxicity assays indicating proof of delivery of MeCP2e1 into the cytosol of iPSC-derived neurons from Rett Syndrome patient fibroblasts.
Figure 23:
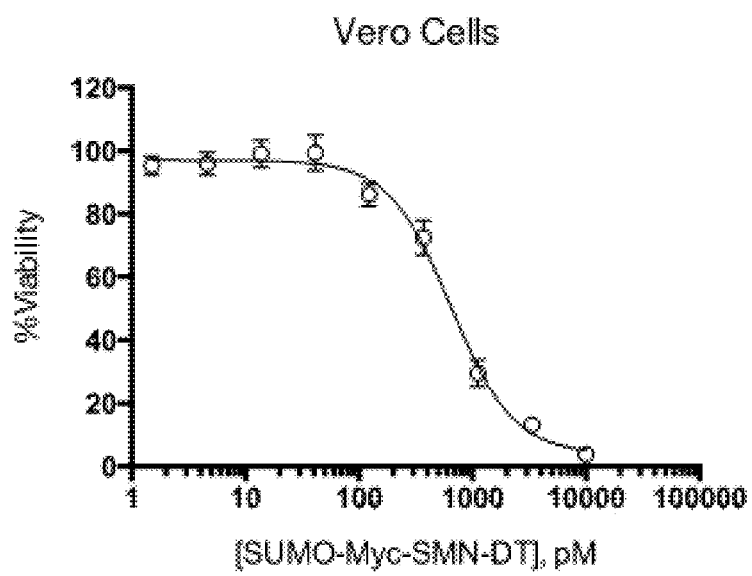
FIG. 23 depicts results of cell toxicity assays indicating proof of delivery of SMN into the cytosol of Vero cells.
Figure 24:
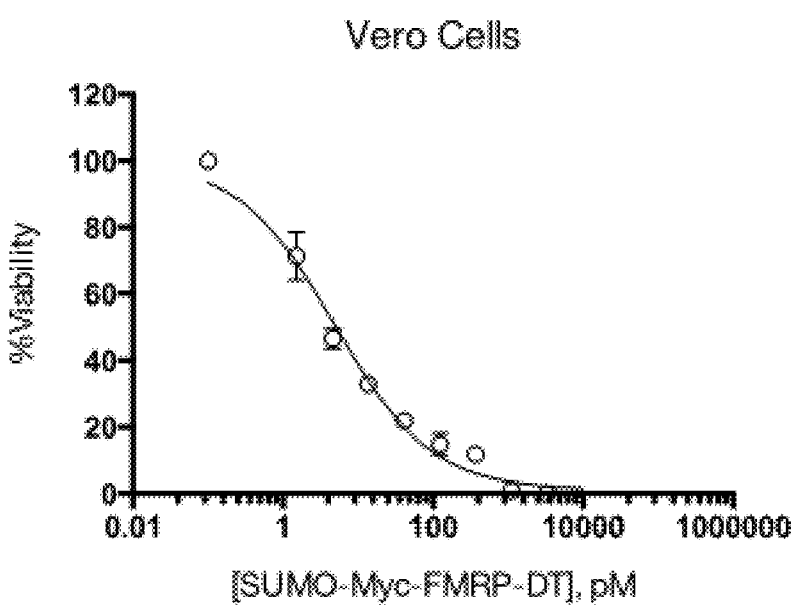
FIG. 24 depicts results of cell toxicity assays indicating proof of delivery of FMRP into the cytosol of Vero cells.
Figure 25:
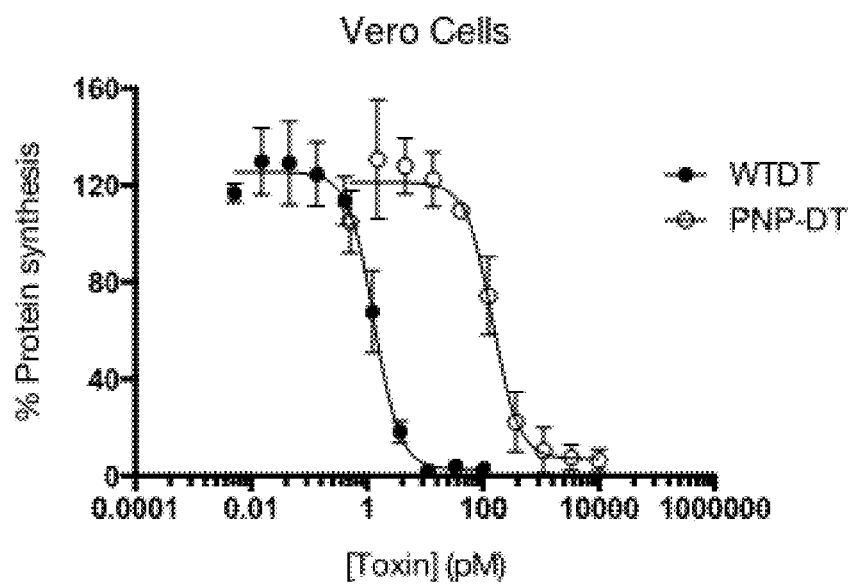
FIG. 25 depicts results of $^3$H-leucine incorporation toxicity assays demonstrating delivery of PNP into the cytosol of Very cells.
Figure 26:
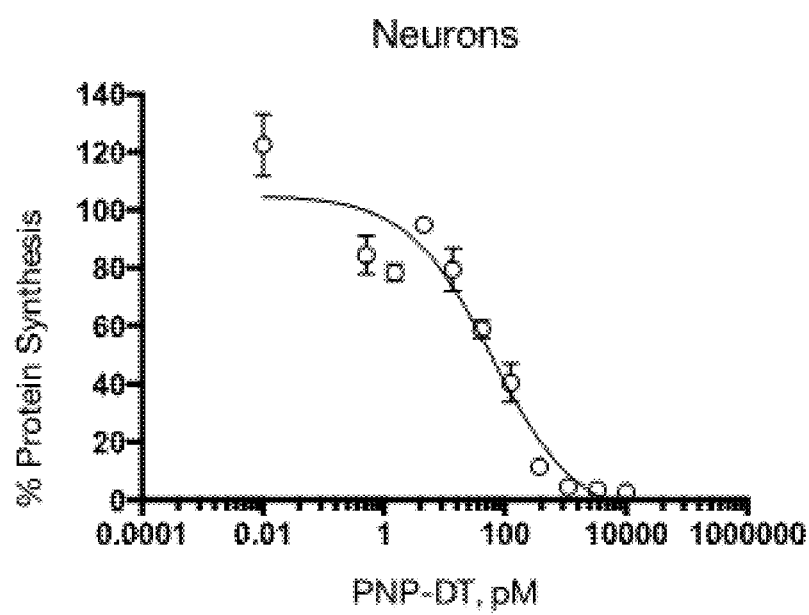
FIG. 26 depicts results of $^3$H-leucine incorporation toxicity assays demonstrating delivery of PNP into the cytosol of two-week old wild type (WT) neurons cells.
Figure 27:
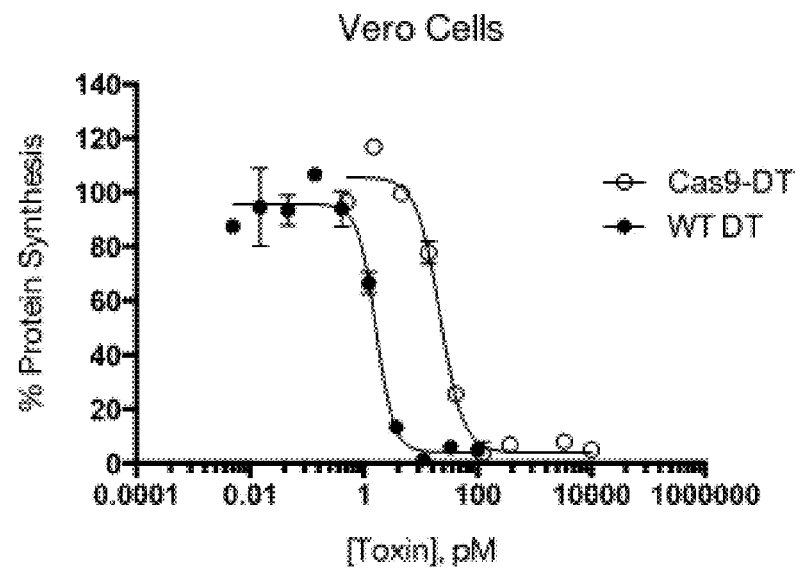
FIG. 27 depicts results of $^3$H-leucine incorporation toxicity assays demonstrating delivery of Cas9 into the cytosol of Vero cells.
Figure 28:
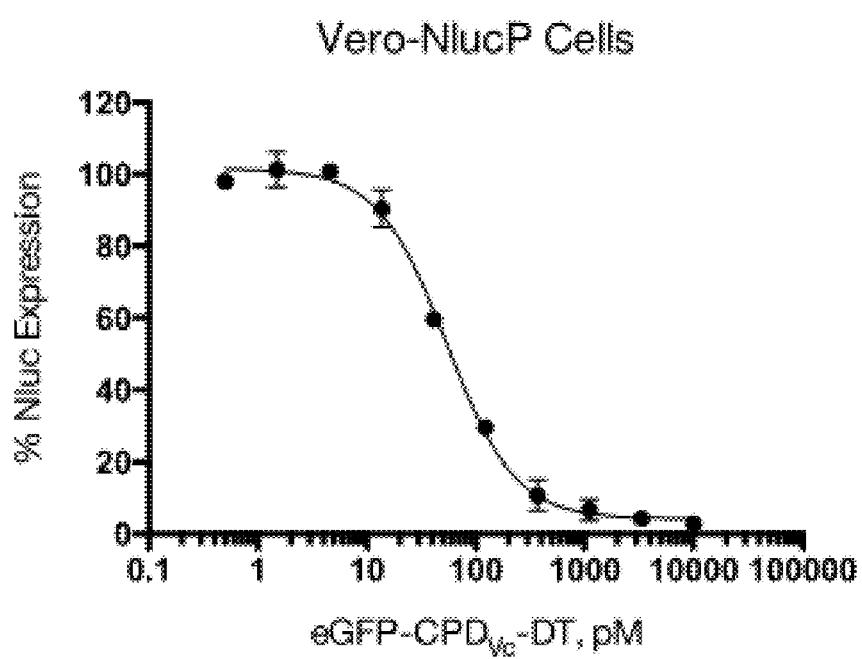
FIG. 28 depicts the results of NanoGlo assays demonstrating delivery of eGFP-CPD$_{Vc}$-DT into the cytosol of Vero-NlucP cells by fusion protein toxicity, wherein eGFP represents enhanced green fluorescent protein, CPD$_{Vc}$ represents a cysteine protease domain from *Vibrio cholera*, and DT represents, and DT represents diphtheria toxin.

FIG. 15 and FIG. 16 show that, using a pore-formation mutant in the translocation domain of DT, which prevents translocation, it is shown that cargo delivery into cells requires a functional translocation domain, and that cargo did not mediate its own entry. Symbols±SD (n=3) are shown.

Example 10

Direct Evidence of Functional Entry of α-Amylase by DT

Having demonstrated that passenger proteins are delivered into cells by DT in a receptor- and translocation-dependent manner with high efficiency, it was next desirable to test whether the delivered cargo was folded and functional within the cytosol. Rather than use the more qualitative measurements of intracellular fluorescence using eGFP or mCherry as cargo, it was desirable to measure the ability of delivered α-amylase to enzymatically digest cytosolic glycogen. An amino-terminal extension of nontoxic DT (i.e., α-amylase-dta-dtB) was prepared in general accordance with Example 1.

FIG. 17 confirms that the specific activity of α-amylase was equivalent to α-amylase alone using a quenched fluorescence substrate-based assay. The EnzChek™ Ultra Amylase Assay was used to measure the activity of α-amylase-dtA (curve marked with square data points), α-amylase (curve marked with triangular data points), and dtA alone (curve marked with circular data points) over 2 hours.

FIG. 18 depicts the experimental design for α-amylase-DT treatment of HEK 293 cells. HEK293 cells were treated for 24 or 48 h with α-amylase-dta-dtB at two different concentrations to establish conditions where decreases in protein-based glycogen could be detected.

FIG. 19 shows protein-based glycogen content in HEK cells after 24 h or 48 h treatment normalized on content in cells treated with either DT alone or amylase alone, respectively (n=1). Using DT alone or α-amylase as controls, dose-dependent decreases in protein-based glycogen content in cells were observed at both time points, with a slightly more pronounced effect apparent at 24 h.

FIG. 20 shows protein-based glycogen content in HEK cells after 24 h treatment with 1.0 uM DT, amylase-DT, or amylase alone. Error bars, SD (n=4; Significance as determined with STUDENT t-test ($p<0.01$, ; $p<0.001$, *). A highly significant decrease in glycogen observed was using 1 μM α-amylase-dta-dtB, which demonstrates that the translocated α-amylase-dta is folded and active in the cytosol, and shows that the amounts delivered are sufficient not only to degrade existing glycogen, but also to compete with on-going cellular glycogen synthesis. The measured breakdown of glycogen is thus likely an underestimation of the intracellular activity. Moreover, because maltose or any longer glucose oligomer—though also products of the amylase-mediated glycogen degradation—would still be determined as 'glycogen' in our biochemical glycogen quantification method, the possibility also exists that even greater amounts of glycogen were degraded by the delivered α-amylase. Nevertheless, these results provide an important proof-of-delivery of a large and functionally active protein into cells by the diphtheria toxin platform.

Example 11

Discussion

In its 'protective' role, the plasma membrane that encases all human cells unwittingly excludes proteins from entering that might otherwise be effective therapeutics. Though several vectors for intracellular protein delivery into cells have been described, few if any combine the attributes of efficiency, target-cell specificity and low toxicity into a single platform. In this study, a protein-delivery vector is described, which based on the versatile diphtheria toxin that is capable of translocating proteins of varying structural motifs, stabilities and sizes including those that are over 100-kDa in size, with high efficiency into specific receptor-bearing cells (see Table 2, above, for a list of chimeric constructs with molecular weights). Engineering protein toxins to create 'designer chimeras' is not a new concept, however, efforts thus far have largely focused on delivering the toxic A-fragment enzymes into specific target cells through modifications to the receptor-binding domain of toxins. Denileukin difitox (Ontak®), an FDA-approved anti-neoplastic agent created through the fusion of human Interleukin-2 (IL2) to a truncated form of DT (viz. dtA-dt$B_{389}$-IL2), binds the IL2 receptor that is overexpressed in various malignancies and translocates dtA into the cytosol to ultimately specifically ablate cancerous cells[12,13]. Recent breakthroughs that serve to improve the safety profile and specificity of immunotoxins have intensified interest in these therapeutics with several now in clinical development, largely for cancer-related indications[13-15].

This study investigated creating a different type of toxin-based 'designer chimera', taking advantage of the cell-penetrating properties of DT, rather than its cytotoxic features. Previous studies investigating passenger protein delivery with toxins have had mixed success. Using anthrax toxin, there have been a number of reports of successful delivery of peptide and protein cargo into cells[16-19]. A limitation of anthrax toxin as a delivery system—aside from it being composed of two separate proteins that must find each other on the cell surface to become delivery competent—is the rigid β-barrel translocation pore[20,21] of the B-fragment of anthrax toxin[22] that necessitates complete unfolding of passenger proteins. It has been shown here that DT, on the other hand, can deliver large and structurally diverse proteins into cells with relative ease. Previous studies investigating the utility of DT as a protein delivery vector were inconclusive, in large part because the addition of cargo to the amino terminus decreased the apparent efficiency of intracellular delivery as determined using the 'gold-standard' measure of protein synthesis inhibition. An important discovery here is that the translocation step itself was not impeded for all passenger proteins tested, but rather the activity of dtA was diminished by the juxtaposition of amino terminal proteins. Of equal importance is the finding that DT was able to transport hyper stable, potentially folded, proteins into cells.

An important consideration for future development of DT- and other toxin-based protein delivery vectors is the extent to which immunogenicity can be addressed for in vivo applications. Recent breakthroughs in identifying and eliminating both B-cell[23] and T-cell[15,24] epitopes on toxin-based proteins suggest that there are manageable strategies to redesign the surfaces of toxins without disrupting their cell-penetrating properties. With the growing library of chimeric toxins targeting different cell types, next generation toxin designs incorporating different features that target particular proteins to specific cells/tissues will serve to further expand the potential of DT-based systems as intracellular protein delivery platforms, ultimately for therapeutic delivery of proteins into cells in vivo.

Example 12

Delivery of Additional Cargo

Additional constructs were made to test the ability of the DT platform to delivery other proteins, including cargo of therapeutic significance (e.g. MecP2, SMN, FMRP, FMRP), cargo for genome editing applications (e.g. Cas9), and an auto-processing release domain (e.g. CPD).

Materials and Methods

Cell Lines

Vero cells are grown in DMEM with 10% fetal bovine serum and 1% penicillin/streptomycin. Vero-NlucP cells are Vero cells stably expressing a Nanoluciferase-PEST fusion protein (NlucP; Promega) delivered via lentiviral vector and subsequent puromycin selection and clonal selection. Both WT and RTTΔ3-4 were derived from fibroblasts of a single Rett Syndrome patient (Cheung et al 2011). RTTΔ3-4 neurons lack exons 3 and 4 of the MeCP2 gene, resulting in a MeCP2-null cell line. WT neurons are isogenic controls. Neurons were kindly provided by Dr. James Ellis.

Expression and Purification of Fusion Proteins

Recombinant DT fusion proteins were expressed as N-terminal His-tagged proteins using the Champion pET-SUMO expression system (Invitrogen), except Myc-MeCP2-DT, which does not have either an N-terminal His or SUMO tag. Fusion proteins were expressed in $E.\ coli$ BL21(DE3) cells. Cells were transformed with the individual plasmids and grown to an OD of ~0.6. Myc-MeCP2-DT was induced with 0.5 mM IPTG and expressed at 28° C. for 6 hours. Myc-SMN-DT and Myc-FMRP-DT were induced with 1 mM IPTG and expressed at 16° C. for 18 hours. PNP-DT was expressed with 1 mM IPTG and expressed for 4 hours at 21° C. Cas9-DT was induced with 0.2 mM IPTG and expressed at 18° C. for 18 hours. eGFP-CPD$_{VC}$-DT was induced with 1 mM IPTG and expressed at 21° C. for 5 hours. All lysates were purified on HisTrap FF Crude (GE Healthcare) chromatography columns. Cas9-DT was further purified on a GE Heparin FF column, while eGFP-CPD$_{VC}$-DT was further purified on a GE Superdex pg75 gel filtration column. All SUMO-tagged proteins were treated with 1 U of SUMO protease (Life Sensor) per 90 µg of purified protein in 20 mM Tris-HCl pH 8 containing 150 mM NaCl and 2 mM DTT. The cleavage reaction was incubated at 30° C. for 1 hour followed by purification with His-Pure Ni-NTA resin (Thermo Scientific) to remove the His-SUMO tag and SUMO protease from the purified fusion proteins.

DT Toxicity Assays

Cell Viability Assay

Vero cells were plated at 4000 cells/well in a 96-well cell culture plate and allowed to attach overnight at 37° C. and 5% C0$_2$. The next day, fusion toxins were added at various concentrations in DMEM (10% FBS, 1% penicillin/streptomycin). After 48 hours, 100 µl of Presto-Blue (Life Technologies) cell viability dye was added to all wells and incubated at 37° C. for 2 hours. Fluoresence was measured in a SpectraMax M5e microplate reader (Molecular Devices) (Ex/Em 555/585 nm). Results were quantified and fit to a sigmoidal function in GraphPad Prism.

$^3$H-Leucine Incorporation Assay

Vero cells or neurons were plated as above (neurons were used after 2 weeks at 30,000 cells/well). Cells were treated with various concentrations of fusion toxins in either DMEM (10% FBS, 1% penicillin/streptomycin [cDMEM]) (Vero cells) or neurobasal media supplemented with cAMP (1 µM), BDNF (10 ng/ml) GDNF (10 ng/ml) and ascorbic acid (200 ng/ml) (neurons). After 15 hours, cells were washed with 200 µl leucine-free cDMEM then incubated in 50 µl leucine-free cDMEM supplemented with 5 µCi/ml of tritiated leucine for 2 hours at 37° C. Cells were washed with 200 µl of ice-cold PBS, and cellular protein was precipitated with 100 µl ice-cold 10% TCA for 10 minutes at room temperature. Cells were then washed with 100 µl of ice-cold 5% TCA and dissolved in 0.1N NaOH before being transferred into a 96-well polystyrene plate and mixed with 200 µl of scintillation fluid. Total incorporated $^3$H-leucine was measured by scintillation counting using a TopCount NXT.

NanoGlo Assay

Vero cells were transduced with a lentivirus containing the Nanoluc luciferase gene (Promega) fused to a C-terminal PEST degradation domain. Positive clones were selected by puromycin selection followed by clonal selection to make Vero-NlucP cells. These cells were treated with various concentrations of fusion toxins as above for 15 hours. NanoGlo assay (Promega) was carried out per the manufacturer's instructions. Luminescence was read on a SpectraMax M5e microplate reader and data was fit to a sigmoidal function (GraphPad Prism).

Results and Discussion

Cargo of Therapeutic Significance

A primary theme of the development of diphtheria toxin (DT) as a protein delivery platform is the delivery of proteins implicated in recessive monogenic disorders, especially those with a neurological component, as a form of enzyme replacement therapy (ERT). Typically, ERT regimens rely on proteins that are active in the extracellular environment or in the endosomal/lysosomal pathway due to their inability to penetrate the cellular plasma membrane. Others rely on cell-penetrating peptides (CPP) such as the HIV-derived TAT peptide, but these suffer from a lack of specificity, and typically do not cross the blood-brain-barrier (BBB).

The fundamental platform on which all fusion proteins are built is the dtA-dtB, wildtype diphtheria toxin. The dtB domain is composed of the translocation (dtT) domain, and the receptor-binding (dtR) domain. Two inactivating mutations in dtA (K51E and E148K) render the toxin completely non-toxic (referred to as dta herein). All DT fusion proteins were also created with these inactivating mutations as non-toxic versions. A further mutation in the dtT domain (L350K) abrogates toxicity by preventing pore-formation and translocation. All fusion proteins are expressed with an N-terminal polyhistidine tag and a SUMO tag. Removal of the His-SUMO tag is accomplished during purification with treatment with SUMO protease.

Four proteins implicated in childhood genetic brain disorders have been cloned, expressed and purified. Namely, methyl-CpG-Binding Protein 2 (MeCP2; Rett Syndrome), Survival of Motor Neuron (SMN; Spinal Muscular Atrophy), Fragile X Mental Retardation Protein (FMRP; Fragile X Syndrome), and Purine Nucleoside Phosphorylase (PNP; PNP-deficiency). Cloned, expressed and purified are alpha-amylase from *Bacillus megaterium* as a therapeutic treatment for Lafora Disease, the Cas9 nuclease from *Streptococcus pyogenes*, as well as the fluorescent proteins eGFP and mCherry. Cytoplasm-sensing autorelease domains have been engineered into the DT platform in the form of cysteine protease domains from both *Clostridium difficile* toxin B and *Vibrio cholerae* MARTX toxin.

MecP2

The primary cause of Rett Syndrome, mutations in the MeCP2 gene result in a non-functional protein product. MeCP2 is a DNA-binding protein and acts as a global transcriptional regulator. Myc-MeCP2-dtA-dtB has been expressed and purified. The DNA sequence for MeCP2e1-dtA-dtB was synthesized and codon optimized for *E. coli* expression from GenScript. The Myc tag is linked to MeCP2 with a GSG linker. MeCP2 is linked to dtA with a (G4S)2 linker. MeCP2 can exist in two main isoforms, e1 and e2.

FIG. 21 demonstrates proof of cystosolic delivery of MeCP2e1 into cells by fusion protein toxicity in Vero cells. Vero cell toxicity based on Presto-Blue cell viability assay. $EC_{50}$ values for WT DT and Myc-MeCP2-DT were 0.93±1.16 and 37.33±1.13 μM, respectively.

FIG. 22 shows proof of cystosolic delivery of MecP2e1 into iPSC-derived neurons from Rett Syndrome patient fibroblasts. It shows the effect of Myc-MeCP2-DT on protein synthesis in 2 week old RTTΔ3-4 neurons as measured by $^3$H-leucine incorporation assay. $EC_{50}$ values for WT and Myc-MeCP2-DT were 4.72±1.71 and 29.56±1.39 μM, respectively.

SMN1

Spinal Muscular Atrophy (SMA) is caused by mutations in the SMN1 gene, resulting in a defective or missing protein product. Disease severity is moderated by a gene duplication event unique to humans that resulted in SMN2, a gene identical to SMN1 except for a C to T transition resulting in alternative splicing and exclusion of exon 7 from most SMN2 transcripts. Myc-SMN-dtA-dtB has been expressed and purified. The N-terminal Myc tag is linked to SMN with a GSG linker.

FIG. 23 depicts results of fusion protein toxicity assays indicating that SMN is delivered into the cytosol Vero cells. Vero cell toxicity was based on the Presto-Blue cell viability assay. The $EC_{50}$ value for SUMO-Myc-SMN-DT was 648.2±1.09 μM. Constructs can also contain the inactivating mutations K51E and E148K in dtA, when a non-toxic version is desirable.

FMRP

Fragile X Syndrome is characterized by the lack of the FMRP protein product due to the expansion of a CGG trinucleotide repeat region in the 5'UTR of the FMR1 gene. This results in hypermethylation and silencing of FMR1. FMRP is a translational regulator with many downstream gene targets. Myc-FMRP-dtA-dtB was expressed and purified. The N-terminal Myc tag is linked to FMRP with a GSG linker.

FIG. 24 depicts results of fusion protein toxicity assays indicating that SMN is delivered into the cytosol Vero cells. Vero cell toxicity was based on the Presto-Blue cell viability assay. The $EC_{50}$ value for SUMO-Myc-FMRP-DT was 4.95±1.15 μM.

PNP

PNP-deficiency is a metabolic disorder that results in immunodeficiency, as well as neurological symptoms such as developmental decline and mental retardation. The PNP enzyme catalyzes the conversion of inosine and guanosine into hypoxanthine. PNP-dtA-dtB has been expressed and purified, wherein PNP is linked to dtA with a $(G4S)_2$ linker.

FIG. 25 depicts results indicating that PNP fusion proteins have been delivered into the cytosol of Vero cells. Vero cell toxicity was based on the $^3$H-leucine incorporation assay. EC50 values for WT DT and PNP-DT were 1.31±1.11 and 145.8±1.15 μM, respectively.

FIG. 26 depicts results indicating that PNP fusion proteins have been delivered into the cytosol of two-week old wild type (WT) neurons. Toxicity was again based on the $^3$H-leucine incorporation assay. The $EC_{50}$ value for PNP-DT was 61.34±1.59 pM.

The construct dtA-PNP-dta-dtB has also been expressed and purified, wherein dtA is linked to PNP via a GSG linker and PNP is linked to dta using a GSG linker.

Cargo for Genome Editing

Cas9

The recent application of the Clustered Regularly Interspaced Short Palindromic Repeats (CRISPR) system to targeted genome editing has radically changed the field of molecular biology. The system involves the DNA endonuclease CRISPR-associated protein 9 (Cas9), which is guided to its DNA target sequence by a ~97 nt RNA molecule (gRNA). In vitro, both Cas9 and gRNA are delivered on a plasmid by transfection, while in vivo, the use of viral vectors is the preferred delivery method. There have also been reports of other delivery methods for Cas9, such as CPPs, or lipid-based methods. The construct Cas9-dtA-dtB has been expressed and purified. The Cas9 sequence is from *S. pyogenes*. Cas9 is linked to dtA with a $(G4S)_2$ linker. Cas9 is flanked on both sides by SV40 nuclear localization sequences (NLS). Cas9 is preceded by an N-terminal His tag (6×His).

FIG. 27 demonstrates delivery of Cas9 into the cytosol of Vero cells by fusion protein toxicity, as above. Vero cell toxicity was based on the 3H-leucine incorporation assay. The $EC_{50}$ values for WT DT and Cas9-DT was 1.63±1.10 and 21.74±1.09 μM, respectively.

A further version of this construct contains the inactivating mutations K51E and E148K. Cas9 is the largest cargo protein yet delivered (160 kDa).

Cargo Release

CPD

In order to release the native cargo protein upon delivery into the cytosol, a cysteine protease domain (CPD) from each of *Clostridium difficile* toxin B ($CPD_{Cd}$) and *Vibrio cholera* MARTX toxin ($CPD_{Vc}$) has been employed. The construct eGFP-$CPD_{xx}$-dtA-dtB as been expressed and purified, wherein CPDxx is either $CPD_{Vc}$ or $CPD_{Cd}$. CPD is linked to dtA with a GSG linker. Both domains undergo self-cleavage at their own N-termini upon binding of the small molecule inositol hexakisphosphate (IP6), which is exclusively located in the cytoplasm of mammalian cells. They are autoprocessing, and "self-clearing".

FIG. 28 depicts delivery of eGFP-$CPD_{Vc}$-DT into the cytosol of Vero-NlucP cells by fusion protein toxicity. Vero-NlucP cell toxicity was based on the NanoGlo assay. The $EC_{50}$ values for eGFP-$CPD_{Vc}$-DT was 54.44±1.06 μM.

Similar release constructs can be made for other cargo proteins, for example with either $CPD_{Vc}$ or $CPD_{Cd}$ and the cargo proteins described above. To date, the following CPD constructs have been made:

$CPD_{cd}$-$(G4S)_2$-dtA-dtB;

eGFP-$CPD_{vc}$-(GSG)-dtA-dtB; and eGFP-$CPD_{cd}$-(GSG)-dtA-dtB;

Data generated to date indicates that the presence of CPD results in release of (eGFP) in the presence of InsP6 i in vitro (data not shown). Western blotting data indicates that that cargo is similarly released in vivo (data not shown).

Other constructs that have been made to date include:

MeCP2-$CPD_{vc}$-$(G4S)_2$-dtA-dtB; and

PNP-$(G4S)_2$-$CPD_{cd}$-$(G4S)_3$-dtA-dtB.

These constructs are expected to be capable of releasing their cargo upon delivery to the cytosol. Non-toxic variants can be readily made, using dta in place of dtA.

Example 13

For some therapeutic applications, it may be desirable to reduce the immunogenicity of DT domains. To this end, DT domains could be mutated, e.g., to reduce their antigenicity, for example by removing T-cell epitopes.

Example 14

For some applications, it may be advantageous to reduce the size of the construct, e.g. to provide a smaller construct and/or to reduce potential for antigenicity. Experiments were conducted to assess the function of the DTA domain.

Materials and Methods

Constructs

The glucosyl transferase domain (GTD; SEQ ID NO: 26) from *Clostridium difficile* toxin B was linked to dta or Δdta-dtB via a GSG linker to generate the constructs GTD-dta-dtB and GTD-Δdta-dtB. The latter retains a small DTA fragment (Δdta); most of the functional domain proper has been deleted, leaving SEQ ID NO: 28. Δdta thus extends from a cysteine corresponding to position 186 of SEQ ID NO: 1 through its C-terminus. This cysteine residue was retained as it is involved in disulphide bond formation. The CPD domain from *Vibrio cholerae* was subsequently cloned between GTD and dtB upstream of the linker yielding the construct GTD-CPD-Δdta-dtB with no linker sequence between the GTD and CPD domains. All three constructs were cloned with an N-terminal polyhistidine tag and a C-terminal Strep-tag™ II sequence (SEQ ID NO: for affinity purification using the GE-Healthcare StrepTactin™ purification system.

Expression and Purification

GTD DT chimeras were expressed as N-terminal His-tagged proteins in *E. coli* BL21(DE3) cells, induced with 1 mM isopropyl-β-d-1-thiogalactopyranoside (IPTG) for 4 hours at 21° C. Cells were harvested by centrifugation, re-suspended in lysis buffer (20 mM Tris-HCl pH 8.0, 0.5 M NaCl, 20 mM imidazole, benzonase, lysozyme and Protease inhibitor cocktail) and lysed by an EmulsiFlex C3 microfluidizer (Avestin) at 15,000 psi. The lysates were centrifuged at 18,000×g for 20 minutes. His-tagged proteins were purified by Ni-affinity chromatography using a His-Trap FF column (GE-Healthcare). Protein was eluted in 20 mM Tris-HCl pH 8.0, 0.5 M NaCl and 125 mM imidazole and loaded directly onto a 5 mL StrepTrap HP column (GE-Healthcare). Pure protein was then eluted from the Strep-Trap HP column in 20 mM Tris-HCl pH 8.0, 150 mM NaCl and 2.0 mM desthiobiotin.

Cell Viability Assay

Vero cells were plated at 4000 cells/well in a 96-well cell culture plate and allowed to attach overnight at 37° C. and 5% $CO_2$. The next day, fusion toxins were added at various concentrations in DMEM (10% FBS, 1% penicillin/streptomycin). After 48 hours, 100 µl of Presto-Blue (Life Technologies) cell viability dye was added to all wells and incubated at 37° C. for 2 hours. Fluorescence was measured in a SpectraMax M5e microplate reader (Molecular Devices) (Ex/Em 555/585 nm). Results were quantified and fit to a sigmoidal function in GraphPad Prism.

Results and Discussion

Delivery of Cargo in the Absence of the Catalytic A Domain of DT

Inhibition of protein synthesis by DTA has been a useful tool to demonstrate delivery of cargo-DTA chimeras to the cytosol, but tethering to DTA may interfere with certain cargo protein's activity through steric interference and/or cellular localization in some applications. While inclusion of a cysteine protease domain between cargo and DTA would allow for release of native cargo protein, a question remained of whether cargo could be fused more directly to the DTB domain, i.e. with less of DTA, thereby decreasing the size and complexity of cargo being delivered into the cell. Reducing or eliminating the A domain would have the additional benefit of reducing the potential for immunogenicity in future in vivo applications of this technology. Fusion proteins containing the glucosyltransferase domain (GTD) from *Clostridium difficile* fused to dta-dtB, CPD-Δdta-dtB or simply Δdta-dtB were cloned, expressed and purified. Upon reaching the cytosol, the GTD inactivates small Rho family GTPases (Rac1, RhoA, Cdc42), thereby disrupting actin cytoskeleton organization resulting in an acute rounding phenotype and eventual apoptosis (Just 1995). In the absence most of the DTA domain, the cytotoxicity of the GTD was used to compare its cytosolic entry in these three different delivery paradigms.

Figure 29:
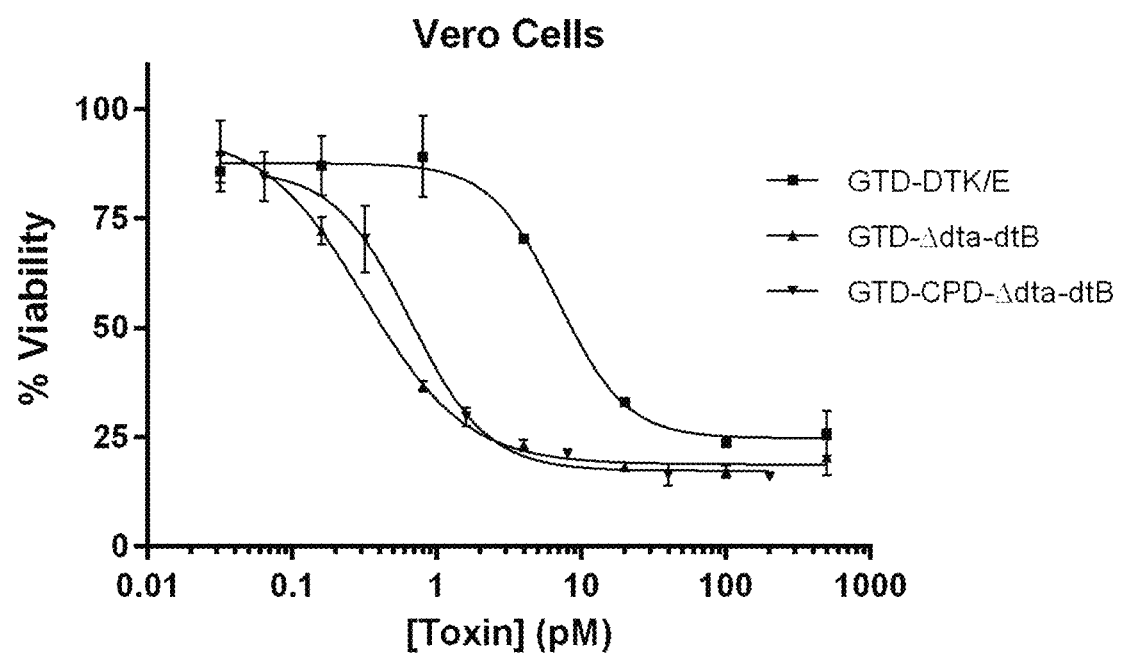

FIG. 29 shows the effect of removing most of the A domain, which appears to have no effect on the ability of the GTD cargo to reach the cytosol. Remarkably, there is a small increase in toxicity of the two constructs lacking most of the DTA domain, however, this difference is small and could be due to an effect on the enzymatic activity of GTD as both GTD-Δdta-CPD-dtB and GTD-Δdta-dtB result in delivery of free GTD while GTD-dta remain fused upon delivery.

The dispensable nature of the DTA domain in cargo translocation has important implications for the DT delivery platform and speaks to the versatility and modularity of this system. This finding also deviates significantly from the widely accepted model of DT translocation, in which DTA is absolutely required and is thought to make up part of the translocation machinery.

Example 15

Introduction

Since the discovery of first mutations in Ras genes in various human cancers in 1982, Ras has been the major focus in cancer research. It is now well known that the three Ras genes (KRas, NRas and HRas) constitute the most frequently mutated oncogene family in human cancer and mutations in these Ras genes are found in 20-30% of all human cancers, placing the Ras variants among the most prevalent drivers of cancer[26, 27]. Despite the frequent involvement of Ras in the onset and progression of cancer, efficient inhibition of oncogenic Ras with small molecules has been very difficult due to their relatively smooth, unpocketed surface and high affinity for its substrate. Moreover, attempts to inhibit downstream effector pathways showed only limited success owing to development of drug resistance and complex feedback mechanisms[28]. To date, clinically effective anti-Ras therapies remain elusive, prompting a perception that Ras may be undruggable.

Recently, a bacterially-derived enzyme was identified that specifically degrades Ras proteins in human cells. Ectopic expression of this enzyme, RRSP (Ras/Rap1-specific endopeptidase), was shown to cleave mutant KRas, NRas and HRas and inhibit cell growth[29], leading to the hypothesis that this enzyme could halt cancer progression in cells with unregulated Ras activity. However, this enzyme would not be an effective anti-cancer biologic unless it is able to reach its target—Ras—which is tethered in the inner leaflet of plasma membranes in the cytosol of cells. Herein is described an intracellular protein delivery platform, which introduces impermeable proteins into the cytosol of target cells. The protein delivery platform is based on a bacterial toxin, called diphtheria toxin (DT) which has an intrinsic mechanism to cross plasma membranes and reach the cytosol of specific cells with high efficiency.

The ability of DT to cross cell membranes and deliver proteins with varying structures, sizes and stabilities as N-terminal fusions into mammalian cells using a detoxified toxin, rendered it an ideal delivery vector for protein therapeutics. The goal of this example is to use the nontoxic variant of DT (denoted as dta-dtB, where dta contains two mutations, K51E and E148K in the dtA domain) as a cytosolic delivery platform to deliver RRSP into the cytosol of cancer cells and inhibit cancer growth and progression.

Materials and Methods

Cell Lines and Media

HeLa epithelial cells were cultured in Eagle's Minimum Essential Medium (EMEM, Wisent Bioproducts). HCT116 colorectal cancer cells were cultured in McCoy's 5A medium (Wisent Bioproducts). BxPC3, CFPACI, and HPAFII cells were cultured in RPMI1640. All media were supplemented with 10% fetal bovine serum, 100 U/mL penicillin, and 100 µg/mL streptomycin (Wisent Bioproducts). RealTime-Glo MT Cell Viability Assay was obtained from Promega Corporation.

Generation of RRSP-DT Chimeras

Point mutations were made in the DT E148S plasmid using QuikChange Lightning Multi Site-Directed Mutagenesis Kit (Agilent Technologies) to prepare catalytically inactive DT (dta-dtB). A plasmid containing RRSP DNA sequences was a kind gift of Dr. Karla J. F. Satchell (Northwestern University, Chicago, Ill.). RRSP DNA sequences were amplified (see, e.g. SEQ ID NO: 26 for the coding sequence) and integrated into the dta-dtB plasmid using Gibson Assembly (New England BioLabs) to generate RRSP-dta-dtB. RRSP fused to dtB (RRSP-dtB) and to the receptor domain alone (RRSP-dtR) (i.e., without the translocation domain in the B domain) were generated in the same manner as RRSP-dta-dtB.

Expression and Purification of RRSP-DT Chimera

RRSP (SEQ ID NO: 27) and RRSP fusion proteins were expressed as N-terminal His-Sumo-tagged and C-terminal Strep-tagged II proteins in *E. coli* NiCo21 (DE3). Overnight cultures were diluted in 1:30 in fresh Terrific Broth containing 50 pg/ml kanamycin and grown to OD600=0.8 at 37° C. before inducing the cultures with 1 mM isopropyl-β-D-1-thiogalactopyranoside (IPTG) for 5 h at 25° C. *E. coli* cells were harvested by centrifugation at 5,500 rpm and resuspended in lysis buffer (20 mM Tris-HCl pH 8.0, 500 mM NaCl, 20 mM imidazole, benzonase, lysozyme and protease inhibitor cocktail) and lysed by an EmulsiFlex C3 microfluidizer (Avestin) at 15,000 psi. The lysates were centrifuged at 14,000 g for 20 mins. His-Sumo-tagged proteins were purified by Ni-affinity chromatography using a His-Trap Crude FF column (GE Healthcare). Proteins were further purified using a StrepTrap HP column (GE Healthcare). After the second purification, the His-Sumo tag was removed by adding 1U of Sumo Protease to 90 pg of purified proteins in 20 mM Tris-HCl pH 8.0, 150 mM NaCl and 10 mM imidazole. The cleavage reaction mixture was incubated at 30° C. for 1 h followed by purification using His-Pure Ni-NTA resin (Thermo Scientific) to remove the His-Sumo protease and His-Sumo tag from the purified RRSP and RRSP fusion proteins. Purified proteins were concentrated using Millipore Amicon Ultra 50K spin concentrators and glycerol was added so that the final buffer was 20 mM Tris-HCl pH 8.0, 150 mM NaCl, 10 mM imidazole, 8% glycerol. Protein concentration was determined using a nanophotometer (Implen) and purity was estimated using SDS-PAGE. Proteins were stored at −80° C. until used.

Intoxication of Cells with RRSP-DT Chimeras

HeLa cells were seeded at $2 \times 10^5$ cells/well overnight into a 6-well plate. HCT116 cells were seeded at $3 \times 10^5$ cells/well for 48 h. Before intoxication, the media was exchanged for fresh media and then indicated toxin concentrations were added to the media and incubated for the times indicated in the legend at 37° C. with 5% CO2.

Western Blotting

A total of $3-4 \times 10^5$ treated cells were washed with PBS and resuspended in 80 µl of lysis buffer (20 mM Tris-HCl pH 8.0, 150 mM NaCl, 1% Triton X-100). 30 µl of lysate was resuspended in 10 µl of 4×Laemmli sample buffer and boiled for 10 min. Forty microliters of lysate were separated by SDS-PAGE and transferred to nitrocellulose (Amersham), blocked with 5% milk/Tris-buffered saline containing 0.1% Tween-20 (TBST) for 1 h at room temperature, and probed with a 1/1,000 dilution of pan-Ras mouse mAb RAS10 (05-516, EMD Millipore) and actin mouse mAb AC-40 (Sigma-Aldrich). Following an overnight incubation with the primary antibodies, the blot was washed with TBS-T and incubated with a 1/5,000 dilution of anti-mouse horseradish peroxidase for 1 hr. After the final washes in TBST, chemiluminescent detection was carried out using SuperSignal West Femto substrate (Thermo Pierce) and imaged in ChemiDoc MP Imaging System (BioRad).

RealTime-Glo Assay

BxPC3 pancreatic adenocarcinoma cells (625 cells/well) were plated in 40-ul media containing 2× RealTime-Glo reagents in a 96-well white, clear flat bottom plate (Corning). RRSP-dtB titration was prepared at 2× concentrations in media and added to the plate at an equal volume. Luminescence was read at 1, 4, 9, 24, 48 and 72 h post toxin addition on a SpectraMax M5 plate reader.

Results

Figure 30:
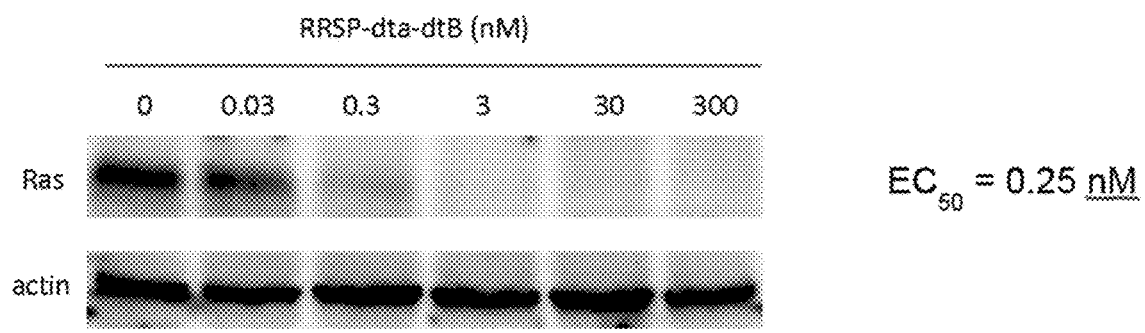
FIG. 30 depicts results of RRSP delivery into the cytosol of HeLa cells by a non-toxic DT(dta that diphtheria toxin can, in some embodiments, deliver an impressive array of passenger proteins spanning a range of sizes, structures and stabilities into cells in a manner that indicates that they are 'invisible' to the translocation machinery. Further, it is shown that α-amylase can be delivered into cells by a detoxified diphtheria toxin chimera, and that it digests intracellular glycogen in live cells, providing evidence that delivered cargo can be folded, active and abundant. The efficiency and versatility of diphtheria toxin over existing systems open numerous possibilities for intracellular delivery of bioactive proteins.
Figure 31:
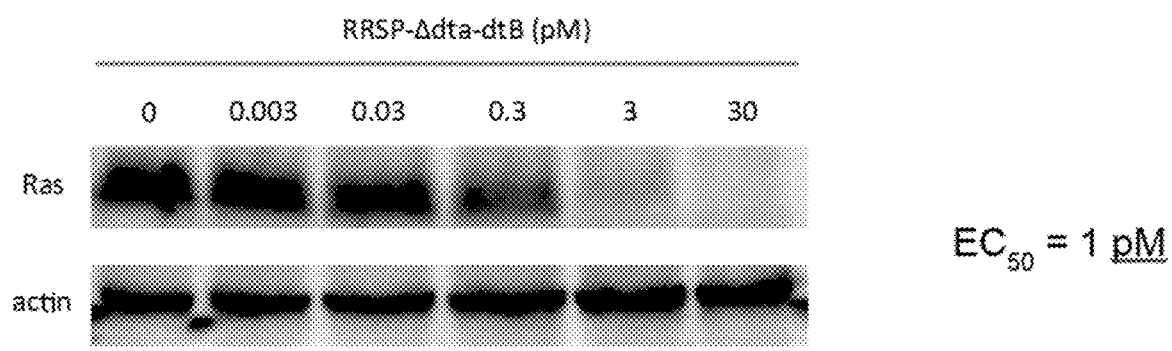
Figure 32:
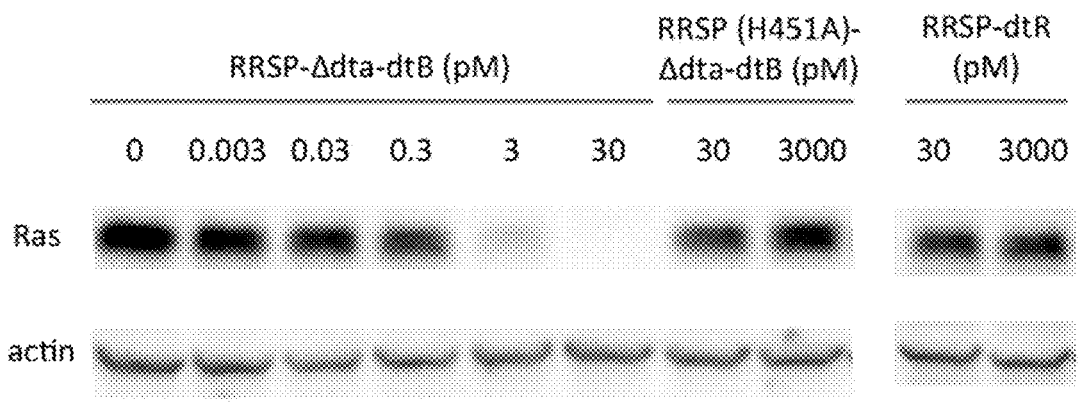
Figure 33:
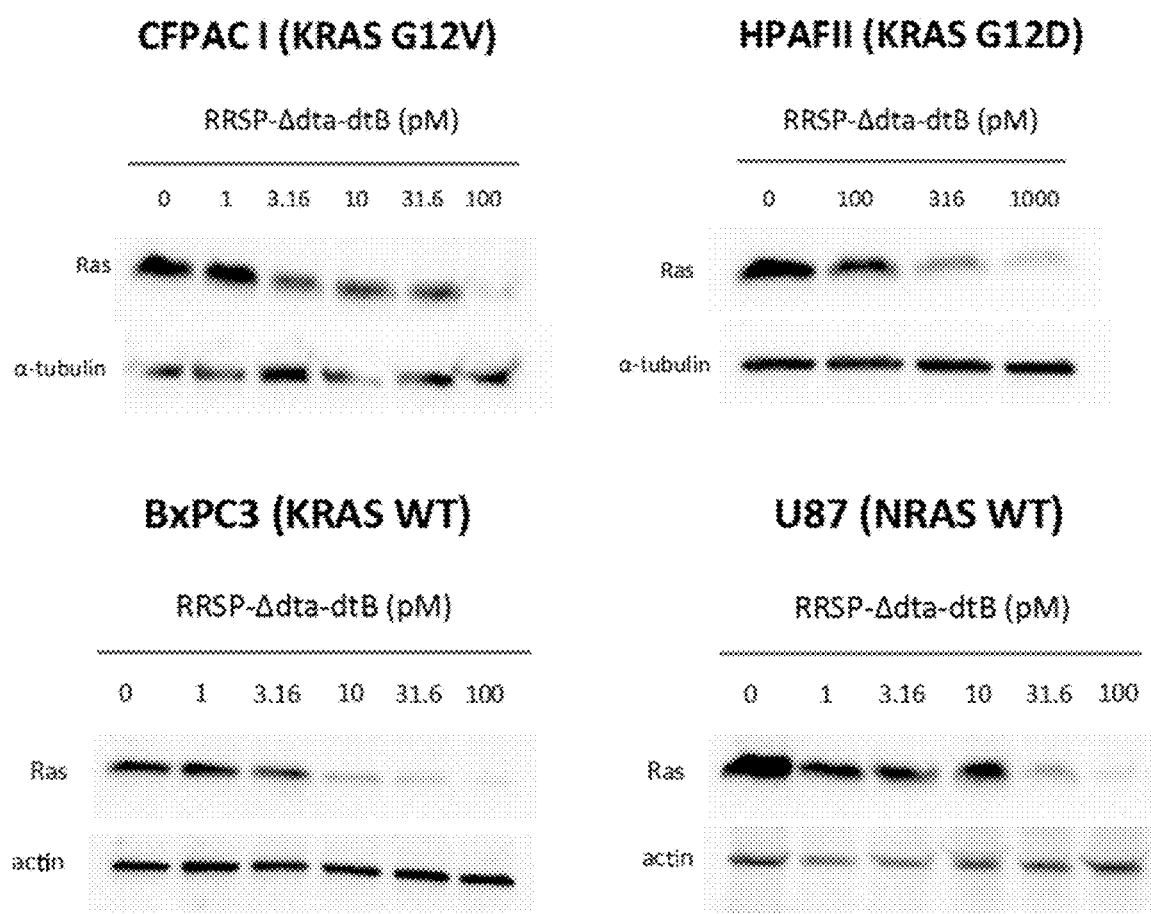
Figure 34:
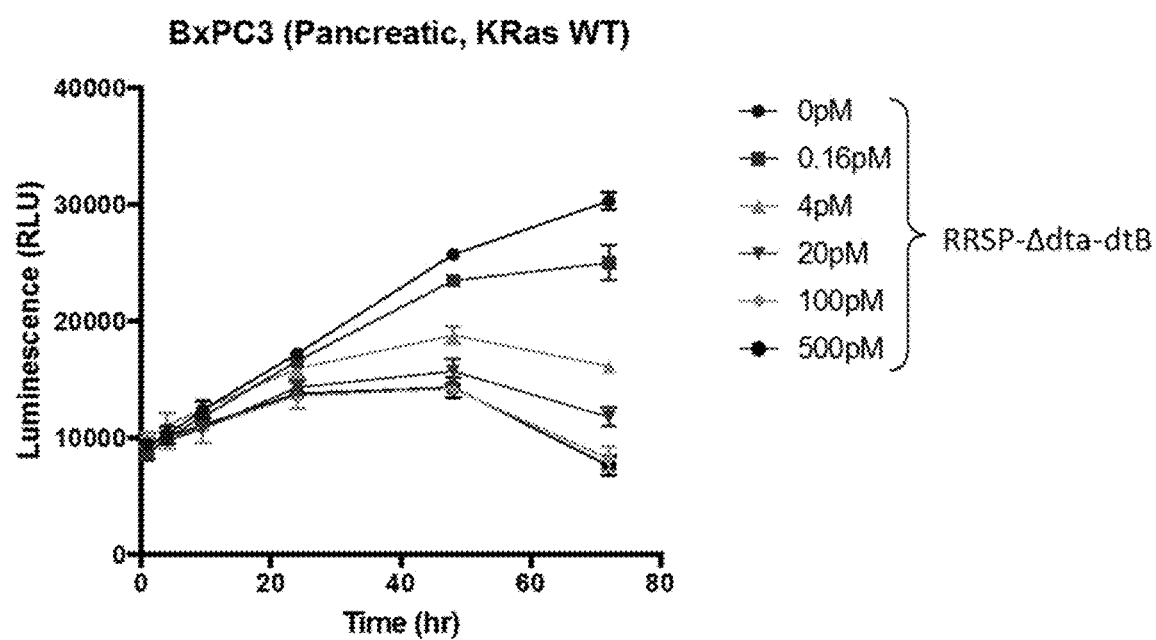

A chimeric protein consisting of RRSP fused to a nontoxic variant of DT (RRSP-dta-dtB) with an intervening $(G_4S)_2$ linker was generated. Upon 24 h incubation of RRSP-dta-dtB on HeLa cells, a complete loss of total RAS proteins inside cells was detected at a sub-nanomolar concentration of the enzyme (EC50=0.25 nM), as measured by immunoblotting with anti-RAS antibody (FIG. 30). To improve the RAS cleavage efficiency, the delivery platform was optimized by either removing the dta domain or inserting the Auto-Processing Domain (APD) in between RRSP and dtB. In both cases, 14 amino acid residues from the C-terminus of the dta domain, denoted as Δdta, were maintained to conserve the disulfide bond and the furin cleavage site, essential for toxin entry into cells. The resulting constructs were represented as RRSP-Δdta-dtB and RRSP-APD-Δdta-dtB, respectively, and a $(G_4S)_2$ linker was introduced between RRSP and Δdta and between RRSP and APD. Remarkably, these second generation constructs were 300 times more potent than the first generation construct with an EC50 of 1 µM in HeLa cells (FIG. 31). The results demonstrated for the first time that the dtB domain with virtually all of the dta domain removed is sufficient to deliver active RRSP inside cells. As further demonstration that RRSP-Δdta-dtB could be used as a potential cancer therapeutic, the ability of RRSP-Δdta-dtB to degrade RAS in cancer cell lines bearing common RAS point mutations was tested. Intoxicating HCT116 colorectal carcinoma cells, which express KRAS with a G13D mutation, with RRSP-Δdta-dtB resulted in undetectable levels of RAS at a picomolar concentration of the enzyme (FIG. 32). The effect of RAS cleavage was solely due to the activity of RRSP, as its inactive mutant control (RRSP_H451A) did not affect intracellular RAS levels. Moreover, as expected, RRSP fused to the receptor-binding domain of DT (RRSP-dtR) did not cleave RAS in HCT116 cells as it lacks the ability to translocate RRSP into the cytosol. Mutant KRAS proteins in cancer cell lines (CFPACI-G12V and HPAFII-G12D) were likewise degraded, demonstrating that RRSP can effectively intoxicate cells with activating RAS mutations (FIG. 33). To investigate whether the cleavage of RAS in RRSP-Δdta-dtB-treated cells would lead to disruption in cell proliferation, a cell proliferation assay was performed. BxPC3 pancreatic cancer cells were intoxicated at varying concentrations of RRSP-Δdta-dtB and luminescence emitted by live cells was recorded at 1, 4, 9, 24, 48, or 72 h post toxin addition. As shown in FIG. 34, untreated cells showed steady increase in luminescence over the course of 72 hours, indicating cellular proliferation. In contrast, a decrease in luminescence was observed in RRSP-Δdta-dtB-treated cells, and the most significant impairment in proliferation was found in cells treated with the highest enzyme concentration, indicating that the cleavage of RAS led to reduced cellular proliferation.

Discussion

RAS proteins are small GTPases, which serve as a crucial signaling hub that regulates various cellular processes, including proliferation, survival and differentiation. The discovery of constitutively activating RAS mutations in human tumors has initiated intense research on RAS, yet, to date, none of the RAS-targeted drugs have shown clinical efficacy. Recently, an effector domain of the multifunctional-autoprocessing repeats-in-toxin (MARTX) toxin from *Vibrio vulnificus* that specifically cleaves the Switch I region of all three isoforms of RAS proteins has been identified, and the enzyme has been named RRSP. In order to achieve its full therapeutic efficacy, however, RRSP must reach the cytosol of cancer cells where mutant RAS proteins are present.

Here, it was demonstrated that using an engineered DT, active RRSP was successfully delivered into the cytosol of cancer cells and degraded RAS with extremely high efficiency. It was also demonstrated that the optimization of the DT-based delivery platform resulted in ~300-fold increase in potency. Importantly, several cancer cell lines carrying common RAS mutations were also efficiently cleaved by the intracellularly-delivered RRSP.

Collectively, the results demonstrate the great potential of RRSP as an anti-RAS cancer therapy. In particular the surprising increase in potency achieved is such that this construct is expected to be amenable to in vivo and/or therapeutic applications.

In the preceding description, for purposes of explanation, numerous details are set forth in order to provide a thorough understanding of the embodiments. However, it will be apparent to one skilled in the art that these specific details are not required. In other instances, well-known electrical structures and circuits are shown in block diagram form in order not to obscure the understanding. For example, specific details are not provided as to whether the embodiments described herein are implemented as a software routine, hardware circuit, firmware, or a combination thereof.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole.

REFERENCES

1 Williams, D. P. et al. Diphtheria toxin receptor binding domain substitution with interleukin-2: genetic construction and properties of a diphtheria toxin-related interleukin-2 fusion protein. Protein engineering 1, 493-498 (1987).
2 Jean, L. F. & Murphy, J. R. Diphtheria toxin receptor-binding domain substitution with interleukin 6: genetic construction and interleukin 6 receptor-specific action of a diphtheria toxin-related interleukin 6 fusion protein. Protein engineering 4, 989-994 (1991).
3 Aullo, P. et al. A recombinant diphtheria toxin related human CD4 fusion protein specifically kills HIV infected cells which express gp120 but selects fusion toxin resistant cells which carry HIV. The EMBO journal 11, 575-583 (1992).
4 Madshus, I. H., Olsnes, S. & Stenmark, H. Membrane translocation of diphtheria toxin carrying passenger protein domains. Infection and immunity 60, 3296-3302 (1992).
5 Stenmark, H., Moskaug, J. O., Madshus, I. H., Sandvig, K. & Olsnes, S. Peptides fused to the amino-terminal end of diphtheria toxin are translocated to the cytosol. The Journal of cell biology 113, 1025-1032 (1991).
6 Wiedlocha, A., Madshus, I. H., Mach, H., Middaugh, C. R. & Olsnes, S. Tight folding of acidic fibroblast growth factor prevents its translocation to the cytosol with diphtheria toxin as vector. The EMBO journal 11, 4835-4842 (1992).
7 Klingenberg, O. & Olsnes, S. Ability of methotrexate to inhibit translocation to the cytosol of dihydrofolate reductase fused to diphtheria toxin. The Biochemical journal 313 (Pt 2), 647-653 (1996).
8 Ainavarapu, S. R., Li, L., Badilla, C. L. & Fernandez, J. M. Ligand binding modulates the mechanical stability of dihydrofolate reductase. Biophysical journal 89, 3337-3344, doi:10.1529/biophysj.105.062034 (2005).
9 Francis, J. W. et al. A survival motor neuron:tetanus toxin fragment C fusion protein for the targeted delivery of SMN protein to neurons. Brain research 995, 84-96 (2004).
10 Fu, H., Blanke, S. R., Mattheakis, L. C. & Collier, R. J. Selection of diphtheria toxin active-site mutants in yeast. Rediscovery of glutamic acid-148 as a key residue. Advances in experimental medicine and biology 419, 45-52 (1997).
11 Murphy, J. R. Mechanism of diphtheria toxin catalytic domain delivery to the eukaryotic cell cytosol and the cellular factors that directly participate in the process. Toxins 3, 294-308, doi:10.3390/toxins3030294 (2011).
12 Kiyokawa, T., Williams, D. P., Snider, C. E., Strom, T. B. & Murphy, J. R. Protein engineering of diphtheria-toxin-related interleukin-2 fusion toxins to increase cytotoxic potency for high-affinity IL-2-receptor-bearing target cells. Protein engineering 4, 463-468 (1991).
13 Choudhary, S., Mathew, M. & Verma, R. S. Therapeutic potential of anticancer immunotoxins. Drug discovery today 16, 495-503, doi:10.1016/j.drudis.2011.04.003 (2011).
14 Alewine, C., Hassan, R. & Pastan, I. Advances in Anticancer Immunotoxin Therapy. The oncologist, doi: 10.1634/theoncologist.2014-0358 (2015).
15 Mazor, R. et al. Identification and elimination of an immunodominant T-cell epitope in recombinant immunotoxins based on *Pseudomonas* exotoxin A. Proc Natl Acad Sci USA 109, E3597-3603, doi:10.1073/pnas.1218138109 (2012).
16 Ballard, J. D., Collier, R. J. & Starnbach, M. N. Anthrax toxin-mediated delivery of a cytotoxic T-cell epitope in vivo. Proceedings of the National Academy of Sciences of the United States of America 93, 12531-12534 (1996).
17 Leppla, S. H., Arora, N. & Varughese, M. Anthrax toxin fusion proteins for intracellular delivery of macromolecules. Journal of applied microbiology 87, 284 (1999).
18 Bachran, C. et al. Anthrax toxin-mediated delivery of the *Pseudomonas* exotoxin A enzymatic domain to the cytosol of tumor cells via cleavable ubiquitin fusions. mBio 4, e00201-00213, doi:10.1128/mBio.00201-13 (2013).
19 Liao, X., Rabideau, A. E. & Pentelute, B. L. Delivery of antibody mimics into mammalian cells via anthrax toxin protective antigen. Chembiochem: a European journal of chemical biology 15, 2458-2466, doi:10.1002/cbic.201402290 (2014).
20 Benson, E. L., Huynh, P. D., Finkelstein, A. & Collier, R. J. Identification of residues lining the anthrax protective antigen channel. Biochemistry 37, 3941-3948, doi:10.1021/bi972657b (1998).
21 Krantz, B. A. et al. A phenylalanine clamp catalyzes protein translocation through the anthrax toxin pore. Science 309, 777-781, doi:10.1126/science.1113380 (2005).
22 Zornetta, I. et al. Imaging the cell entry of the anthrax oedema and lethal toxins with fluorescent protein chimeras. Cellular microbiology 12, 1435-1445, doi:10.1111/j.1462-5822.2010.01480.x (2010).
23 Nagata, S. & Pastan, I. Removal of B cell epitopes as a practical approach for reducing the immunogenicity of foreign protein-based therapeutics. Advanced drug delivery reviews 61, 977-985, doi:10.1016/j.addr.2009.07.014 (2009).
24 King, C. et al. Removing T-cell epitopes with computational protein design. Proc Natl Acad Sci USA 111, 8577-8582, doi:10.1073/pnas.1321126111 (2014).
25. Just I, Selzer J, Wilm M, von Eichel-Streiber C, Mann M, Aktories K (1995) Glucosylation of Rho proteins by *Clostridium difficile* toxin B. (1995) Nature 8: 500-503.
26. Forbes, S. A., et al., COSMIC: mining complete cancer genomes in the Catalogue of Somatic Mutations in Cancer. Nucleic Acids Res, 2011. 39 (Database issue): p. D945-50.
27. Prior, I. A., P. D. Lewis, and C. Mattos, A comprehensive survey of Ras mutations in cancer. Cancer Res, 2012. 72(10): p. 2457-67.
28. Lito, P., N. Rosen, and D. B. Solit, *Tumor adaptation and resistance to RAF inhibitors*. Nat Med, 2013. 19(11): p. 1401-9.
29. Antic, I., et al., Site-specific processing of Ras and Rap1 Switch I by a MARTX toxin effector domain. Nat Commun, 2015. 6: p. 7396.

All references are incorporated by reference herein to the same extent as if set forth verbatim herein.

---

The invention claimed is:

1. A recombinant molecule comprising a cargo polypeptide, a diphtheria toxin enzymatic fragment (DTA), and a diphtheria toxin translocation fragment (DTB), having a general structure:

x-C-y-DTA-DTB wherein:
x is a polypeptide or absent,
C is the cargo polypeptide, and
wherein the diphtheria toxin enzymatic fragment is linked to the diphtheria toxin
translocation fragment by way of a disulphide linkage,
wherein y is a polypeptide comprising an autoprocessing domain,
wherein the DTA comprises the amino acid sequence-SEQ ID No: 28, and
wherein the DTB comprises the amino acid sequence-SEQ ID No: 4.

2. The recombinant molecule of claim 1, wherein the autoprocessing domain is SEQ ID No: 20 or 21.

3. The recombinant molecule of claim 1, wherein the DTA comprises the amino acid sequence SEQ ID No: 1.

4. The recombinant molecule of claim 1, wherein the DTA is catalytically inactive.

5. The recombinant molecule of claim 4, wherein the diphtheria toxin enzymatic fragment comprises an amino acid sequence bearing the mutations K51E and E148K, as numbered with respect to SEQ ID No: 1.

6. The recombinant molecule of claim 1, wherein the DTA comprises the amino acid sequence SEQ ID No: 2.

7. The recombinant molecule of claim 1, wherein the cargo polypeptide comprises an enzyme.

8. The recombinant molecule of claim 4, wherein the cargo polypeptide comprises a therapeutic polypeptide.

9. The recombinant molecule of claim 4, wherein the cargo polypeptide comprises MecP2, SMN, FMRP, PNP, alpha-amylase, a zinc finger nuclease, a transcription activator-like effector nuclease, a clustered regularly interspaced short palindromic repeat protein, or an active fragment thereof.

10. The recombinant molecule of claim 9, wherein the clustered regularly interspaced short palindromic repeat protein is Cas9.

11. The recombinant molecule of claim 4, wherein the cargo protein is a Ras/Rap1-specific endopeptidase (RRSP) from *Vibrio vulnificus*, a functional fragment thereof, or a homologue thereof.

12. The recombinant molecule of claim 1, wherein the cargo polypeptide has a molecular weight of greater than 50 kDa.

13. The recombinant molecule of claim 1, wherein the DTA is a C-terminal fragment of SEQ ID No: 1 comprising the cysteine corresponding to position 186 of SEQ ID No: 1.

14. The recombinant molecule of claim 13, wherein the DTA consists of the amino acid sequence CAGNRVRRS-VGSSL (SEQ ID No: 28).

15. The recombinant molecule of claim 1, where the polypeptide of y additionally comprises one or more amino acid linker.

16. A nucleic acid encoding the recombinant molecule of claim 1.

17. The nucleic acid of claim 16, wherein diphtheria toxin enzymatic fragment and diphtheria toxin translocation fragment are encoded separately.

18. A pharmaceutical composition comprising the recombinant molecule of claim 1, and a pharmaceutically acceptable carrier.

19. The recombinant molecule of claim 1, wherein the DTB consists of the amino acid sequence SEQ ID No: 4.

20. The recombinant molecule of claim 1, wherein the DTB comprises the amino acid sequence SEQ ID No: 3.

21. The recombinant molecule of claim 1, wherein:
the cargo polypeptide is a Ras/Rap1-specific endopeptidase (RRSP) from *Vibrio vulnificus*, a functional fragment thereof, or a homologue thereof;
the DTA consists of the amino acid sequence SEQ ID No: 28 and
the DTB consists of the amino acid sequence SEQ ID No: 4.

* * * * *

UNITED STATES PATENT AND TRADEMARK OFFICE
CERTIFICATE OF CORRECTION

PATENT NO.        : 10,597,663 B2
APPLICATION NO.   : 15/827595
DATED             : March 24, 2020
INVENTOR(S)       : Roman A. Melnyk et al.

It is certified that error appears in the above-identified patent and that said Letters Patent is hereby corrected as shown below:

In the Specification

In Column 28, between Lines 53 and 54, insert:
--For protein determination cells were lysed on ice in RIPA buffer (150 mM NaCl, 20 mM Tris, 12.1 mM deoxycholate, 1% triton X-100, 0.1% SDS). Following centrifugation (14,000 × g, 4° C., 15 min) the supernatant was subjected to protein determination using the DC™ protein assay (Bio-Rad) following the manufacturer's instructions.--

In Column 28, Line 66, delete:
"For glycogen determination cells were incubated for 45 min in 0.5 M KOH at 98° C. with intermittent mixing to lyse cells and extract glycogen. Following neutralization with 2 M acetic acid glycogen was digested in an aliquot overnight at 55° C. with 0.5 U amyloglucosidase (Sigma) and subsequently determined as free glucose according to Lowry and Passonneau (1972) with an enzymatic assay that detects NADPH by incubating the sample with hexokinase (Roche), glucose 6-phosphate dehydrogensae (Roche), ATP (Sigma), and NADP (Roche). Glucose in undigested extracts was consistently below the limit of detection."

Signed and Sealed this
Third Day of November, 2020

Andrei Iancu
*Director of the United States Patent and Trademark Office*

SEQUENCE LISTING

```
<160> NUMBER OF SEQ ID NOS: 30

<210> SEQ ID NO 1
<211> LENGTH: 199
<212> TYPE: PRT
<213> ORGANISM: Corynebacterium diphtheriae
<220> FEATURE:
<221> NAME/KEY: MISC_FEATURE
<223> OTHER INFORMATION: dtA Domain

<400> SEQUENCE: 1

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Gly Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160
```

Val Glu Leu Glu Ile Asn Phe Glu Thr Arg Gly Lys Arg Gly Gln Asp
            165                 170                 175

Ala Met Tyr Glu Tyr Met Ala Gln Ala Cys Ala Gly Asn Arg Val Arg
        180                 185                 190

Arg Ser Val Gly Ser Ser Leu
        195

<210> SEQ ID NO 2
<211> LENGTH: 199
<212> TYPE: PRT
<213> ORGANISM: Corynebacterium diphtheriae
<220> FEATURE:
<221> NAME/KEY: MISC_FEATURE
<223> OTHER INFORMATION: dta Domain (K51E, E148K)

<400> SEQUENCE: 2

Gly Ala Asp Asp Val Val Asp Ser Ser Lys Ser Phe Val Met Gl

```
Glu Glu Phe His Gln Thr Ala Leu Glu His Pro Glu Leu Ser Glu Leu
 50                  55                  60
Lys Thr Val Thr Gly Thr Asn Pro Val Phe Ala Gly Ala Asn Tyr Ala
 65                  70                  75                  80
Ala Trp Ala Val Asn Val Ala Gln Val Ile Asp Ser Glu Thr Ala Asp
                 85                  90                  95
Asn Leu Glu Lys Thr Thr Ala Ala Leu Ser Ile Leu Pro Gly Ile Gly
            100                 105                 110
Ser Val Met Gly Ile Ala Asp Gly Ala Val His His Asn Thr Glu Glu
            115                 120                 125
Ile Val Ala Gln Ser Ile Ala Leu Ser Ser Leu Met Val Ala Gln Ala
130                 135                 140
Ile Pro Leu Val Gly Glu Leu Val Asp Ile Gly Phe Ala Ala Tyr Asn
145                 150                 155                 160
Phe Val Glu Ser Ile Ile Asn Leu Phe Gln Val Val His Asn Ser Tyr
                165                 170                 175
Asn Arg Pro Ala Tyr Ser Pro Gly His Lys Thr Gln Pro Phe Leu His
            180                 185                 190
Asp Gly Tyr Ala Val Ser Trp Asn Thr Val Glu Asp Ser Ile Ile Arg
            195                 200                 205
Thr Gly Phe Gln Gly Glu Ser Gly His Asp Ile Lys Ile Thr Ala Glu
210                 215                 220
Asn Thr Pro Leu Pro Ile Ala Gly Val Leu Leu Pro Thr Ile Pro Gly
225                 230                 235                 240
Lys Leu Asp Val Asn Lys Ser Lys Thr His Ile Ser Val Asn Gly Arg
                245                 250                 255
Lys Ile Arg Met Arg Cys Arg Ala Ile Asp Gly Asp Val Thr Phe Cys
            260                 265                 270
Arg Pro Lys Ser Pro Val Tyr Val Gly Asn Gly Val His Ala Asn Leu
            275                 280                 285
His Val Ala Phe His Arg Ser Ser Glu Lys Ile His Ser Asn Glu
290                 295                 300
Ile Ser Ser Asp Ser Ile Gly Val Leu Gly Tyr Gln Lys Thr Val Asp
305                 310                 315                 320
His Thr Lys Val Asn Ser Lys Leu Ser Leu Phe Phe Glu Ile Lys Ser
                325                 330                 335
Arg Gln Ala

<210> SEQ ID NO 4
<211> LENGTH: 179
<212> TYPE: PRT
<213> ORGANISM: Corynebacterium diphtheriae
<220> FEATURE:
<221> NAME/KEY: MISC_FEATURE
<223> OTHER INFORMATION: dtT (dtB Translocation Domain)

<400> SEQUENCE: 4

Ser Cys Ile Asn Leu Asp Trp Asp Val Ile Arg Asp Lys Thr L

Lys Thr Val Thr Gly Thr Asn Pro Val Phe Ala Gly Ala Asn Tyr Ala
65                  70                  75                  80

Ala Trp Ala Val Asn Val Ala Gln Val Ile Asp Ser Glu Thr Ala Asp
            85                  90                  95

Asn Leu Glu Lys Thr Thr Ala Ala Leu Ser Ile Leu Pro Gly Ile Gly
            100                 105                 110

Ser Val Met Gly Ile Ala Asp Gly Ala Val His His Asn Thr Glu Glu
            115                 120                 125

Ile Val Ala Gln Ser Ile Ala Leu Ser Ser Leu Met Val Ala Gln Ala
            130                 135             140

Ile Pro Leu Val Gly Glu Leu Val Asp Ile Gly Phe Ala Ala Tyr Asn
145                 150                 155                 160

Phe Val Glu Ser Ile Ile Asn Leu Phe Gln Val Val His Asn Ser Tyr
                165                 170                 175

Asn Arg Pro

<210> SEQ ID NO 5
<211> LENGTH: 179
<212> TYPE: PRT
<213> ORGANISM: Corynebacterium diphtheriae
<220> FEATURE:
<221> NAME/KEY: MISC_FEATURE
<223> OTHER INFORMATION: Translocation-deficient dtT (L350K)

<400> SEQUENCE: 5

Ser Cys Ile Asn Leu Asp Trp Asp Val Ile Arg Asp Lys Thr Lys Thr
1               5                   10                  15

Lys Ile Glu Ser Leu Lys Glu His Gly Pro Ile Lys Asn Lys Met Ser
            20                  25                  30

Glu Ser Pro Asn Lys Thr Val Ser Glu Glu Lys Ala Lys Gln Tyr Leu
        35                  40                  45

Glu Glu Phe His Gln Thr Ala Leu Glu His Pro Glu Leu Ser Glu Leu
    50                  55                  60

Lys Thr Val Thr Gly Thr Asn Pro Val Phe Ala Gly Ala Asn Tyr Ala
65                  70                  75                  80

Ala Trp Ala Val Asn Val Ala Gln Val Ile Asp Ser Glu Thr Ala Asp
            85                  90                  95

Asn Leu Glu Lys Thr Thr Ala Ala Leu Ser Ile Leu Pro Gly Ile Gly
            100                 105                 110

Ser Val Met Gly Ile Ala Asp Gly Ala Val His His Asn Thr Glu Glu
            115                 120                 125

Ile Val Ala Gln Ser Ile Ala Leu Ser Ser Leu Met Val Ala Gln Ala
            130                 135             140

Ile Pro Leu Val Gly Lys Val Asp Ile Gly Phe Ala Ala Tyr Asn
145                 150                 155                 160

Phe Val Glu Ser Ile Ile Asn Leu Phe Gln Val Val His Asn Ser Tyr
                165                 170                 175

Asn Arg Pro

<210> SEQ ID NO 6
<211> LENGTH: 160
<212> TYPE: PRT
<213> ORGANISM: Corynebacterium diphtheriae
<220> FEATURE:
<221> NAME/KEY: MISC_FEATURE
<223> OTHER INFORMATION: dtR (dtB Receptor-binding Domain)

<400> SEQUENCE: 6

Ala Tyr Ser Pro Gly His Lys Thr Gln Pro Phe Leu His Asp Gly Tyr
1               5                   10                  15

Ala Val Ser Trp Asn Thr Val Glu Asp Ser Ile Ile Arg Thr Gly Phe
            20                  25                  30

Gln Gly Glu Ser Gly His Asp Ile Lys Ile Thr Ala Glu Asn Thr Pro
        35                  40                  45

Leu Pro Ile Ala Gly Val Leu Leu Pro Thr Ile Pro Gly Lys Leu Asp
    50                  55                  60

Val Asn Lys Ser Lys Thr His Ile Ser Val Asn Gly Arg Lys Ile Arg
65                  70                  75                  80

Met Arg Cys Arg Ala Ile Asp Gly Asp Val Thr Phe Cys Arg Pro Lys
                85                  90                  95

Ser Pro Val Tyr Val Gly Asn Gly Val His Ala Asn Leu His Val Ala
            100                 105                 110

Phe His Arg Ser Ser Ser Glu Lys Ile His Ser Asn Glu Ile Ser Ser
        115                 120                 125

Asp Ser Ile Gly Val Leu Gly Tyr Gln Lys Thr Val Asp His Thr Lys
    130                 135                 140

Val Asn Ser Lys Leu Ser Leu Phe Phe Glu Ile Lys Ser Arg Gln Ala
145                 150                 155                 160

<210> SEQ ID NO 7
<211> LENGTH: 119
<212> TYPE: PRT
<213> ORGANISM: Artificial Sequence
<220> FEATURE:
<223> OTHER INFORMATION: Polyhistidine-SUMO

<400> SEQUENCE: 7

Met Gly Ser Ser His His His His His His Gly Ser Gly Leu Val Pro
1               5                   10                  15

Arg Gly Ser Ala Ser Met Ser Asp Ser Glu Val Asn Gln Glu Ala Lys
            20                  25                  30

Pro Glu Val Lys Pro Glu Val Lys Pro Glu Thr His Ile Asn Leu Lys
        35                  40                  45

Val Ser Asp Gly Ser Ser Glu Ile Phe Phe Lys Ile Lys Lys Thr Thr
    50                  55                  60

Pro Leu Arg Arg Leu Met Glu Ala Phe Ala Lys Arg Gln Gly Lys Glu
65                  70                  75                  80

Met Asp Ser Leu Arg Phe Leu Tyr Asp Gly Ile Arg Ile Gln Ala Asp
                85                  90                  95

Gln Thr Pro Glu Asp Leu Asp Met Glu Asp Asn Asp Ile Ile Glu Ala
            100                 105                 110

His Arg Glu Gln Ile Gly Gly
        115

<210> SEQ ID NO 8
<211> LENGTH: 10
<212> TYPE: PRT
<213> ORGANISM: Artificial Sequence
<220> FEATURE:
<223> OTHER INFORMATION: MYC tag

<400> SEQUENCE: 8

Glu Gln Lys Leu Ile Ser Glu Glu Asp Leu
1               5                   10

<210> SEQ ID NO 9
<211> LENGTH: 9
<212> TYPE: PRT
<213> ORGANISM: Artificial Sequence
<220> FEATURE:
<223> OTHER INFORMATION: SV40 nuclear localization sequences (NLS)

<400> SEQUENCE: 9

Ser Pro Pro Lys Lys Lys Arg Lys Val
1               5

<210> SEQ ID NO 10
<211> LENGTH: 5
<212> TYPE: PRT
<213> ORGANISM: Artificial Sequence
<220> FEATURE:
<223> OTHER INFORMATION: (G4S) linker

<400> SEQUENCE: 10

Gly Gly Gly Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: (G4S)2 linker

<400> SEQUENCE: 11

Gly Gly Gly Gly Ser Gly Gly Gly Gly Ser
1               5                   10

<210> SEQ ID NO 12
<211> LENGTH: 15
<212> TYPE: PRT
<213> ORGANISM: Artificial Sequence
<220> FEATURE:
<223> OTHER INFORMATION: (G4S)3 linker

<400> SEQUENCE: 12

Gly Gly Gly Gly Ser Gly Gly Gly Gly Ser Gly Gly Gly Gly Ser
1               5                   10                  15

<210> SEQ ID NO 13
<211> LENGTH: 238
<212> TYPE: PRT
<213> ORGANISM: Aequorea victoria
<220> FEATURE:
<221> NAME/KEY: MISC_FEATURE
<223> OTHER INFORMATION: Enhanced Green Fluorescent Protein (eGFP)

<400> SEQUENCE: 13

Gly Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Leu
    50                  55                  60

Thr Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg

```
                       85                  90                  95
Thr Ile Phe Phe Lys Asp Asp Gly Asn Tyr Lys Thr Arg Ala Glu Val
                  100                 105                 110

Lys Phe Glu Gly Asp Thr Leu Val Asn Arg Ile Glu Leu Lys Gly Ile
             115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr Leu Gly Met Asp Glu Leu Tyr Lys
225                 230                 235

<210> SEQ ID NO 14
<211> LENGTH: 235
<212> TYPE: PRT
<213> ORGANISM: Discosoma sp. (also: Actinodiscus or mushroom coral)
<220> FEATURE:
<221> NAME/KEY: MISC_FEATURE
<223> OTHER INFORMATION: Monomeric Cherry (mCherry)

<400> SEQUENCE: 14

Gly Ser Lys Gly Glu Glu Asp Asn Met Ala Ile Ile Lys Glu Phe Met
1               5                   10                  15

Arg Phe Lys Val His Met Glu Gly Ser Val Asn Gly His Glu Phe Glu
                20                  25                  30

Ile Glu Gly Glu Gly Glu Gly Arg Pro Tyr Glu Gly Thr Gln Thr Ala
            35                  40                  45

Lys Leu Lys Val Thr Lys Gly Gly Pro Leu Pro Phe Ala Trp Asp Ile
    50                  55                  60

Leu Ser Pro Gln Phe Met Tyr Gly Ser Lys Ala Tyr Val Lys His Pro
65                  70                  75                  80

Ala Asp Ile Pro Asp Tyr Leu Lys Leu Ser Phe Pro Glu Gly Phe Lys
                85                  90                  95

Trp Glu Arg Val Met Asn Phe Glu Asp Gly Gly Val Val Thr Val Thr
            100                 105                 110

Gln Asp Ser Ser Leu Gln Asp Gly Glu Phe Ile Tyr Lys Val Lys Leu
    115                 120                 125

Arg Gly Thr Asn Phe Pro Ser Asp Gly Pro Val Met Gln Lys Lys Thr
130                 135                 140

Met Gly Trp Glu Ala Ser Ser Glu Arg Met Tyr Pro Glu Asp Gly Ala
145                 150                 155                 160

Leu Lys Gly Glu Ile Lys Gln Arg Leu Lys Leu Lys Asp Gly Gly His
                165                 170                 175

Tyr Asp Ala Glu Val Lys Thr Thr Tyr Lys Ala Lys Lys Pro Val Gln
            180                 185                 190

Leu Pro Gly Ala Tyr Asn Val Asn Ile Lys Leu Asp Ile Thr Ser His
    195                 200                 205
```

```
Asn Glu Asp Tyr Thr Ile Val Glu Gln Tyr Glu Arg Ala Glu Gly Arg
    210                 215                 220
His Ser Thr Gly Gly Met Asp Glu Leu Tyr Lys
225                 230                 235

<210> SEQ ID NO 15
<211> LENGTH: 493
<212> TYPE: PRT
<213> ORGANISM: Bacillus megaterium
<220> FEATURE:
<221> NAME/KEY: MISC_FEATURE
<223> OTHER INFORMATION: alpha-amylase (B. megaterium)

<400> SEQUENCE: 15

Gly His Lys Gly Lys Ser Pro Thr Ala Asp Lys Asn Gly Val Phe Tyr
1                   5                   10                  15
Glu Val Tyr Val Asn Ser Phe Tyr Asp Ala Asn Lys Asp Gly His Gly
                20                  25                  30
Asp Leu Lys Gly Leu Thr Gln Lys Leu Asp Tyr Leu Asn Asp Gly Asn
            35                  40                  45
Ser His Thr Lys Asn Asp Leu Gln Val Asn Gly Ile Trp Met Met Pro
    50                  55                  60
Val Asn Pro Ser Pro Ser Tyr His Lys Tyr Asp Val Thr Asp Tyr Tyr
65                  70                  75                  80
Asn Ile Asp Pro Gln Tyr Gly Asn Leu Gln Asp Phe Arg Lys Leu Met
                85                  90                  95
Lys Glu Ala Asp Lys Arg Asp Val Lys Val Ile Met Asp Leu Val Val
            100                 105                 110
Asn His Thr Ser Ser Glu His Pro Trp Phe Gln Ala Ala Leu Lys Asp
    115                 120                 125
Lys Asn Ser Lys Tyr Arg Asp Tyr Tyr Ile Trp Ala Asp Lys Asn Thr
130                 135                 140
Asp Leu Asn Glu Lys Gly Ser Trp Gly Gln Gln Val Trp His Lys Ala
145                 150                 155                 160
Pro Asn Gly Glu Tyr Phe Tyr Gly Thr Phe Trp Glu Gly Met Pro Asp
                165                 170                 175
Leu Asn Tyr Asp Asn Pro Glu Val Arg Lys Glu Met Ile Asn Val Gly
            180                 185                 190
Lys Phe Trp Leu Asn Gln Gly Val Asp Gly Phe Arg Leu Asp Ala Ala
    195                 200                 205
Leu His Ile Phe Lys Gly Gln Thr Pro Glu Gly Ala Lys Lys Asn Ile
    210                 215                 220
Leu Trp Trp Asn Glu Phe Arg Asp Ala Met Lys Lys Glu Asn Pro Asn
225                 230                 235                 240
Val Tyr Leu Thr Gly Glu Val Trp Asp Gln Pro Glu Val Val Ala Pro
                245                 250                 255
Tyr Tyr Gln Ser Leu Asp Ser Leu Phe Asn Phe Asp Leu Ala Gly Lys
            260                 265                 270
Ile Val Ser Ser Val Lys Ala Gly Asn Asp Gln Gly Ile Ala Thr Ala
    275                 280                 285
Ala Ala Thr Asp Glu Leu Phe Lys Ser Tyr Asn Pro Asn Lys Ile
290                 295                 300
Asp Gly Ile Phe Leu Thr Asn His Asp Gln Asn Arg Val Met Ser Glu
305                 310                 315                 320
Leu Ser Gly Asp Val Asn Lys Ala Lys Ser Ala Ala Ser Ile Leu Leu
                325                 330                 335
```

Thr Leu Pro Gly Asn Pro Tyr Ile Tyr Tyr Gly Glu Ile Gly Met
                        340                 345                 350

Thr Gly Glu Lys Pro Asp Glu Leu Ile Arg Glu Pro Phe Arg Trp Tyr
                    355                 360                 365

Glu Gly Asn Gly Leu Gly Gln Thr Ser Trp Glu Thr Pro Ile Tyr Asn
                370                 375                 380

Lys Gly Asn Gly Val Ser Ile Glu Ala Gln Thr Lys Gln Lys Asp
385                 390                 395                 400

Ser Leu Leu Asn His Tyr Arg Glu Met Ile Arg Val Arg Gln Gln His
                    405                 410                 415

Glu Glu Leu Val Lys Gly Thr Leu Gln Ser Ile Ser Leu Asp Gln Lys
                420                 425                 430

Glu Val Val Ala Tyr Ser Arg Thr Tyr Lys Gly Lys Ser Ile Ser Val
                435                 440                 445

Tyr His Asn Ile Ser Asn Gln Pro Ile Lys Val Ser Ala Ala Lys
                450                 455                 460

Gly Lys Leu Ile Phe Ser Ser Glu Lys Gly Val Lys Val Lys Asn
465                 470                 475                 480

Gln Leu Val Ile Pro Ala Asn Thr Thr Ile Leu Ile Lys
                485                 490

<210> SEQ ID NO 16
<211> LENGTH: 497
<212> TYPE: PRT
<213> ORGANISM: Homo sapiens
<220> FEATURE:
<221> NAME/KEY: MISC_FEATURE
<223> OTHER INFORMATION: MeCP2 (e1 isoform)

<400> SEQUENCE: 16

Ala Ala Ala Ala Ala Ala Pro Ser Gly Gly Gly Gly Gly Gly Glu
1               5                   10                  15

Glu Glu Arg Leu Glu Glu Lys Ser Glu Asp Gln Asp Leu Gln Gly Leu
                20                  25                  30

Lys Asp Lys Pro Leu Lys Phe Lys Lys Val Lys Lys Asp Lys Lys Glu
                35                  40                  45

Glu Lys Glu Gly Lys His Glu Pro Val Gln Pro Ser Ala His His Ser
            50                  55                  60

Ala Glu Pro Ala Glu Ala Gly Lys Ala Glu Thr Ser Glu Gly Ser Gly
65                  70                  75                  80

Ser Ala Pro Ala Val Pro Glu Ala Ser Ala Ser Pro Lys Gln Arg Arg
                    85                  90                  95

Ser Ile Ile Arg Asp Arg Gly Pro Met Tyr Asp Asp Pro Thr Leu Pro
                100                 105                 110

Glu Gly Trp Thr Arg Lys Leu Lys Gln Arg Lys Ser Gly Arg Ser Ala
                115                 120                 125

Gly Lys Tyr Asp Val Tyr Leu Ile Asn Pro Gln Gly Lys Ala Phe Arg
            130                 135                 140

Ser Lys Val Glu Leu Ile Ala Tyr Phe Glu Lys Val Gly Asp Thr Ser
145                 150                 155                 160

Leu Asp Pro Asn Asp Phe Asp Phe Thr Val Thr Gly Arg Gly Ser Pro
                    165                 170                 175

Ser Arg Arg Glu Gln Lys Pro Pro Lys Lys Pro Lys Ser Pro Lys Ala
                180                 185                 190

Pro Gly Thr Gly Arg Gly Arg Gly Arg Pro Lys Gly Ser Gly Thr Thr

```
                195                 200                 205
Arg Pro Lys Ala Ala Thr Ser Glu Gly Val Gln Val Lys Arg Val Leu
210                 215                 220

Glu Lys Ser Pro Gly Lys Leu Leu Val Lys Met Pro Phe Gln Thr Ser
225                 230                 235                 240

Pro Gly Gly Lys Ala Glu Gly Gly Ala Thr Thr Ser Thr Gln Val
                245                 250                 255

Met Val Ile Lys Arg Pro Gly Arg Lys Arg Lys Ala Glu Ala Asp Pro
                260                 265                 270

Gln Ala Ile Pro Lys Lys Arg Gly Arg Lys Pro Gly Ser Val Val Ala
                275                 280                 285

Ala Ala Ala Glu Ala Lys Lys Ala Val Lys Glu Ser Ser Ile
                290                 295                 300

Arg Ser Val Gln Glu Thr Val Leu Pro Ile Lys Lys Arg Lys Thr Arg
305                 310                 315                 320

Glu Thr Val Ser Ile Glu Val Lys Glu Val Lys Pro Leu Leu Val
                325                 330                 335

Ser Thr Leu Gly Glu Lys Ser Gly Lys Gly Leu Lys Thr Cys Lys Ser
                340                 345                 350

Pro Gly Arg Lys Ser Lys Glu Ser Ser Pro Lys Gly Arg Ser Ser Ser
                355                 360                 365

Ala Ser Ser Pro Pro Lys Lys Glu His His His His His His Ser
370                 375                 380

Glu Ser Pro Lys Ala Pro Val Pro Leu Leu Pro Pro Leu Pro Pro Pro
385                 390                 395                 400

Pro Pro Glu Pro Glu Ser Ser Glu Asp Pro Thr Ser Pro Pro Glu Pro
                405                 410                 415

Gln Asp Leu Ser Ser Ser Val Cys Lys Glu Lys Met Pro Arg Gly
                420                 425                 430

Gly Ser Leu Glu Ser Asp Gly Cys Pro Lys Glu Pro Ala Lys Thr Gln
                435                 440                 445

Pro Ala Val Ala Thr Ala Ala Thr Ala Ala Glu Lys Tyr Lys His Arg
                450                 455                 460

Gly Glu Gly Glu Arg Lys Asp Ile Val Ser Ser Ser Met Pro Arg Pro
465                 470                 475                 480

Asn Arg Glu Glu Pro Val Asp Ser Arg Thr Pro Val Thr Glu Arg Val
                485                 490                 495

Ser

<210> SEQ ID NO 17
<211> LENGTH: 485
<212> TYPE: PRT
<213> ORGANISM: Homo sapiens
<220> FEATURE:
<221> NAME/KEY: MISC_FEATURE
<223> OTHER INFORMATION: MeCP2 (e2 isoform)

<400> SEQUENCE: 17

Val Ala Gly Met Leu Gly Leu Arg Glu Glu Lys Ser Glu Asp Gln Asp
1               5                   10                  15

Leu Gln Gly Leu Lys Asp Lys Pro Leu Lys Phe Lys Lys Val Lys Lys
                20                  25                  30

Asp Lys Lys Glu Glu Lys Glu Gly Lys His Glu Pro Val Gln Pro Ser
                35                  40                  45

Ala His His Ser Ala Glu Pro Ala Glu Ala Gly Lys Ala Glu Thr Ser
```

```
                50                  55                  60
Glu Gly Ser Gly Ser Ala Pro Ala Val Pro Glu Ala Ser Ala Ser Pro
 65                  70                  75                  80

Lys Gln Arg Arg Ser Ile Ile Arg Asp Arg Gly Pro Met Tyr Asp Asp
                 85                  90                  95

Pro Thr Leu Pro Glu Gly Trp Thr Arg Lys Leu Lys Gln Arg Lys Ser
                100                 105                 110

Gly Arg Ser Ala Gly Lys Tyr Asp Val Tyr Leu Ile Asn Pro Gln Gly
            115                 120                 125

Lys Ala Phe Arg Ser Lys Val Glu Leu Ile Ala Tyr Phe Glu Lys Val
        130                 135                 140

Gly Asp Thr Ser Leu Asp Pro Asn Asp Phe Asp Phe Thr Val Thr Gly
145                 150                 155                 160

Arg Gly Ser Pro Ser Arg Arg Glu Gln Lys Pro Pro Lys Lys Pro Lys
                165                 170                 175

Ser Pro Lys Ala Pro Gly Thr Gly Arg Gly Arg Gly Arg Pro Lys Gly
            180                 185                 190

Ser Gly Thr Thr Arg Pro Lys Ala Ala Thr Ser Glu Gly Val Gln Val
        195                 200                 205

Lys Arg Val Leu Glu Lys Ser Pro Gly Lys Leu Leu Val Lys Met Pro
210                 215                 220

Phe Gln Thr Ser Pro Gly Gly Lys Ala Glu Gly Gly Ala Thr Thr
225                 230                 235                 240

Ser Thr Gln Val Met Val Ile Lys Arg Pro Gly Arg Lys Arg Lys Ala
                245                 250                 255

Glu Ala Asp Pro Gln Ala Ile Pro Lys Lys Arg Gly Arg Lys Pro Gly
            260                 265                 270

Ser Val Val Ala Ala Ala Ala Glu Ala Lys Lys Ala Val Lys
        275                 280                 285

Glu Ser Ser Ile Arg Ser Val Gln Glu Thr Val Leu Pro Ile Lys Lys
        290                 295                 300

Arg Lys Thr Arg Glu Thr Val Ser Ile Glu Val Lys Glu Val Val Lys
305                 310                 315                 320

Pro Leu Leu Val Ser Thr Leu Gly Glu Lys Ser Gly Lys Gly Leu Lys
                325                 330                 335

Thr Cys Lys Ser Pro Gly Arg Lys Ser Lys Glu Ser Ser Pro Lys Gly
            340                 345                 350

Arg Ser Ser Ser Ala Ser Ser Pro Lys Lys Glu His His His His
        355                 360                 365

His His His Ser Glu Ser Pro Lys Ala Pro Val Pro Leu Leu Pro Pro
        370                 375                 380

Leu Pro Pro Pro Pro Glu Pro Glu Ser Ser Glu Asp Pro Thr Ser
385                 390                 395                 400

Pro Pro Glu Pro Gln Asp Leu Ser Ser Ser Val Cys Lys Glu Lys
                405                 410                 415

Met Pro Arg Gly Gly Ser Leu Glu Ser Asp Gly Cys Pro Lys Glu Pro
            420                 425                 430

Ala Lys Thr Gln Pro Ala Val Ala Thr Ala Ala Thr Ala Ala Glu Lys
        435                 440                 445

Tyr Lys His Arg Gly Glu Gly Glu Arg Lys Asp Ile Val Ser Ser Ser
        450                 455                 460

Met Pro Arg Pro Asn Arg Glu Glu Pro Val Asp Ser Arg Thr Pro Val
465                 470                 475                 480
```

Thr Glu Arg Val Ser
            485

<210> SEQ ID NO 18
<211> LENGTH: 585
<212> TYPE: PRT
<213> ORGANISM: Homo sapiens
<220> FEATURE:
<221> NAME/KEY: MISC_FEATURE
<223> OTHER INFORMATION: FMRP

<400> SEQUENCE: 18

```
Glu Glu Leu Val Val Glu Val Arg Gly Ser Asn Gly Ala Phe Tyr Lys
1               5                   10                  15

Ala Phe Val Lys Asp Val His Glu Asp Ser Ile Thr Val Ala Phe Glu
            20                  25                  30

Asn Asn Trp Gln Pro Asp Arg Gln Ile Pro Phe His Asp Val Arg Phe
        35                  40                  45

Pro Pro Pro Val Gly Tyr Asn Lys Asp Ile Asn Glu Ser Asp Glu Val
    50                  55                  60

Glu Val Tyr Ser Arg Ala Asn Glu Lys Glu Pro Cys Cys Trp Trp Leu
65                  70                  75                  80

Ala Lys Val Arg Met Ile Lys Gly Glu Phe Tyr Val Ile Glu Tyr Ala
                85                  90                  95

Ala Cys Asp Ala Thr Tyr Asn Glu Ile Val Thr Ile Glu Arg Leu Arg
            100                 105                 110

Ser Val Asn Pro Asn Lys Pro Ala Thr Lys Asp Thr Phe His Lys Ile
        115                 120                 125

Lys Leu Asp Val Pro Glu Asp Leu Arg Gln Met Cys Ala Lys Glu Ala
    130                 135                 140

Ala His Lys Asp Phe Lys Lys Ala Val Gly Ala Phe Ser Val Thr Tyr
145                 150                 155                 160

Asp Pro Glu Asn Tyr Gln Leu Val Ile Leu Ser Ile Asn Glu Val Thr
                165                 170                 175

Ser Lys Arg Ala His Met Leu Ile Asp Met His Phe Arg Ser Leu Arg
            180                 185                 190

Thr Lys Leu Ser Leu Ile Met Arg Asn Glu Glu Ala Ser Lys Gln Leu
        195                 200                 205

Glu Ser Ser Arg Gln Leu Ala Ser Arg Phe His Glu Gln Phe Ile Val
    210                 215                 220

Arg Glu Asp Leu Met Gly Leu Ala Ile Gly Thr His Gly Ala Asn Ile
225                 230                 235                 240

Gln Gln Ala Arg Lys Val Pro Gly Val Thr Ala Ile Asp Leu Asp Glu
                245                 250                 255

Asp Thr Cys Thr Phe His Ile Tyr Gly Glu Asp Gln Asp Ala Val Lys
            260                 265                 270

Lys Ala Arg Ser Phe Leu Glu Phe Ala Glu Asp Val Ile Gln Val Pro
        275                 280                 285

Arg Asn Leu Val Gly Lys Val Ile Gly Lys Asn Gly Lys Leu Ile Gln
    290                 295                 300

Glu Ile Val Asp Lys Ser Gly Val Val Arg Val Arg Ile Glu Ala Glu
305                 310                 315                 320

Asn Glu Lys Asn Val Pro Gln Glu Glu Glu Ile Met Pro Pro Asn Ser
                325                 330                 335

Leu Pro Ser Asn Asn Ser Arg Val Gly Pro Asn Ala Pro Glu Glu Lys
```

```
                 340                 345                 350
Lys His Leu Asp Ile Lys Glu Asn Ser Thr His Phe Ser Gln Pro Asn
            355                 360                 365

Ser Thr Lys Val Gln Arg Gly Met Val Pro Phe Val Phe Val Gly Thr
        370                 375                 380

Lys Asp Ser Ile Ala Asn Ala Thr Val Leu Leu Asp Tyr His Leu Asn
385                 390                 395                 400

Tyr Leu Lys Glu Val Asp Gln Leu Arg Leu Glu Arg Leu Gln Ile Asp
                405                 410                 415

Glu Gln Leu Arg Gln Ile Gly Ala Ser Ser Arg Pro Pro Asn Arg
            420                 425                 430

Thr Asp Lys Glu Lys Ser Tyr Val Thr Asp Gly Gln Gly Met Gly
        435                 440                 445

Arg Gly Ser Arg Pro Tyr Arg Asn Arg Gly His Gly Arg Arg Gly Pro
450                 455                 460

Gly Tyr Thr Ser Ala Pro Thr Glu Glu Arg Glu Ser Phe Leu Arg
465                 470                 475                 480

Arg Gly Asp Gly Arg Arg Gly Gly Gly Arg Gly Gln Gly Gly
                485                 490                 495

Arg Gly Arg Gly Gly Phe Lys Gly Asn Asp Asp His Ser Arg Thr
            500                 505                 510

Asp Asn Arg Pro Arg Asn Pro Arg Glu Ala Lys Gly Arg Thr Thr Asp
            515                 520                 525

Gly Ser Leu Gln Ile Arg Val Asp Cys Asn Asn Glu Arg Ser Val His
        530                 535                 540

Thr Lys Thr Leu Gln Asn Thr Ser Ser Glu Gly Ser Arg Leu Arg Thr
545                 550                 555                 560

Gly Lys Asp Arg Asn Gln Lys Lys Glu Lys Pro Asp Ser Val Asp Gly
                565                 570                 575

Gln Gln Pro Leu Val Asn Gly Val Pro
            580                 585

<210> SEQ ID NO 19
<211> LENGTH: 294
<212> TYPE: PRT
<213> ORGANISM: Homo sapiens
<220> FEATURE:
<221> NAME/KEY: MISC_FEATURE
<223> OTHER INFORMATION: SMN protein

<400> SEQUENCE: 19

Met Ala Met Ser Ser Gly Gly Ser Gly Gly Gly Val Pro Glu Gln Glu
1               5                   10                  15

Asp Ser Val Leu Phe Arg Arg Gly Thr Gly Gln Ser Asp Asp Ser Asp
                20                  25                  30

Ile Trp Asp Asp Thr Ala Leu Ile Lys Ala Tyr Asp Lys Ala Val Ala
            35                  40                  45

Ser Phe Lys His Ala Leu Lys Asn Gly Asp Ile Cys Glu Thr Ser Gly
        50                  55                  60

Lys Pro Lys Thr Thr Pro Lys Arg Lys Pro Ala Lys Lys Asn Lys Ser
65                  70                  75                  80

Gln Lys Lys Asn Thr Ala Ala Ser Leu Gln Gln Trp Lys Val Gly Asp
                85                  90                  95

Lys Cys Ser Ala Ile Trp Ser Glu Asp Gly Cys Ile Tyr Pro Ala Thr
            100                 105                 110
```

```
Ile Ala Ser Ile Asp Phe Lys Arg Glu Thr Cys Val Val Tyr Thr
            115                 120                 125

Gly Tyr Gly Asn Arg Glu Glu Gln Asn Leu Ser Asp Leu Leu Ser Pro
130                 135                 140

Ile Cys Glu Val Ala Asn Asn Ile Glu Gln Asn Ala Gln Glu Asn Glu
145                 150                 155                 160

Asn Glu Ser Gln Val Ser Thr Asp Glu Ser Glu Asn Ser Arg Ser Pro
                165                 170                 175

Gly Asn Lys Ser Asp Asn Ile Lys Pro Lys Ser Ala Pro Trp Asn Ser
            180                 185                 190

Phe Leu Pro Pro Pro Pro Met Pro Gly Pro Arg Leu Gly Pro Gly
            195                 200                 205

Lys Pro Gly Leu Lys Phe Asn Gly Pro Pro Pro Pro Pro Pro Pro
    210                 215                 220

Pro Pro His Leu Leu Ser Cys Trp Leu Pro Pro Phe Pro Ser Gly Pro
225                 230                 235                 240

Pro Ile Ile Pro Pro Pro Pro Ile Cys Pro Asp Ser Leu Asp Asp
                245                 250                 255

Ala Asp Ala Leu Gly Ser Met Leu Ile Ser Trp Tyr Met Ser Gly Tyr
            260                 265                 270

His Thr Gly Tyr Tyr Met Gly Phe Arg Gln Asn Gln Lys Glu Gly Arg
        275                 280                 285

Cys Ser His Ser Leu Asn
    290

<210> SEQ ID NO 20
<211> LENGTH: 261
<212> TYPE: PRT
<213> ORGANISM: Clostridium difficile
<220> FEATURE:
<221> NAME/KEY: MISC_FEATURE
<223> OTHER INFORMATION: CPD (C. difficile)

<400> SEQUENCE: 20

Glu Gly Ser Leu Gly Glu Asp Asp Asn Leu Asp Phe Ser Gln Asn Ile
1               5                   10                  15

Val Val Asp Lys Glu Tyr Leu Leu Glu Lys Ile Ser Ser Leu Ala Arg
            20                  25                  30

Ser Ser Glu Arg Gly Tyr Ile His Tyr Ile Val Gln Leu Gln Gly Asp
        35                  40                  45

Lys Ile Ser Tyr Glu Ala Ala Cys Asn Leu Phe Ala Lys Thr Pro Tyr
    50                  55                  60

Asp Ser Val Leu Phe Gln Lys Asn Ile Glu Asp Ser Glu Ile Ala Tyr
65                  70                  75                  80

Tyr Tyr Asn Pro Gly Asp Gly Glu Ile Gln Glu Ile Asp Lys Tyr Lys
                85                  90                  95

Ile Pro Ser Ile Ile Ser Asp Arg Pro Lys Ile Lys Leu Thr Phe Ile
            100                 105                 110

Gly His Gly Lys Asp Glu Phe Asn Thr Asp Ile Phe Ala Gly Phe Asp
        115                 120                 125

Val Asp Ser Leu Ser Thr Glu Ile Glu Ala Ala Ile Asp Leu Ala Lys
    130                 135                 140

Glu Asp Ile Ser Pro Lys Ser Ile Glu Ile Asn Leu Leu Gly Cys Asn
145                 150                 155                 160

Met Phe Ser Tyr Ser Ile Asn Val Glu Glu Thr Tyr Pro Gly Lys Leu
                165                 170                 175
```

-continued

```
Leu Leu Lys Val Lys Asp Lys Ile Ser Glu Leu Met Pro Ser Ile Ser
            180                 185                 190

Gln Asp Ser Ile Ile Val Ser Ala Asn Gln Tyr Glu Val Arg Ile Asn
            195                 200                 205

Ser Glu Gly Arg Arg Glu Leu Leu Asp His Ser Gly Glu Trp Ile Asn
210                 215                 220

Lys Glu Glu Ser Ile Ile Lys Asp Ile Ser Ser Lys Glu Tyr Ile Ser
225                 230                 235                 240

Phe Asn Pro Lys Glu Asn Lys Ile Thr Val Lys Ser Lys Asn Leu Pro
            245                 250                 255

Glu Leu Ser Thr Leu
            260

<210> SEQ ID NO 21
<211> LENGTH: 212
<212> TYPE: PRT
<213> ORGANISM: Vibrio cholerae
<220> FEATURE:
<221> NAME/KEY: MISC_FEATURE
<223> OTHER INFORMATION: CPD (V. cholera)

<400> SEQUENCE: 21

Lys Glu Ala Leu Ala Asp Gly Lys Ile Leu His Asn Gln Asn Val Asn
1               5                   10                  15

Ser Trp Gly Pro Ile Thr Val Thr Pro Thr Asp Gly Glu Thr
            20                  25                  30

Arg Phe Asp Gly Gln Ile Ile Val Gln Met Glu Asn Asp Pro Val Val
            35                  40                  45

Ala Lys Ala Ala Ala Asn Leu Ala Gly Lys His Ala Glu Ser Ser Val
    50                  55                  60

Val Val Gln Leu Asp Ser Asp Gly Asn Tyr Arg Val Val Tyr Gly Asp
65                  70                  75                  80

Pro Ser Lys Leu Asp Gly Lys Leu Arg Trp Gln Leu Val Gly His Gly
            85                  90                  95

Arg Asp His Ser Glu Thr Asn Asn Thr Arg Leu Ser Gly Tyr Ser Ala
            100                 105                 110

Asp Glu Leu Ala Val Lys Leu Ala Lys Phe Gln Gln Ser Phe Asn Gln
        115                 120                 125

Ala Glu Asn Ile Asn Asn Lys Pro Asp His Ile Ser Ile Val Gly Cys
    130                 135                 140

Ser Leu Val Ser Asp Asp Lys Gln Lys Gly Phe Gly His Gln Phe Ile
145                 150                 155                 160

Asn Ala Met Asp Ala Asn Gly Leu Arg Val Asp Val Ser Val Arg Ser
            165                 170                 175

Ser Glu Leu Ala Val Asp Glu Ala Gly Arg Lys His Thr Lys Asp Ala
            180                 185                 190

Asn Gly Asp Trp Val Gln Lys Ala Glu Asn Asn Lys Val Ser Leu Ser
            195                 200                 205

Trp Asp Ala Gln
    210

<210> SEQ ID NO 22
<211> LENGTH: 1371
<212> TYPE: PRT
<213> ORGANISM: Streptococcus pyogenes
<220> FEATURE:
<221> NAME/KEY: MISC_FEATURE
```

<223> OTHER INFORMATION: Cas9 (S. pyogenes)

<400> SEQUENCE: 22

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Gly Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Ala Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Ile Tyr
            180                 185                 190

Asn Gln Leu Phe Glu Glu Asn Pro Ile Asn Ala Ser Arg Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Arg Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Ser Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400
```

-continued

Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Ala Tyr His Asp Leu Leu Lys Ile Ile Lys Asp Lys Asp Phe Leu Asp
        595                 600                 605
Asn Glu Glu Asn Glu Asp Ile Leu Glu Asp Ile Val Leu Thr Leu Thr
    610                 615                 620
Leu Phe Glu Asp Arg Gly Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
        675                 680                 685
Ala Asn Arg Asn Phe Met Gln Leu Ile His Asp Asp Ser Leu Thr Phe
    690                 695                 700
Lys Glu Asp Ile Gln Lys Ala Gln Val Ser Gly Gln Gly His Ser Leu
705                 710                 715                 720
His Glu Gln Ile Ala Asn Leu Ala Gly Ser Pro Ala Ile Lys Lys Gly
                725                 730                 735
Ile Leu Gln Thr Val Lys Ile Val Asp Glu Leu Val Lys Val Met Gly
            740                 745                 750
His Lys Pro Glu Asn Ile Val Ile Glu Met Ala Arg Glu Asn Gln Thr
        755                 760                 765
Thr Gln Lys Gly Gln Lys Asn Ser Arg Glu Arg Met Lys Arg Ile Glu
    770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
Asn Gly Arg Asp Met Tyr Val Asp Gln Glu Leu Asp Ile Asn Arg Leu

-continued

Ser Asp Tyr Asp Val Asp His Ile Val Pro Gln Ser Phe Ile Lys Asp
        820                 825                 830
                835                 840                 845

Asp Ser Ile Asp Asn Lys Val Leu Thr Arg Ser Asp Lys Asn Arg Gly
        850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
                915                 920                 925

His Val Ala Gln Ile Leu Asp Ser Arg Met Asn Thr Lys Tyr Asp Glu
                930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
                995                 1000                1005

Tyr Gly Asp Tyr Lys Val Tyr Asp Val Arg Lys Met Ile Ala Lys
        1010                1015                1020

Ser Glu Gln Glu Ile Gly Lys Ala Thr Ala Lys Tyr Phe Phe Tyr
        1025                1030                1035

Ser Asn Ile Met Asn Phe Phe Lys Thr Glu Ile Thr Leu Ala Asn
        1040                1045                1050

Gly Glu Ile Arg Lys Arg Pro Leu Ile Glu Thr Asn Gly Glu Thr
        1055                1060                1065

Gly Glu Ile Val Trp Asp Lys Gly Arg Asp Phe Ala Thr Val Arg
        1070                1075                1080

Lys Val Leu Ser Met Pro Gln Val Asn Ile Val Lys Lys Thr Glu
        1085                1090                1095

Val Gln Thr Gly Gly Phe Ser Lys Glu Ser Ile Leu Pro Lys Arg
        1100                1105                1110

Asn Ser Asp Lys Leu Ile Ala Arg Lys Lys Asp Trp Asp Pro Lys
        1115                1120                1125

Lys Tyr Gly Gly Phe Asp Ser Pro Thr Val Ala Tyr Ser Val Leu
        1130                1135                1140

Val Val Ala Lys Val Glu Lys Gly Lys Ser Lys Lys Leu Lys Ser
        1145                1150                1155

Val Lys Glu Leu Leu Gly Ile Thr Ile Met Glu Arg Ser Ser Phe
        1160                1165                1170

Glu Lys Asn Pro Ile Asp Phe Leu Glu Ala Lys Gly Tyr Lys Glu
        1175                1180                1185

Val Lys Lys Asp Leu Ile Ile Lys Leu Pro Lys Tyr Ser Leu Phe
        1190                1195                1200

Glu Leu Glu Asn Gly Arg Lys Arg Met Leu Ala Ser Ala Gly Glu
        1205                1210                1215

Leu Gln Lys Gly Asn Glu Leu Ala Leu Pro Ser Lys Tyr Val Asn
        1220                1225                1230

```
Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp Ser
    1355                1360                1365

Pro Val Arg
    1370

<210> SEQ ID NO 23
<211> LENGTH: 1403
<212> TYPE: PRT
<213> ORGANISM: Artificial Sequence
<220> FEATURE:
<223> OTHER INFORMATION: Cas9 (S. pyogenes) with N-terminal His, SV40
      and C-terminal SV40 sequences

<400> SEQUENCE: 23

His His His His His His Gly Ser Gly Ala Thr Met Ala Ser Pro Pro
1               5                   10                  15

Lys Lys Lys Arg Lys Val Gly Ser Met Asp Lys Lys Tyr Ser Ile Gly
                20                  25                  30

Leu Asp Ile Gly Thr Asn Ser Val Gly Trp Ala Val Ile Thr Asp Asp
            35                  40                  45

Tyr Lys Val Pro Ser Lys Lys Phe Lys Val Leu Gly Asn Thr Asp Arg
    50                  55                  60

His Ser Ile Lys Lys Asn Leu Ile Gly Ala Leu Leu Phe Gly Ser Gly
65                  70                  75                  80

Glu Thr Ala Glu Ala Thr Arg Leu Lys Arg Thr Ala Arg Arg Arg Tyr
                85                  90                  95

Thr Arg Arg Lys Asn Arg Ile Cys Tyr Leu Gln Glu Ile Phe Ser Asn
            100                 105                 110

Glu Met Ala Lys Val Asp Asp Ser Phe Phe His Arg Leu Glu Glu Ser
        115                 120                 125

Phe Leu Val Glu Glu Asp Lys Lys His Glu Arg His Pro Ile Phe Gly
    130                 135                 140

Asn Ile Val Asp Glu Val Ala Tyr His Glu Lys Tyr Pro Thr Ile Tyr
145                 150                 155                 160

His Leu Arg Lys Lys Leu Ala Asp Ser Thr Asp Lys Ala Asp Leu Arg
                165                 170                 175

Leu Ile Tyr Leu Ala Leu Ala His Met Ile Lys Phe Arg Gly His Phe
            180                 185                 190

Leu Ile Glu Gly Asp Leu Asn Pro Asp Asn Ser Asp Val Asp Lys Leu
```

```
            195                 200                 205
    Phe Ile Gln Leu Val Gln Ile Tyr Asn Gln Leu Phe Glu Glu Asn Pro
    210                 215                 220
    Ile Asn Ala Ser Arg Val Asp Ala Lys Ala Ile Leu Ser Ala Arg Leu
225                 230                 235                 240
    Ser Lys Ser Arg Arg Leu Glu Asn Leu Ile Ala Gln Leu Pro Gly Glu
                        245                 250                 255
    Lys Arg Asn Gly Leu Phe Gly Asn Leu Ile Ala Leu Ser Leu Gly Leu
                        260                 265                 270
    Thr Pro Asn Phe Lys Ser Asn Phe Asp Leu Ala Glu Asp Ala Lys Leu
                        275                 280                 285
    Gln Leu Ser Lys Asp Thr Tyr Asp Asp Leu Asp Asn Leu Leu Ala
    290                 295                 300
    Gln Ile Gly Asp Gln Tyr Ala Asp Leu Phe Leu Ala Ala Lys Asn Leu
    305                 310                 315                 320
    Ser Asp Ala Ile Leu Leu Ser Asp Ile Leu Arg Val Asn Ser Glu Ile
                        325                 330                 335
    Thr Lys Ala Pro Leu Ser Ala Ser Met Ile Lys Arg Tyr Asp Glu His
                        340                 345                 350
    His Gln Asp Leu Thr Leu Leu Lys Ala Leu Val Arg Gln Gln Leu Pro
                        355                 360                 365
    Glu Lys Tyr Lys Glu Ile Phe Phe Asp Gln Ser Lys Asn Gly Tyr Ala
    370                 375                 380
    Gly Tyr Ile Asp Gly Gly Ala Ser Gln Glu Glu Phe Tyr Lys Phe Ile
385                 390                 395                 400
    Lys Pro Ile Leu Glu Lys Met Asp Gly Thr Glu Glu Leu Leu Val Lys
                        405                 410                 415
    Leu Asn Arg Glu Asp Leu Leu Arg Lys Gln Arg Thr Phe Asp Asn Gly
                        420                 425                 430
    Ser Ile Pro His Gln Ile His Leu Gly Glu Leu His Ala Ile Leu Arg
                        435                 440                 445
    Arg Gln Glu Asp Phe Tyr Pro Phe Leu Lys Asp Asn Arg Glu Lys Ile
    450                 455                 460
    Glu Lys Ile Leu Thr Phe Arg Ile Pro Tyr Tyr Val Gly Pro Leu Ala
465                 470                 475                 480
    Arg Gly Asn Ser Arg Phe Ala Trp Met Thr Arg Lys Ser Glu Glu Thr
                        485                 490                 495
    Ile Thr Pro Trp Asn Phe Glu Glu Val Val Asp Lys Gly Ala Ser Ala
                        500                 505                 510
    Gln Ser Phe Ile Glu Arg Met Thr Asn Phe Asp Lys Asn Leu Pro Asn
                        515                 520                 525
    Glu Lys Val Leu Pro Lys His Ser Leu Leu Tyr Glu Tyr Phe Thr Val
                        530                 535                 540
    Tyr Asn Glu Leu Thr Lys Val Lys Tyr Val Thr Glu Gly Met Arg Lys
545                 550                 555                 560
    Pro Ala Phe Leu Ser Gly Glu Gln Lys Lys Ala Ile Val Asp Leu Leu
                        565                 570                 575
    Phe Lys Thr Asn Arg Lys Val Thr Val Lys Gln Leu Lys Glu Asp Tyr
                        580                 585                 590
    Phe Lys Lys Ile Glu Cys Phe Asp Ser Val Glu Ile Ser Gly Val Glu
                        595                 600                 605
    Asp Arg Phe Asn Ala Ser Leu Gly Ala Tyr His Asp Leu Leu Lys Ile
    610                 615                 620
```

```
Ile Lys Asp Lys Asp Phe Leu Asp Asn Glu Glu Asn Glu Asp Ile Leu
625                 630                 635                 640

Glu Asp Ile Val Leu Thr Leu Thr Leu Phe Glu Asp Arg Gly Met Ile
            645                 650                 655

Glu Glu Arg Leu Lys Thr Tyr Ala His Leu Phe Asp Asp Lys Val Met
        660                 665                 670

Lys Gln Leu Lys Arg Arg Tyr Thr Gly Trp Gly Arg Leu Ser Arg
    675                 680                 685

Lys Leu Ile Asn Gly Ile Arg Asp Lys Gln Ser Gly Lys Thr Ile Leu
690                 695                 700

Asp Phe Leu Lys Ser Asp Gly Phe Ala Asn Arg Asn Phe Met Gln Leu
705                 710                 715                 720

Ile His Asp Asp Ser Leu Thr Phe Lys Glu Asp Ile Gln Lys Ala Gln
                725                 730                 735

Val Ser Gly Gln Gly His Ser Leu His Glu Gln Ile Ala Asn Leu Ala
            740                 745                 750

Gly Ser Pro Ala Ile Lys Lys Gly Ile Leu Gln Thr Val Lys Ile Val
        755                 760                 765

Asp Glu Leu Val Lys Val Met Gly His Lys Pro Glu Asn Ile Val Ile
    770                 775                 780

Glu Met Ala Arg Glu Asn Gln Thr Thr Gln Lys Gly Gln Lys Asn Ser
785                 790                 795                 800

Arg Glu Arg Met Lys Arg Ile Glu Glu Gly Ile Lys Glu Leu Gly Ser
                805                 810                 815

Gln Ile Leu Lys Glu His Pro Val Glu Asn Thr Gln Leu Gln Asn Glu
            820                 825                 830

Lys Leu Tyr Leu Tyr Tyr Leu Gln Asn Gly Arg Asp Met Tyr Val Asp
        835                 840                 845

Gln Glu Leu Asp Ile Asn Arg Leu Ser Asp Tyr Asp Val Asp His Ile
    850                 855                 860

Val Pro Gln Ser Phe Ile Lys Asp Asp Ser Ile Asp Asn Lys Val Leu
865                 870                 875                 880

Thr Arg Ser Asp Lys Asn Arg Gly Lys Ser Asp Asn Val Pro Ser Glu
                885                 890                 895

Glu Val Val Lys Lys Met Lys Asn Tyr Trp Arg Gln Leu Leu Asn Ala
            900                 905                 910

Lys Leu Ile Thr Gln Arg Lys Phe Asp Asn Leu Thr Lys Ala Glu Arg
        915                 920                 925

Gly Gly Leu Ser Glu Leu Asp Lys Ala Gly Phe Ile Lys Arg Gln Leu
    930                 935                 940

Val Glu Thr Arg Gln Ile Thr Lys His Val Ala Gln Ile Leu Asp Ser
945                 950                 955                 960

Arg Met Asn Thr Lys Tyr Asp Glu Asn Asp Lys Leu Ile Arg Glu Val
                965                 970                 975

Lys Val Ile Thr Leu Lys Ser Lys Leu Val Ser Asp Phe Arg Lys Asp
            980                 985                 990

Phe Gln Phe Tyr Lys Val Arg Glu Ile Asn Asn Tyr His His Ala His
        995                 1000                1005

Asp Ala Tyr Leu Asn Ala Val Val Gly Thr Ala Leu Ile Lys Lys
        1010                1015                1020

Tyr Pro Lys Leu Glu Ser Glu Phe Val Tyr Gly Asp Tyr Lys Val
        1025                1030                1035
```

```
Tyr Asp Val Arg Lys Met Ile Ala Lys Ser Glu Gln Glu Ile Gly
    1040            1045                1050

Lys Ala Thr Ala Lys Tyr Phe Phe Tyr Ser Asn Ile Met Asn Phe
    1055            1060                1065

Phe Lys Thr Glu Ile Thr Leu Ala Asn Gly Glu Ile Arg Lys Arg
    1070            1075                1080

Pro Leu Ile Glu Thr Asn Gly Glu Thr Gly Glu Ile Val Trp Asp
    1085            1090                1095

Lys Gly Arg Asp Phe Ala Thr Val Arg Lys Val Leu Ser Met Pro
    1100            1105                1110

Gln Val Asn Ile Val Lys Lys Thr Glu Val Gln Thr Gly Gly Phe
    1115            1120                1125

Ser Lys Glu Ser Ile Leu Pro Lys Arg Asn Ser Asp Lys Leu Ile
    1130            1135                1140

Ala Arg Lys Lys Asp Trp Asp Pro Lys Lys Tyr Gly Gly Phe Asp
    1145            1150                1155

Ser Pro Thr Val Ala Tyr Ser Val Leu Val Val Ala Lys Val Glu
    1160            1165                1170

Lys Gly Lys Ser Lys Lys Leu Lys Ser Val Lys Glu Leu Leu Gly
    1175            1180                1185

Ile Thr Ile Met Glu Arg Ser Ser Phe Glu Lys Asn Pro Ile Asp
    1190            1195                1200

Phe Leu Glu Ala Lys Gly Tyr Lys Glu Val Lys Lys Asp Leu Ile
    1205            1210                1215

Ile Lys Leu Pro Lys Tyr Ser Leu Phe Glu Leu Glu Asn Gly Arg
    1220            1225                1230

Lys Arg Met Leu Ala Ser Ala Gly Glu Leu Gln Lys Gly Asn Glu
    1235            1240                1245

Leu Ala Leu Pro Ser Lys Tyr Val Asn Phe Leu Tyr Leu Ala Ser
    1250            1255                1260

His Tyr Glu Lys Leu Lys Gly Ser Pro Glu Asp Asn Glu Gln Lys
    1265            1270                1275

Gln Leu Phe Val Glu Gln His Lys His Tyr Leu Asp Glu Ile Ile
    1280            1285                1290

Glu Gln Ile Ser Glu Phe Ser Lys Arg Val Ile Leu Ala Asp Ala
    1295            1300                1305

Asn Leu Asp Lys Val Leu Ser Ala Tyr Asn Lys His Arg Asp Lys
    1310            1315                1320

Pro Ile Arg Glu Gln Ala Glu Asn Ile Ile His Leu Phe Thr Leu
    1325            1330                1335

Thr Asn Leu Gly Ala Pro Ala Ala Phe Lys Tyr Phe Asp Thr Thr
    1340            1345                1350

Ile Asp Arg Lys Arg Tyr Thr Ser Thr Lys Glu Val Leu Asp Ala
    1355            1360                1365

Thr Leu Ile His Gln Ser Ile Thr Gly Leu Tyr Glu Thr Arg Ile
    1370            1375                1380

Asp Leu Ser Gln Leu Gly Gly Asp Ser Pro Val Arg Ser Pro Lys
    1385            1390                1395

Lys Lys Arg Lys Val
    1400

<210> SEQ ID NO 24
<211> LENGTH: 289
<212> TYPE: PRT
```

<213> ORGANISM: Homo sapiens
<220> FEATURE:
<221> NAME/KEY: MISC_FEATURE
<223> OTHER INFORMATION: PNP

<400> SEQUENCE: 24

```
Met Glu Asn Gly Tyr Thr Tyr Glu Asp Tyr Lys Asn Thr Ala Glu Trp
1               5                   10                  15

Leu Leu Ser His Thr Lys His Arg Pro Gln Val Ala Ile Ile Cys Gly
            20                  25                  30

Ser Gly Leu Gly Gly Leu Thr Asp Lys Leu Thr Gln Ala Gln Ile Phe
        35                  40                  45

Asp Tyr Ser Glu Ile Pro Asn Phe Pro Arg Ser Thr Val Pro Gly His
    50                  55                  60

Ala Gly Arg Leu Val Phe Gly Phe Leu Asn Gly Arg Ala Cys Val Met
65                  70                  75                  80

Met Gln Gly Arg Phe His Met Tyr Glu Gly Tyr Pro Leu Trp Lys Val
                85                  90                  95

Thr Phe Pro Val Arg Val Phe His Leu Leu Gly Val Asp Thr Leu Val
            100                 105                 110

Val Thr Asn Ala Ala Gly Gly Leu Asn Pro Lys Phe Glu Val Gly Asp
        115                 120                 125

Ile Met Leu Ile Arg Asp His Ile Asn Leu Pro Gly Phe Ser Gly Gln
    130                 135                 140

Asn Pro Leu Arg Gly Pro Asn Asp Glu Arg Phe Gly Asp Arg Phe Pro
145                 150                 155                 160

Ala Met Ser Asp Ala Tyr Asp Arg Thr Met Arg Gln Arg Ala Leu Ser
                165                 170                 175

Thr Trp Lys Gln Met Gly Glu Gln Arg Glu Leu Gln Glu Gly Thr Tyr
            180                 185                 190

Val Met Val Ala Gly Pro Ser Phe Glu Thr Val Ala Glu Cys Arg Val
        195                 200                 205

Leu Gln Lys Leu Gly Ala Asp Ala Val Gly Met Ser Thr Val Pro Glu
    210                 215                 220

Val Ile Val Ala Arg His Cys Gly Leu Arg Val Phe Gly Phe Ser Leu
225                 230                 235                 240

Ile Thr Asn Lys Val Ile Met Asp Tyr Glu Ser Leu Glu Lys Ala Asn
                245                 250                 255

His Glu Glu Val Leu Ala Ala Gly Lys Gln Ala Ala Gln Lys Leu Glu
            260                 265                 270

Gln Phe Val Ser Ile Leu Met Ala Ser Ile Pro Leu Pro Asp Lys Ala
        275                 280                 285

Ser
```

<210> SEQ ID NO 25
<211> LENGTH: 98
<212> TYPE: PRT
<213> ORGANISM: Artificial Sequence
<220> FEATURE:
<223> OTHER INFORMATION: SUMO

<400> SEQUENCE: 25

```
Met Ser Asp Ser Glu Val Asn Gln Glu Ala Lys Pro Glu Val Lys Pro
1               5                   10                  15

Glu Val Lys Pro Glu Thr His Ile Asn Leu Lys Val Ser Asp Gly Ser
            20                  25                  30
```

```
Ser Glu Ile Phe Phe Lys Ile Lys Lys Thr Thr Pro Leu Arg Arg Leu
         35                  40                  45

Met Glu Ala Phe Ala Lys Arg Gln Gly Lys Glu Met Asp Ser Leu Arg
 50                  55                  60

Phe Leu Tyr Asp Gly Ile Arg Ile Gln Ala Asp Gln Thr Pro Glu Asp
 65                  70                  75                  80

Leu Asp Met Glu Asp Asn Asp Ile Ile Glu Ala His Arg Glu Gln Ile
                 85                  90                  95

Gly Gly

<210> SEQ ID NO 26
<211> LENGTH: 1530
<212> TYPE: DNA
<213> ORGANISM: Homo sapiens
<220> FEATURE:
<221> NAME/KEY: misc_feature
<223> OTHER INFORMATION: RRSP

<400> SEQUENCE: 26
ggtgataaaa ccaaggtcgt ggtcgattta gcgcaaatct ttacggtgca agagctgaaa      60
gaaagagcaa agttttttgc taaaccgatt ggcgcatcct accaaggtat tctcgatcaa     120
ctcgaccttg tgcatcaggc taaaggccgc gatcaaatcg cagcgagctt tgagcttaat     180
aagaagatta tgactacat cgctgaacat ccaacttcgg ggcgtaatca agcgctaacg     240
cagttgaaag agcaggtcac cagtgcgttg tttatcggta agatgcaagt tgcccaagcg     300
ggtattgatg caatcgcaca aacaagaccg gagcttgccg ctcgtatctt tatggtcgcg     360
attgaagaag ccaacggtaa acacgtaggt ttgacggaca tgatggttcg ttgggccaat     420
gaagacccat acttggcacc gaagcatggt tacaaaggcg aaacgccaag tgaccttggt     480
tttgatgcga agtaccacgt agatctaggt gagcattacg ctgatttcaa acagtggtta     540
gaaacgtccc agtcgaacgg gttgttgagt aaagcgacgt tggatgaatc cactaaaacg     600
gttcatcttg gctatagcta tcaagaactt caggatttga cgggtgctga atcggtgcaa     660
atggcgttct acttcctgaa agaagcggcg aagaaagcgg atccgatttc tggtgattca     720
gctgaaatga tactgctgaa gaaatttgca gatcaaagct acttatctca acttgattcc     780
gaccgaatgg atcaaattga aggtatctac cgcagtagcc atgagacgga tattgacgct     840
tgggatcgtc gttactctgg tacaggctat gatgagctga cgaataagct tgctagtgca     900
acgggcgttg acgagcagct tgcggttctt ctggatgatc gtaaaggcct cttgattggt     960
gaagtgcatg gcagcgacgt caacggccta cgctttgtta atgaacagat ggatgcactg    1020
aaaaaacagg gagtcacagt cattggcctt gagcatttac gctcagacct tgcgcaaccg    1080
ctgattgatc gctacctagc tacgggtgtg atgtcgagtg aactaagcgc aatgctgaaa    1140
acaaagcatc tcgatgtcac tcttttttgaa aacgcacgtg ctaacggtat gcgcatcgtc    1200
gcgctggatg caaacagctc tgcgcgtcca aatgttcagg aacagaaaca tggtctgatg    1260
taccgtgctg gtgctgcgaa caacattgcg gtggaagtat tacaaaatct gcctgatggc    1320
gaaaagttcg ttgctatcta cggtaaagcg catttgcagt ctcacaaagg gattgaaggg    1380
ttcgttcctg gtatcacgca ccgtctcgat cttcctgcgc ttaaagtcag tgactcgaac    1440
cagttcacag ttgaacaaga cgatgtaagt ctacgtgttg tctacgatga tgttgctaac    1500
aaaccgaaga tcacgttcaa gggcagtttg                                     1530

<210> SEQ ID NO 27
```

```
<211> LENGTH: 510
<212> TYPE: PRT
<213> ORGANISM: Homo sapiens
<220> FEATURE:
<221> NAME/KEY: MISC_FEATURE
<223> OTHER INFORMATION: RRSP

<400> SEQUENCE: 27
```

| Gly | Asp | Lys | Thr | Lys | Val | Val | Asp | Leu | Ala | Gln | Ile | Phe | Thr | Val |
|---|---|---|---|---|---|---|---|---|---|---|---|---|---|---|
| 1 | | | | 5 | | | | | 10 | | | | | 15 |

| Gln | Glu | Leu | Lys | Glu | Arg | Ala | Lys | Val | Phe | Ala | Lys | Pro | Ile | Gly | Ala |
|---|---|---|---|---|---|---|---|---|---|---|---|---|---|---|---|
| | | | 20 | | | | | 25 | | | | | 30 | | |

| Ser | Tyr | Gln | Gly | Ile | Leu | Asp | Gln | Leu | Asp | Leu | Val | His | Gln | Ala | Lys |
|---|---|---|---|---|---|---|---|---|---|---|---|---|---|---|---|
| | | | 35 | | | | | 40 | | | | | 45 | | |

| Gly | Arg | Asp | Gln | Ile | Ala | Ala | Ser | Phe | Glu | Leu | Asn | Lys | Lys | Ile | Asn |
|---|---|---|---|---|---|---|---|---|---|---|---|---|---|---|---|
| | 50 | | | | | 55 | | | | | 60 | | | | |

| Asp | Tyr | Ile | Ala | Glu | His | Pro | Thr | Ser | Gly | Arg | Asn | Gln | Ala | Leu | Thr |
|---|---|---|---|---|---|---|---|---|---|---|---|---|---|---|---|
| 65 | | | | | 70 | | | | | 75 | | | | | 80 |

| Gln | Leu | Lys | Glu | Gln | Val | Thr | Ser | Ala | Leu | Phe | Ile | Gly | Lys | Met | Gln |
|---|---|---|---|---|---|---|---|---|---|---|---|---|---|---|---|
| | | | | 85 | | | | | 90 | | | | | 95 | |

| Val | Ala | Gln | Ala | Gly | Ile | Asp | Ala | Ile | Ala | Gln | Thr | Arg | Pro | Glu | Leu |
|---|---|---|---|---|---|---|---|---|---|---|---|---|---|---|---|
| | | | 100 | | | | | 105 | | | | | 110 | | |

| Ala | Ala | Arg | Ile | Phe | Met | Val | Ala | Ile | Glu | Glu | Ala | Asn | Gly | Lys | His |
|---|---|---|---|---|---|---|---|---|---|---|---|---|---|---|---|
| | | 115 | | | | | 120 | | | | | 125 | | | |

| Val | Gly | Leu | Thr | Asp | Met | Met | Val | Arg | Trp | Ala | Asn | Glu | Asp | Pro | Tyr |
|---|---|---|---|---|---|---|---|---|---|---|---|---|---|---|---|
| | 130 | | | | | 135 | | | | | 140 | | | | |

| Leu | Ala | Pro | Lys | His | Gly | Tyr | Lys | Gly | Glu | Thr | Pro | Ser | Asp | Leu | Gly |
|---|---|---|---|---|---|---|---|---|---|---|---|---|---|---|---|
| 145 | | | | | 150 | | | | | 155 | | | | | 160 |

| Phe | Asp | Ala | Lys | Tyr | His | Val | Asp | Leu | Gly | Glu | His | Tyr | Ala | Asp | Phe |
|---|---|---|---|---|---|---|---|---|---|---|---|---|---|---|---|
| | | | | 165 | | | | | 170 | | | | | 175 | |

| Lys | Gln | Trp | Leu | Glu | Thr | Ser | Gln | Ser | Asn | Gly | Leu | Leu | Ser | Lys | Ala |
|---|---|---|---|---|---|---|---|---|---|---|---|---|---|---|---|
| | | | 180 | | | | | 185 | | | | | 190 | | |

| Thr | Leu | Asp | Glu | Ser | Thr | Lys | Thr | Val | His | Leu | Gly | Tyr | Ser | Tyr | Gln |
|---|---|---|---|---|---|---|---|---|---|---|---|---|---|---|---|
| | | 195 | | | | | 200 | | | | | 205 | | | |

| Glu | Leu | Gln | Asp | Leu | Thr | Gly | Ala | Glu | Ser | Val | Gln | Met | Ala | Phe | Tyr |
|---|---|---|---|---|---|---|---|---|---|---|---|---|---|---|---|
| | 210 | | | | | 215 | | | | | 220 | | | | |

| Phe | Leu | Lys | Glu | Ala | Ala | Lys | Lys | Ala | Asp | Pro | Ile | Ser | Gly | Asp | Ser |
|---|---|---|---|---|---|---|---|---|---|---|---|---|---|---|---|
| 225 | | | | | 230 | | | | | 235 | | | | | 240 |

| Ala | Glu | Met | Ile | Leu | Leu | Lys | Lys | Phe | Ala | Asp | Gln | Ser | Tyr | Leu | Ser |
|---|---|---|---|---|---|---|---|---|---|---|---|---|---|---|---|
| | | | | 245 | | | | | 250 | | | | | 255 | |

| Gln | Leu | Asp | Ser | Asp | Arg | Met | Asp | Gln | Ile | Glu | Gly | Ile | Tyr | Arg | Ser |
|---|---|---|---|---|---|---|---|---|---|---|---|---|---|---|---|
| | | | 260 | | | | | 265 | | | | | 270 | | |

| Ser | His | Glu | Thr | Asp | Ile | Asp | Ala | Trp | Asp | Arg | Arg | Tyr | Ser | Gly | Thr |
|---|---|---|---|---|---|---|---|---|---|---|---|---|---|---|---|
| | | 275 | | | | | 280 | | | | | 285 | | | |

| Gly | Tyr | Asp | Glu | Leu | Thr | Asn | Lys | Leu | Ala | Ser | Ala | Thr | Gly | Val | Asp |
|---|---|---|---|---|---|---|---|---|---|---|---|---|---|---|---|
| | 290 | | | | | 295 | | | | | 300 | | | | |

| Glu | Gln | Leu | Ala | Val | Leu | Leu | Asp | Arg | Lys | Gly | Leu | Leu | Ile | Gly |
|---|---|---|---|---|---|---|---|---|---|---|---|---|---|---|
| 305 | | | | | 310 | | | | | 315 | | | | | 320 |

| Glu | Val | His | Gly | Ser | Asp | Val | Asn | Gly | Leu | Arg | Phe | Val | Asn | Glu | Gln |
|---|---|---|---|---|---|---|---|---|---|---|---|---|---|---|---|
| | | | | 325 | | | | | 330 | | | | | 335 | |

| Met | Asp | Ala | Leu | Lys | Lys | Gln | Gly | Val | Thr | Val | Ile | Gly | Leu | Glu | His |
|---|---|---|---|---|---|---|---|---|---|---|---|---|---|---|---|
| | | | 340 | | | | | 345 | | | | | 350 | | |

| Leu | Arg | Ser | Asp | Leu | Ala | Gln | Pro | Leu | Ile | Asp | Arg | Tyr | Leu | Ala | Thr |
|---|---|---|---|---|---|---|---|---|---|---|---|---|---|---|---|
| | | 355 | | | | | 360 | | | | | 365 | | | |

| Gly | Val | Met | Ser | Ser | Glu | Leu | Ser | Ala | Met | Leu | Lys | Thr | Lys | His | Leu |
|---|---|---|---|---|---|---|---|---|---|---|---|---|---|---|---|

```
                370                 375                 380
Asp Val Thr Leu Phe Glu Asn Ala Arg Ala Asn Gly Met Arg Ile Val
385                 390                 395                 400

Ala Leu Asp Ala Asn Ser Ser Ala Arg Pro Asn Val Gln Gly Thr Glu
                405                 410                 415

His Gly Leu Met Tyr Arg Ala Gly Ala Asn Asn Ile Ala Val Glu
                420                 425                 430

Val Leu Gln Asn Leu Pro Asp Gly Glu Lys Phe Val Ala Ile Tyr Gly
                435                 440                 445

Lys Ala His Leu Gln Ser His Lys Gly Ile Glu Gly Phe Val Pro Gly
                450                 455                 460

Ile Thr His Arg Leu Asp Leu Pro Ala Leu Lys Val Ser Asp Ser Asn
465                 470                 475                 480

Gln Phe Thr Val Glu Gln Asp Asp Val Ser Leu Arg Val Val Tyr Asp
                485                 490                 495

Asp Val Ala Asn Lys Pro Lys Ile Thr Phe Lys Gly Ser Leu
                500                 505                 510

<210> SEQ ID NO 28
<211> LENGTH: 14
<212> TYPE: PRT
<213> ORGANISM: Corynebacterium diphtheriae
<220> FEATURE:
<221> NAME/KEY: MISC_FEATURE
<223> OTHER INFORMATION: delta-dta

<400> SEQUENCE: 28

Cys Ala Gly Asn Arg Val Arg Arg Ser Val Gly Ser Ser Leu
1               5                   10

<210> SEQ ID NO 29
<211> LENGTH: 15
<212> TYPE: PRT
<213> ORGANISM: Artificial Sequence
<220> FEATURE:
<223> OTHER INFORMATION: Strep Tag (TM) II

<400> SEQUENCE: 29

Leu Val Pro Arg Gly Ser Ala Trp Ser His Pro Gln Phe Glu Lys
1               5                   10                  15

<210> SEQ ID NO 30
<211> LENGTH: 543
<212> TYPE: PRT
<213> ORGANISM: Clostridium difficile
<220> FEATURE:
<221> NAME/KEY: MISC_FEATURE
<223> OTHER INFORMATION: contains glucosyl transferase domain

<400> SEQUENCE: 30

Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
                20                  25                  30

Glu Tyr His Asn Met Ser Glu Asn Thr Val Val Glu Lys Tyr Leu Lys
            35                  40                  45

Leu Lys Asp Ile Asn Ser Leu Thr Asp Ile Tyr Ile Asp Thr Tyr Lys
        50                  55                  60

Lys Ser Gly Arg Asn Lys Ala Leu Lys Lys Phe Lys Glu Tyr Leu Val
65                  70                  75                  80
```

-continued

```
Thr Glu Val Leu Glu Leu Lys Asn Asn Leu Thr Pro Val Glu Lys
                 85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365

Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
            420                 425                 430

Asp Ser Ile Met Ala Glu Ala Asn Ala Asp Asn Gly Arg Phe Met Met
        435                 440                 445

Glu Leu Gly Lys Tyr Leu Arg Val Gly Phe Phe Pro Asp Val Lys Thr
    450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
```

```
                500                 505                 510
Glu Gln Glu Met Ala Ser Leu Trp Ser Phe Asp Asp Ala Arg Ala Lys
        515                 520                 525

Ala Gln Phe Glu Glu Tyr Lys Arg Asn Tyr Phe Glu Gly Ser Leu
        530                 535                 540
```